US012326450B2

(12) United States Patent
Larijani et al.

(10) Patent No.: US 12,326,450 B2
(45) Date of Patent: Jun. 10, 2025

(54) KITS, METHODS AND THEIR USES FOR DETECTING CELL-CELL INTERACTIONS IN A SAMPLE

(71) Applicant: Fastbase Solutions Ltd, Derio (ES)

(72) Inventors: Banafshe Larijani, Derio (ES); Raj Mehta, London (GB); Peter Parker, Dorking (GB); Lissete Sanchez Magraner, Derio (ES)

(73) Assignee: Fastbase Solutions SL, Derio (ES)

( * ) Notice: Subject to any disclaimer, the term of this patent is extended or adjusted under 35 U.S.C. 154(b) by 1007 days.

(21) Appl. No.: 16/613,723

(22) PCT Filed: May 16, 2018

(86) PCT No.: PCT/EP2018/062719
§ 371 (c)(1),
(2) Date: Nov. 14, 2019

(87) PCT Pub. No.: WO2018/210927
PCT Pub. Date: Nov. 22, 2018

(65) Prior Publication Data
US 2020/0072835 A1    Mar. 5, 2020

(30) Foreign Application Priority Data

May 16, 2017   (GB) .................................... 1707859

(51) Int. Cl.
*G01N 33/569*   (2006.01)
*G01N 33/542*   (2006.01)
*G01N 33/574*   (2006.01)

(52) U.S. Cl.
CPC ..... *G01N 33/56966* (2013.01); *G01N 33/542* (2013.01); *G01N 33/574* (2013.01);
(Continued)

(58) Field of Classification Search
CPC .......... G01N 33/56966; G01N 33/542; G01N 33/574; G01N 2333/70596; G01N 2500/02; G01N 2500/10
See application file for complete search history.

(56) References Cited

U.S. PATENT DOCUMENTS

| 10,184,944 B2 * | 1/2019 | Larijani | ........... G01N 33/57415 |
| 10,578,620 B2 * | 3/2020 | Larijani | ........... G01N 33/57415 |

(Continued)

FOREIGN PATENT DOCUMENTS

| EP | 3 147 664    | * | 3/2017 | ........... G01N 33/574 |
| EP | 3 147 664 A1 | * | 3/2017 | ........... G01N 33/574 |

(Continued)

OTHER PUBLICATIONS

Bastiaens, P.I.H., et al; "Fluorescence Resonance Energy Transfer Microscopy", Light Microscopy and Contrast Generation, pp. 136-146 (1998).

(Continued)

*Primary Examiner* — Gailene Gabel
(74) *Attorney, Agent, or Firm* — Knobbe, Martens, Olson & Bear, LLP

(57) ABSTRACT

The present invention provides an in vitro method for detecting cell-cell interactions and associated kits and uses, where the method comprises: (a) at least two primary binding agents, wherein the first primary binding agent binds to a first molecule on a first cell and the second primary binding agent binds to a second molecule on a second cell, and wherein the first and second primary binding agents are immunologically distinct; (b) at least two secondary binding agents, wherein a first secondary binding agent binds to the first primary binding agent; and a second secondary binding agent binds the second primary binding (Continued)

Förster resonance energy transfer can measure cell-cell interaction using the programmed death receptor-1 and programmed death-ligand 1 pair in primary renal cell carcinoma tissue. Bar chart plots representing FRET efficiency values for (A) patients 1-10, (B) patients 11-20 and (C) patients 21-30. Two samples (a and b) are presented per patient representing alternative tumour regions. Each plot contains three identical renal control values (C1, C2 and C3).

agent, wherein the first secondary binding agent does not bind the second primary binding agent and the second secondary binding agent does not buy the first primary binding agent; and wherein: (i) the first secondary binding agent is labelled with a FRET donor and the second secondary binding agent is labelled with a FRET acceptor; (ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme; wherein the method comprises: i. contacting an isolated sample containing cells with the at least two primary binding agents; ii. contacting the sample with the at least two secondary binding agents; iii. performing a wash step; iv. detecting the interaction between the secondary binding agents.

24 Claims, 14 Drawing Sheets

(52) U.S. Cl.
CPC .............. *G01N 2333/70596* (2013.01); *G01N 2500/02* (2013.01); *G01N 2500/10* (2013.01)

(56) References Cited

U.S. PATENT DOCUMENTS

| | | | | |
|---|---|---|---|---|
| 2016/0069881 | A1* | 3/2016 | Larijani | G01N 33/54373 435/7.92 |
| 2019/0064156 | A1* | 2/2019 | Wallweber | G01N 33/542 |

FOREIGN PATENT DOCUMENTS

| | | | | |
|---|---|---|---|---|
| GB | 2511761 | A | | 9/2014 |
| GB | 2511791 | * | | 9/2014 ........... G01N 33/542 |
| WO | WO 2011/161420 | A2 | | 12/2011 |
| WO | WO 2013/049398 | A2 | | 4/2013 |
| WO | WO 2014/140554 | A1 | | 9/2014 |
| WO | WO 2016/083364 | A1 | | 6/2016 |
| WO | WO 2017/050855 | A1 | | 3/2017 |
| WO | WO 2017/053762 | A1 | | 3/2017 |
| WO | WO 2017/161030 | A1 | | 9/2017 |

OTHER PUBLICATIONS

Cong, M., et al.; "Reporter Bioassays to Assess Therapeutic Antibodies in Development for Immunotherapy Programs", Promega Corporation. May 2015.
Wallweber, G., et al.; "Abstract No. 3225; Development of a proximity-based immunoassay to measure the PD1;PD-L1 complex in fixed samples", AACR Annual Meeting, Apr. 16-20, 2016.
Waterhouse et al. "Assessment of EGFR/HER2 dimerization by FRET-FLIM utilizing Alexa-conjugated secondary antibodies in relation to targeted therapies in cancers." Oncotarget, vol. 2. No. 9, pp. 728-736 (2011).
Maszczak-Seneczko, D. et al., In Situ Proximity Ligation Assay (PLA) Analysis of Protein Complexes Formed Between Golgi-Resident, Glycosylation-Related Transporters and Transferases in Adherent Mammallan Cell Cultures Methods Mol. Biol., vol. 1496, pp. 133-144 (2016).
Wu, Yung-Hsuan, et al. "Measuring NLR Ollgomerization V; In Situ Proximity Ligation Assay" Methods Mol. Biol., vol. 1417, pp. 185-196 (2016).
Konig, P. et al., "FRET-CLSM and double labeling indirect immunofluorescence to detect close association of proteins in tissue sections" Lab. Invest., vol. 8,, pp. 853-864 (2006).
Sánchez-Magraner, Lissete, et al. "High PD-1/PD-L1 Checkpoint Interaction Infers Tumor Selection and Therapeutic Sensitivity to Anti-PD-1/PD-L1 TreatmentTherapeutic Sensitivity to PD-1 & PD-L1 Interaction." *Cancer Research* 80.19 (2020): 4244-4257.
Office Action in Japanese Patent Application No. 2022-053100, mailed Jan. 31, 2023.
Communication pursuant to Article 94(3) EPC issued in EP Application No. 18724560.0, dated Aug. 25, 2023.
Examination Report issued in Australian Application No. 2018268001, dated Dec. 11, 2023.
Decision of Refusal issued in Japanese Application No. 2022-053100, dated Sep. 12, 2023.
Examiner's Requisition issued in Canadian Application No. 3,061,679, dated Jun. 18, 2024.
Office Action issued in Chinese Application No. 201880044554.8, dated Dec. 19, 2024.
Notice of Reasons for Refusal issued in Japanese Application No. 2022-053100, dated Mar. 17, 2025.

* cited by examiner

VARIATIONS IN PD-1 PD-L1 INTERACTIONS BY A-FRET IN PATIENTS TREATED WITH ANTI-RTK DRUGS AND ANTIBODY BLOCKING PD-1. The changes in the donor life time (PD-1) are indicated by a decrease to a shorter lifetime in the presence of the acceptor (PDL1).

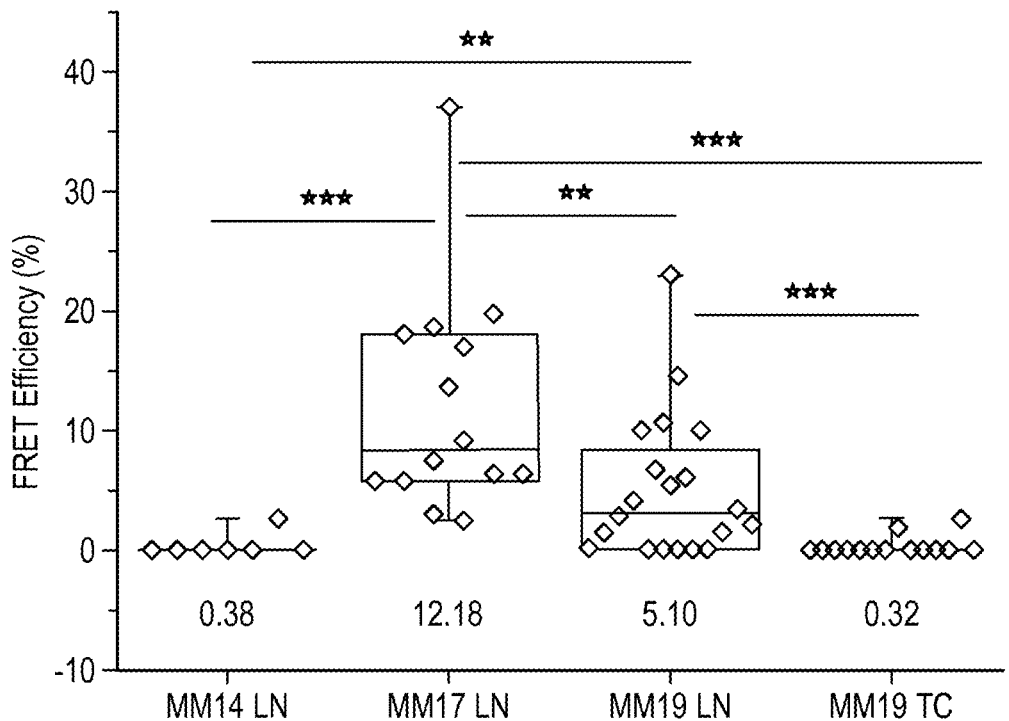

Figure 2

VARIATIONS IN PD-1 PD-L1 INTERACTIONS BY A-FRET IN PATIENTS TREATED WITH ANTI-RTK DRUGS AND ANTIBODY BLOCKING PD-1. The median FRET efficiencies of the Box and Whiskers plots show the variations in PD-1 PD-L1 interactions. P values indicate the highly significant differences in the FRET efficiencies. Each data point represents a region on the provided tissue where the highest receptor concentration (PD-1) is accumulated.

PD-1 AND PD-L1 INTERACTION CAN BE QUANTIFIED BY IFRET - THE INTERACTION CAN BE INHIBITED AND QUANTIFIED BY IFRET. The changes in the donor lifetime (PD-1) are indicated by a decrease to a shorter lifetime in the presence of the acceptor (PD-L1).

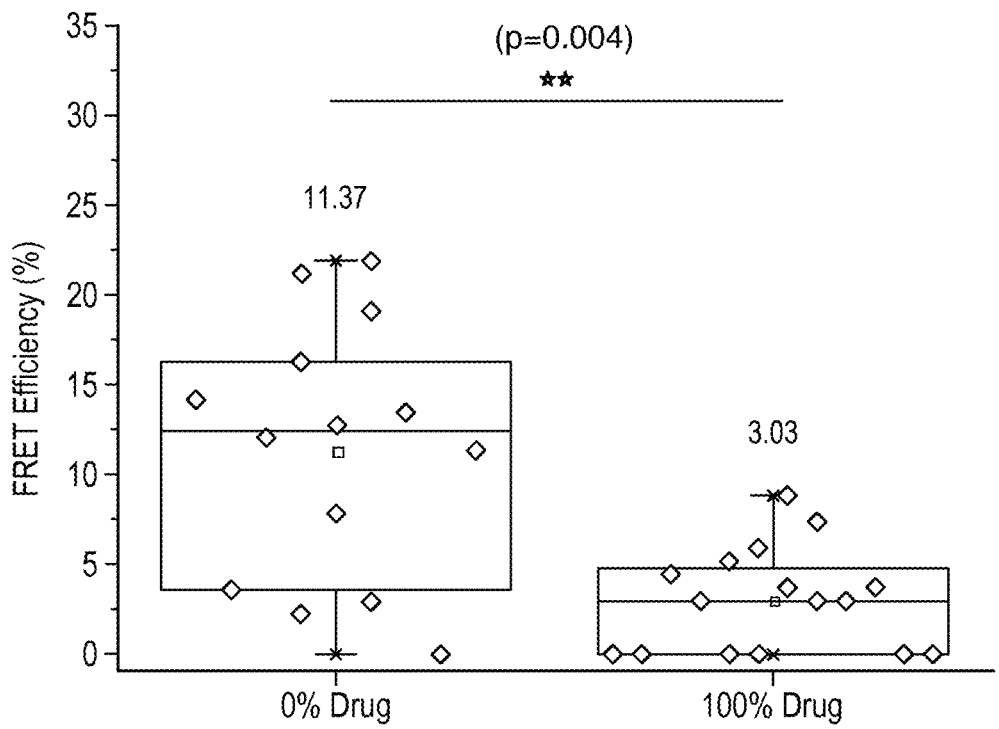

Figure 4

PD-1 AND PD-L1 INTERACTION CAN BE QUANTIFIED BY IFRET - THE INTERACTION CAN BE INHIBITED AND QUANTIFIED BY IFRET. Box and Whisker plots representing FRET efficiency of PD-1/PD-L1 in the presence and absence of 25μg/ml of blocking drug (anti PD-1 monoclonal antibody). Each point on the Box and Whiskers plots was a region of interest containing an average of 5 cells. The P value was determined by a Mann-Whitney non parametric test.

FRET measures the interaction between CTLA-4 and CD80 in single cells. Images shown represents the intensity of CTLA-4, acquired by using a modulated 473nm laser, the intensity of CD80, acquired using a mercury source, and lifetime maps in the absence (A) and presence (B) of anti-CTLA-4 ipilimumab. Lifetime images were fitted to a pseudo-colour scale with higher lifetimes indicated by dark blue and lower lifetimes indicated in red. In the absence of ipilimumab, donor and donor/acceptor lifetimes ($\tau$) were 1.96 ± 0.17 ns and 1.45 ± 0.11 ns respectively. In contrast, the presence of ipilimumab resulted in a donor $\tau$ of 2.06 ± 0.12 ns and donor/acceptor $\tau$ of 1.98 ± 0.09 ns.

Figure 5 (continued)

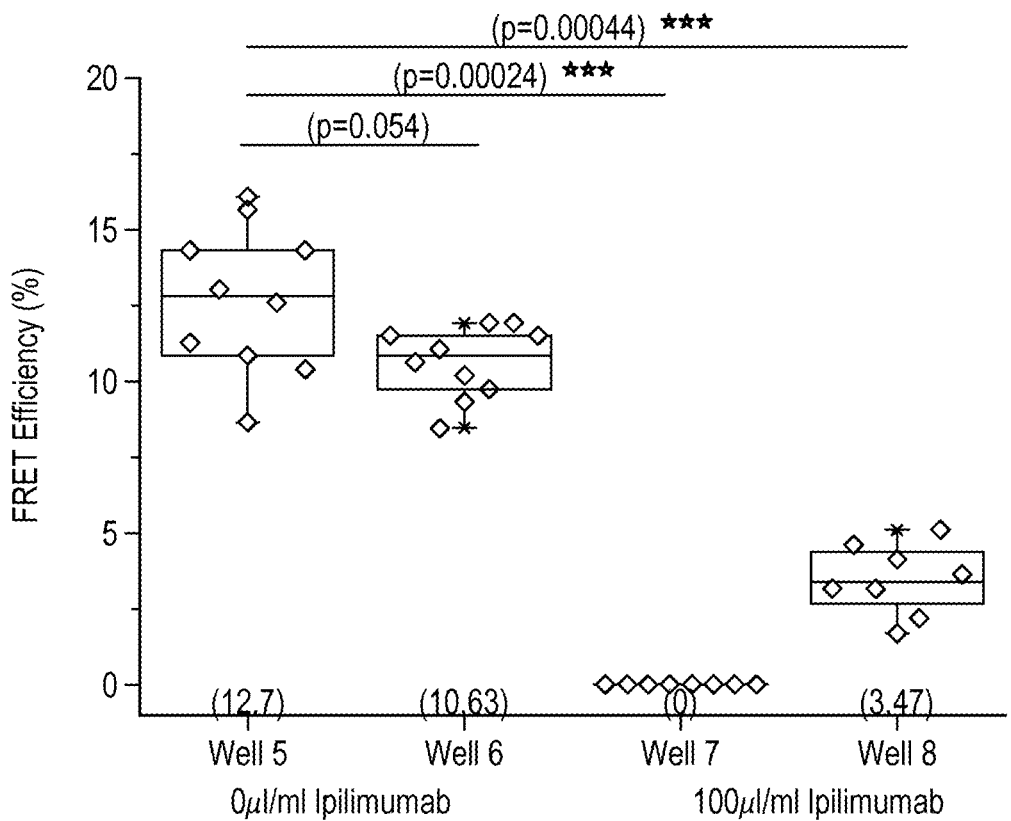

Figure 6

Ipilimumab inhibits interaction between CTLA-4 and CD8- determined by i-FRET. Box and whisker plots demonstrate FRET efficiency in each condition, with the mean FRET efficiencies indicated. The Mann Whitney U test was carried out to analyse significance between conditions. Statistical differences are observed between untreated cells and thos treated with 100 µL/mL ipilimumab Förster resonance energy transfer can measure the interaction of cytotoxic T-lymphocyte associated protein-4 (CTLA-4) and cluster differentiation 80 (CD80) in metastatic melanoma tissue. Metastatic melanoma tissue samples obtained from different patients each given a unique MM number. Samples from both the lymph node (LN) and transverse colon (TC) are presented. (A) Intensity of CTLA-4, acquired using modulated 473 nm laser, intensity of CD80, acquired using a mercury source, and lifetime maps in the MM19TC patient condition. Lifetime images were fitted to a pseudo-colour scale with higher lifetimes indicated by dark blue and lower lifetimes indicated in red. A decrease in donor lifetime is observed between the donor only and donor/acceptor conditions. Localised lifetimes ($\tau$) and standard deviations are indicted (B). Box and Whisker plots represent FRET efficiency in each sample, with the mean FRET efficiencies indicated. Boxes and Whiskers represent 25-75% and 1=99% ranges of data respectively. Mann Whitney U analysis was carried out to determine significance between conditions. Significant differences were observed between MM19LN and both MM17LN and MM19TC.

Figure 7 (continued)

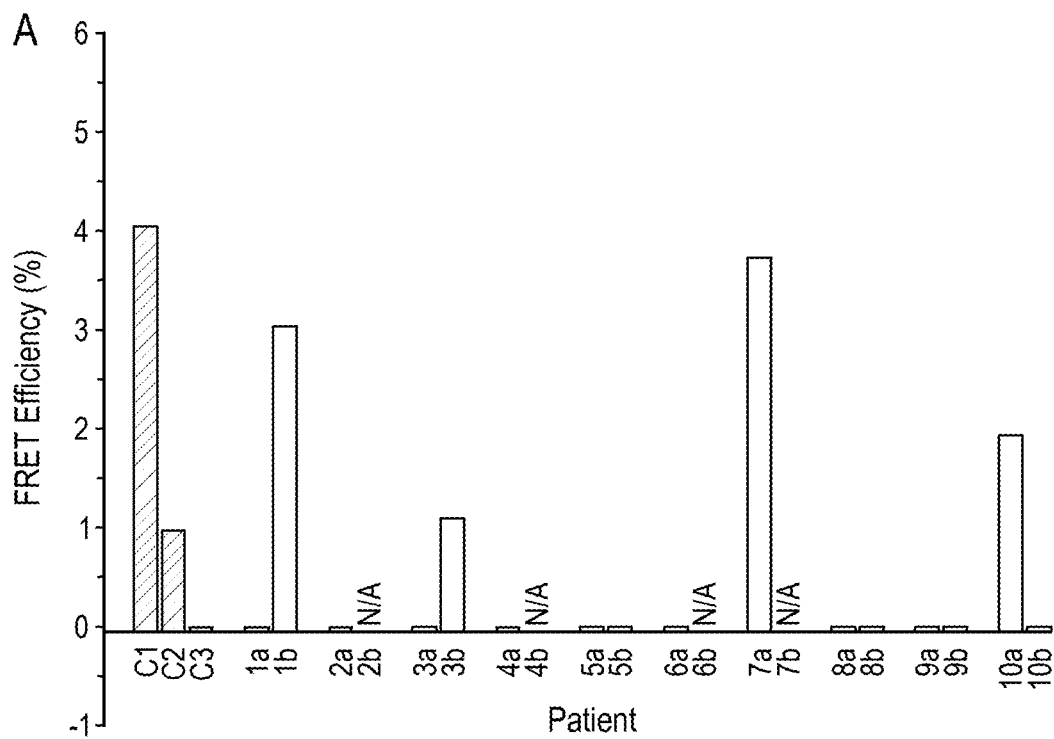
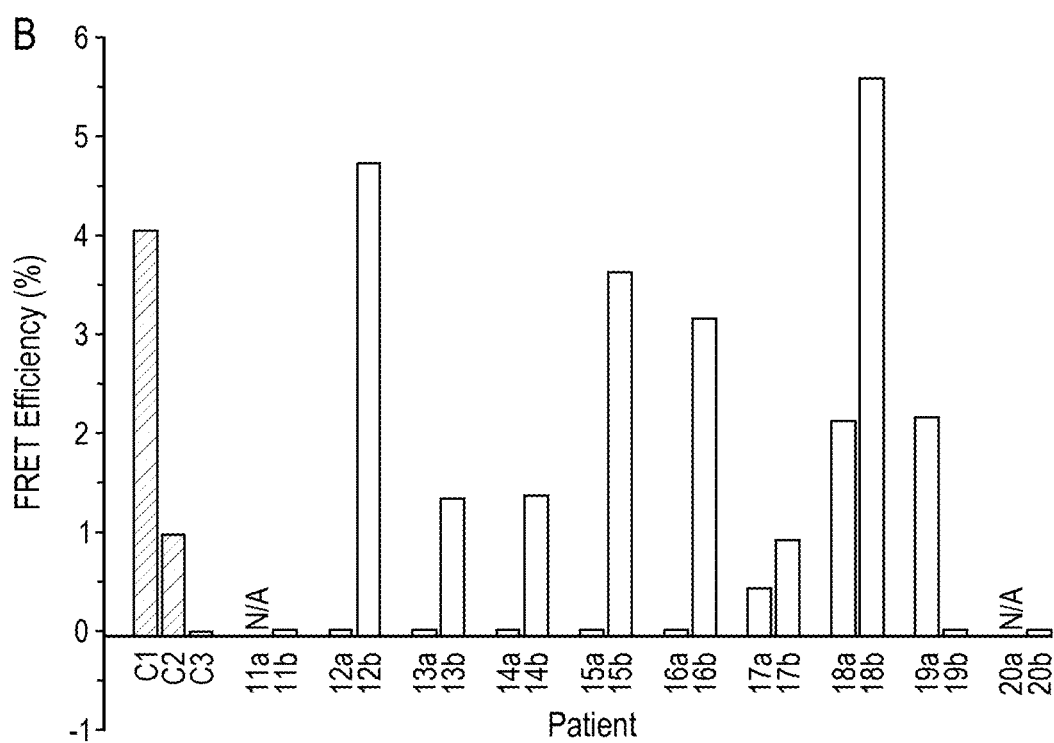
Figure 8

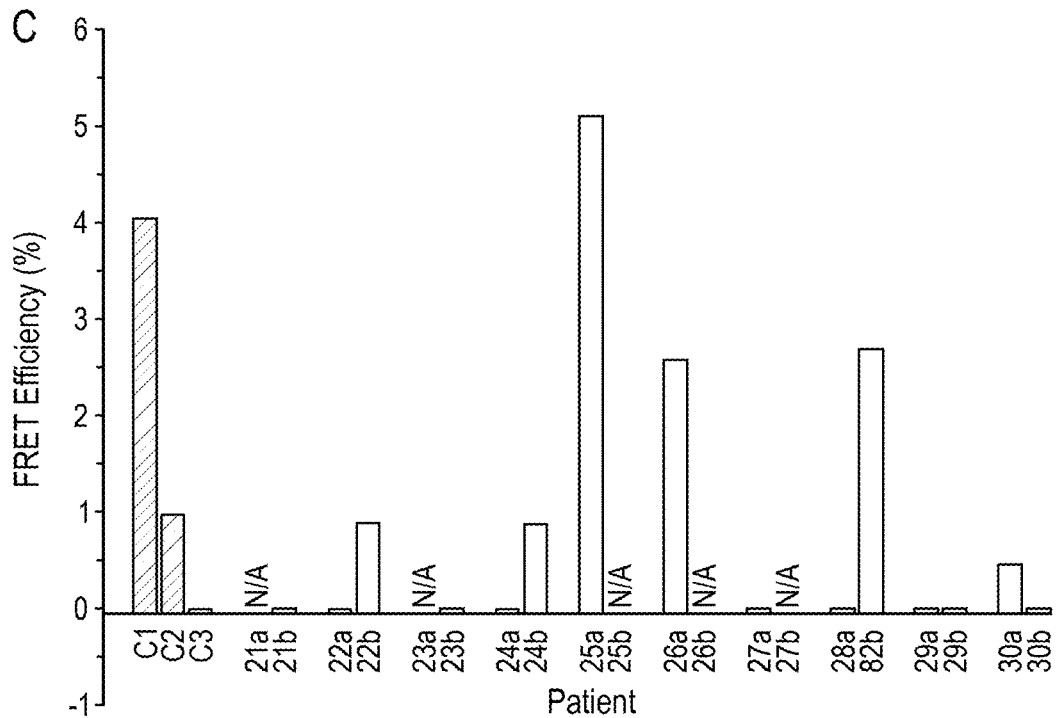

Figure 8 (cont.)

Förster resonance energy transfer can measure cell-cell interaction using the programmed death receptor-1 and programmed death-ligand 1 pair in primary renal cell carcinoma tissue. Bar chart plots representing FRET efficiency values for (A) patients 1-10, (B) patients 11-20 and (C) patients 21-30. Two samples (a and b) are presented per patient representing alternative tumour regions. Each plot contains three identical renal control values (C1, C2 and C3).

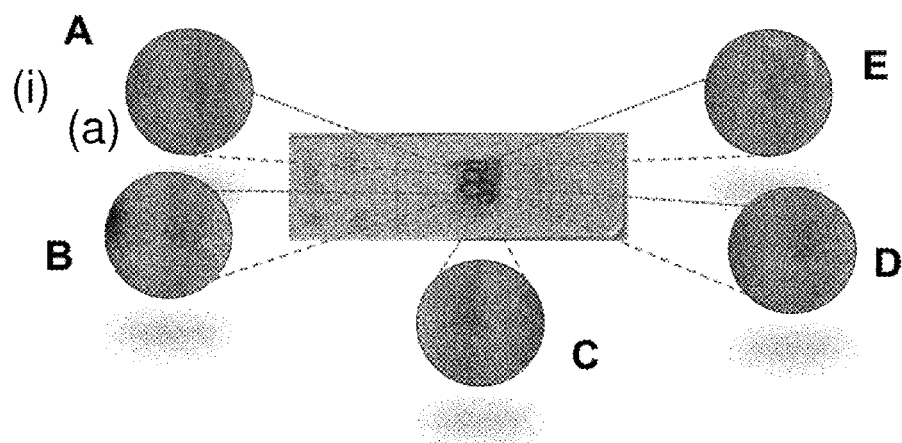
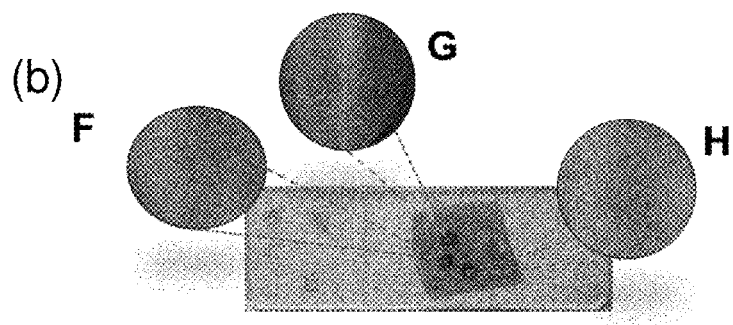
Figure 9

(ii)

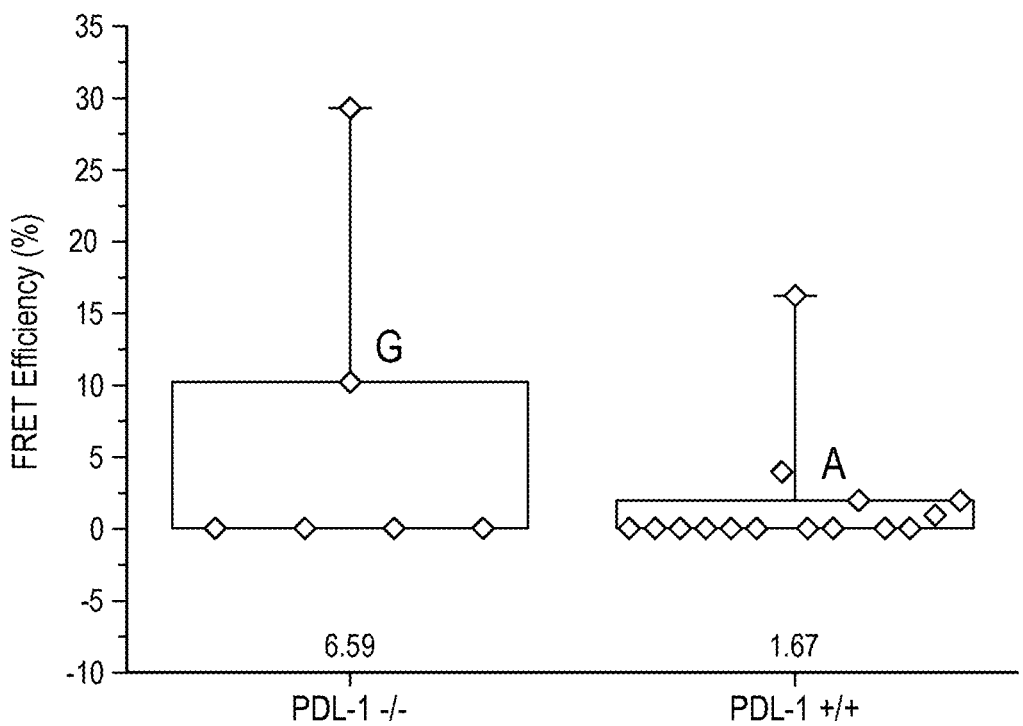

Figure 9 (cont.)

Förster resonance energy transfer can measure the interaction of programmed death receptor-1 and programmed death- ligand 1 in ccRCC patient samples.

(i) Haematoxylin and Eosin labelling of (a) PD-L1 +/+ and (b) PD-L1 -/- tissue samples. Regions of interest provided indicate immune cell infiltration.

(ii) Box and Whiskers plots represent FRET efficiency in each region of interest, with the mean FRET efficiencies indicated. Boxes and Whiskers represent 25-75% and 1-99% ranges of data respectively.

KITS, METHODS AND THEIR USES FOR DETECTING CELL-CELL INTERACTIONS IN A SAMPLE

DESCRIPTION OF THE INVENTION

The invention relates to kits and methods of detecting cell-cell interactions, particularly in a fixed sample. The invention further provides for the quantification of cell-cell interactions. In particular, the invention relates to the detection of the interaction between two molecules expressed on two different cells in close proximity. For example, the invention relates to the interaction between immune check point proteins at the cellular level displayed on the cell surface of different cells in close proximity, such as the interaction between PD-1 and PD-L1/PD-L2.

The invention relates to kits and methods using coincidence assays, such as proximity ligation assays, coincidence detection or Förster (fluorescence) resonance energy transfer (FRET) alone or in combination with an enzyme activation system, such as tyramide signal amplification (TSA), to improve detection of cell-cell interactions in a sample. More specifically, the invention relates to two site methods, where the two sites are on different molecules (e.g. proteins) expressed on different cells. The methods and kits can be used to determine whether checkpoint protein inhibitors are likely to be effective in treating cancer.

The invention also relates to kits and methods for the prediction and identification of patients likely to respond to cancer treatments, such as the inhibition of the PD-1:PD-L1/PD-L2 pathway, as well as to stratify patients that do not respond to such treatments and to provide for the determination of treatment options for patients based on their responder/non-responder profile.

The invention can be used to analyse tumour samples and can be applied in the diagnosis, monitoring, stratification and treatment of cancer patients, and drug development in the cancer field.

BACKGROUND

Cell-cell communication is critical to the functioning of multicellular organisms. The modulation, overstimulation or breakdown of cell-cell signalling can lead to various disease states. Thus, research efforts have been focussed on examining and elucidating cell-cell interactions with a view to (a) determining new therapeutic targets, (b) guiding patient selection, and (c) monitoring treatment efficacy in a variety of disease states.

One aspect where the detection and quantification of cell-cell interactions is critical is in examining the interaction between immune cells and non-immune cells in the maintenance of a healthy immune system. Disruption or aberrant interactions in this context can lead to various disease states, from over-active immune responses to inflammatory disease states and tumours causing an under-active immune response.

Indeed, understanding, measuring and quantifying the ability of tumour cells to evade immune cell-mediated destruction by binding and inhibiting T-cells has become a major concern. Failure to appreciate this is thought to be one of the main reasons why therapeutic applications, which limit the inhibitory T-cell-tumour cell interaction, are restricted to modulating the interaction of specific T-cell and tumour cell proteins.

Cancer immunotherapy research is trying to overcome tumour cells' ability to evade immune-mediated destruction, and to stimulate an individual's immune system to target tumour cells.

One of the most promising approaches to overcoming the ability of tumour cells to evade immune-cell mediated destruction is the blockade of immune checkpoint markers. Immune checkpoints refer to numerous immuno-inhibitory pathways crucial for maintaining self-tolerance and modulating the severity of an immune response to minimise unnecessary damage to non-pathogenic tissues. It is known that tumour cells hijack these immunosuppressive checkpoint pathways, acting as a major mechanism for evading destruction by T-cells that are specific for tumour antigens. The inhibitory interactions between T-cell and tumour cell surface checkpoint proteins are thus attractive therapeutic targets for cancer treatment.

Indeed, therapeutic antibodies that block T-cell: tumour cell checkpoint inhibitory interactions have proved successful at reducing tumour volume in a clinical setting. However, these treatments are limited to very few immune checkpoints as there are no methods or assays available to detect which immune checkpoints will be promising targets for cancer treatment.

Furthermore, there are potentially numerous, as yet undiscovered, checkpoint interactions that are likely to exist. Clearly, methods are needed that allow for the detection of cell-cell interactions, such as T-cell: tumour cell checkpoint interactions.

A well characterised immune checkpoint protein interaction is the binding of programmed cell death-1 (PD-1) receptor, also known as cluster of differentiation (CD)279, and either of the ligands programmed cell death-ligand 1 or 2 (PD-L1 or 2), also known as CD274 or CD273 respectively. PD-1 is expressed on the surface of activated T-cells, whereas PD-L1/2 is expressed on antigen-presenting cells, such as dendritic cells and macrophages, as well as tumour cells. Binding of PD-1 to PD-L1/2 produces an inhibitory signal within the T-cell, which halts or limits T-cell proliferation and cytokine production. The PD-1:PD-L1/2 interaction ensures that the immune system is activated at the correct time, therefore minimising potential autoimmunity. Cancer tumour cells exploit the PD-1:PD-L1/PD-L2 checkpoint pathway, providing a mechanism to avoid detection, and subsequent T-cell-mediated destruction. Therapies blocking PD-1:PD-L1/PD-L2 have shown unprecedented rates of durable tumour responses in a variety of cancer types (Ribas et al., Clin. Cancer Res; 20(19) 2014).

Another well characterised immune checkpoint protein interaction is the binding of cytotoxic T-lymphocyte-associated protein 4 (CTLA-4), also known as CD152, and either of the ligands cluster of differentiation 80 (CD80) or 86 (CD86), also known as B7-1 and B7-2 respectively. CTLA-4 is expressed on activated T-cells, whereas CD80 and CD86 are expressed on antigen presenting cells, such as dendritic cells or macrophages. Binding of CTLA-4 to CD80/86 produces an inhibitory signal to the T-cell, which halts or limits T-cell proliferation and cytokine production. The CTLA-4/CD80/86 interaction ensures that the immune system is activated at the correct time, therefore minimising potential autoimmunity. Cancer tumour cells exploit the CTLA-4/CD80/86 checkpoint pathway, providing a mechanism to avoid detection, and subsequent destruction, by T-cells. Therapies such as the monoclonal antibody Ipilimumab blocking the CTLA-4/CD80/86 results in increased activation of the immune system and tumour regression in a variety of cancer types (Buchbinder, El & Desai, A. American Journal of Clinical Oncology; 39(1) 2016).

The assessment of cell-cell interactions has not been extensively reported, partly due to a lack of available methods/technologies that allow for the detection of cell-cell interactions in a fixed sample. Typically, routine proteomics applied to tumour samples rely on immunohistochemistry (IHC) to determine relative protein content, or on extraction and processing, such as enzyme-linked immunosorbent assay (ELISA). Although conventional IHC minimises manipulation and retains tissue organisation, it is limited in its specificity (one-site assay). ELISA-type approaches can bring specificity (two site assays) but require processing, which provides sample size challenges, and destroys spatial information. Current systems have only been used to detect the interaction between molecules either in solution (soluble recombinant proteins) or within a single cell. For example, the interaction of PD-1:PD-L1/PD-L2 by FRET has previously been studied but only in the context of an assay in solution using recombinant or purified proteins.

WO 2014/140554 describes methods for detecting molecules in a sample utilising fluorescence resonance energy transfer (FRET) in combination with a tyramide activation system (TSA) in a two-site detection method. However, such methods were limited in their use to the detection and quantification of two sites on the same protein or two sites on different proteins in the context of the same cell. Thus, current detection methods are limited in their specificity and sensitivity, and are unable to detect and quantify interactions at the cellular level.

Previous methods known in the art rely on a qualitative, intensity based assessment by detecting co-localisation of overlapping immune signals to detect cell-cell interactions and manually counting the number of overlapping signals and estimating the ratio of the number of signals: the number of nuclei.

There remains a need to provide sensitive and specific methods to detect and quantify the interaction between molecules (e.g. two proteins) presented on the cell surface of two separate cells, in particular immune checkpoint protein interactions, to aid in developing improved and effective methods for identifying and treating cancer patients.

The objective of the present invention is to provide an improved method and kit for detecting cell-cell interactions between two molecules expressed on two different cells, particularly immune check point protein interactions (such as PD-1:PD-L1/PD-L2, major histocompatibility complex (MHC) I-II: T-cell receptor (TCR)/CD8/CD3 or CTLA-4/CD80/86) on the surface of different cells, in a fixed sample, such as tissue sections. A further objective of the present invention is to provide an effective method and kit for the prediction and identification of patients likely to respond to cancer treatments, such as the inhibition of the PD-1:PD-L1/PD-L2, MHC I-II:TCR/CD8/CD3 or CTLA-4/CD80/86 pathways, as well as to stratify patients that do not respond to such treatments and to provide for the determination of treatment options for patients based on their responder/non-responder profile.

SUMMARY OF THE INVENTION

The present invention provides a method, for detecting and quantifying cell-cell interactions. In particular, the present invention relates to methods for detecting and quantifying interactions between molecules on different cells, such as protein-protein interactions, where the proteins are each on the surface of different cells i.e. in trans. In particular, the present invention relates to the detection and quantification of immune check point protein interactions, such as the interaction between PD-1 and PD-L1 or PD-L2, or the interaction between CTLA-4 or CD28 and CD80 or 86, or the interaction between a MHC class I or MHC class II peptide and TCR, CD83, CD3 and combinations thereof, at the cellular level.

According, to the present invention, there is provided an in vitro method for detecting cell-cell interactions, the method comprising:

at least two primary binding agents, wherein the first primary binding agent binds to the first molecule on the first cell and the second primary binding agent binds to the second molecule on the second cell, and wherein the first primary and secondary primary binding agents are immunologically distinct;

at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:

(i) the first secondary binding agent is labelled with a FRET donor and the second secondary binding agent is labelled with a FRET acceptor;

(ii) the first and second secondary binding agent are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(a) contacting an isolated sample containing cells with the at least two primary binding agents;
(b) contacting the sample with the at least two secondary binding agents;
(c) performing a wash step;
(d) detecting the interaction between the secondary binding agents.

In the methods, kits and uses of the invention, detecting the interaction between the secondary binding agents can be by detecting the emitted fluorescence.

In the methods, kits and uses of the invention, detecting the interaction between the secondary binding agents can be by detecting the altered fluorescence behaviour. Preferably, detecting the altered fluorescence behaviour is time-resolved.

In the methods, kits and uses of the invention, the first cell and the second cell can be the same type of cell.

In the methods, kits and uses of the invention, the first cell and the second cell can be different types of cell i.e. not the same type of cell.

In the methods, kits and uses of the invention, the isolated sample can be a fixed cell sample. In the methods, kits and uses of the invention, the isolated sample can be a fixed tumour cell sample.

In the methods, kits and uses of the invention, the first and second molecules can be proteins, preferably endogenous proteins. Preferably, the proteins are immune checkpoint proteins.

In methods, kits and uses of the invention, the first molecule can be PD-1 and the second molecule can be PD-L1 or PD-L2.

In the methods, kits and uses of the invention the first molecule can be CTLA-4 or CD28 and the second molecule can be CD80 or CD86.

In the methods, kits and uses of the invention, the first molecule can be an MHC Class I or II peptide and the second molecule can be selected from TCR, CD8, CD3 and combinations thereof.

In the methods, kits and uses of the invention, the at least two primary binding agents can be selected from the group consisting of whole immunoglobulins, antibody scaffolds, antibody or antigen-binding fragments thereof or combinations thereof.

In the methods, kits and uses of the invention, the at least two secondary binding agents can be selected from the group consisting of whole immunoglobulins, antibody scaffolds or antibody or antigen-binding fragments thereof or combinations thereof.

In the methods, kits and uses of the invention, at least one of the secondary binding agents can be an antibody scaffold, antibody or antigen-binding fragment. In the methods, kits and uses of the invention, the at least two secondary binding agents can be antibody scaffolds, antibody binding fragments or antigen-binding fragments.

In the methods, kits and uses of the invention, the antibody or antigen-binding fragments can Fab fragments, scFv fragments or combinations thereof.

In the methods, kits and uses of the invention, the antibody scaffolds can be adnectins, affibodies, affilins, anticalins, atrimers, avimers, bicyclic peptides, centyrins, cysknots, DARPins, fynomers, Kunitz domains, Obodies, and Tn3s.

In the methods, kits and uses of the invention, the primary binding agents can be unlabelled.

In the methods, kits and uses of the invention, the first primary binding agent can be a murine binding agent and the at least one other primary binding agent can be a rabbit binding agent.

In the methods, kits and uses of the invention, the first primary binding agent can bind to PD-1 and the at least one other primary binding agent can bind to PD-L1 or PD-L2.

In the methods, kits and uses of the invention, the first primary binding agent can bind to PD-1 on the first cell and the at least one other primary binding agent can bind to PD-L1 or PD-L2 on the second cell.

In the methods, kits and uses of the invention, the method can detect binding of PD-1 to PD-L1 or PD-L2.

In the methods, kits and uses of the invention, the first molecule can be CTLA-4 or CD28 and the second molecule can be CD80 or CD86.

In the methods, kits and uses of the invention, the first primary binding agent can bind to CTLA-4 or CD28 on the first cell and the at least one other primary binding agent can bind to CD80 or CD86 on the second cell.

In the methods, kits and uses of the invention, the method can detect binding of CTLA-4 or CD28 to CD80 or CD86.

In the methods, kits and uses of the invention, the first molecule can be an MHC Class I or II peptide and the second molecule can be selected from TCR, CD8, CD3 and combinations thereof.

In the methods, kits and uses of the invention, the first primary binding agent can bind to an MHC class I or MHC class II peptide and the second primary binding agent can bind to TCR, CD83, CD3 and combinations thereof on the second cell.

In the methods, kits and uses of the invention, the method can detect binding of an MHC class I or MHC class II peptide to TCR, CD83, CD3 and combinations thereof.

In the methods, kits and uses of the invention, the first cell can be a lymphocyte, preferably wherein the first cell can be a T-cell.

In the methods, kits and uses of the invention, the second cell can be a non-lymphocyte cell, preferably wherein the second cell can be an antigen presenting cell.

In the methods, kits and uses of the invention, the interaction between PD-1 on a first lymphocyte cell and PD-L1 or PD-L2 on a second non-lymphocyte cell can be detected.

In the methods, kits and uses of the invention, the interaction between CTLA-4 or CD28 on a first lymphocyte cell and CD80 or CD86 on a second non-lymphocyte cell can be detected.

In the methods, kits and uses of the invention, the interaction between an MHC Class I or II peptide on a first lymphocyte cell and TCR, CD8, CD3 and combinations thereof on a second non-lymphocyte cell can be detected.

In the methods, kits and uses of the invention, the first secondary binding agent can be an anti-murine binding agent and the at least one other secondary binding agent can be an anti-rabbit binding agent.

In the methods, kits and uses of the invention, the FRET donor can be selected from the group consisting of ORG 488, GFP, fluorescein, IAEDANS, EDANS, BODIPY FL, ATTO488 and combinations thereof.

In the methods, kits and uses of the invention, the FRET acceptor can be selected from the group consisting of: ALX 594, mRFP, tetramethylrhodamine, fluorescein, dabcyl, BODIPY FL, QSY 7, QSY 9 and combinations thereof.

In the methods, kits and uses of the invention, the enzyme can be selected from the group consisting of oxidoreductases, hydrolases, lyases, transferases, isomerases, and ligases.

In the methods, kits and uses of the invention, the enzyme can be selected from the group consisting of peroxidases, oxidases, phosphatases, esterases and glycosidases.

In the methods, kits and uses of the invention, the enzyme can be selected from the group consisting of horseradish peroxidase, glucose oxidase, alkaline phosphatase and beta-galactosidase.

In the methods, kits and uses of the invention, the substrate can be tyramide.

In the methods, kits and uses of the invention, the first cell can be a T-cell and the second cell can be a tumour cell.

In the methods, kits and uses of the invention, the at least two primary binding agents can be contacted simultaneously or sequentially to one another.

In the methods, kits and uses of the invention, the at least two secondary binding agents can be contacted simultaneously or sequentially to one another.

In the methods, kits and uses of the invention, the at least two primary binding agents can be contacted with the sample simultaneously to the at least two secondary antibodies.

In the methods, kits and uses of the invention, the at least two primary binding agents can be contacted with the sample before the at least two secondary binding agents.

In the methods, kits and uses of the invention, a wash step can be performed after the at least two primary binding agents are contacted with the sample and before the at least two secondary binding agents are contacted with the sample.

In the methods, kits and uses of the invention, the method can further comprise the step of quantifying the interaction between the first site on the first cell and the second site on the second cell.

In the methods, kits and uses of the invention, the first cell can be a lymphocyte and the second cell can be a non-lymphocyte cell type.

In the methods, kits and uses of the invention, the method can detect the interaction between PD-1 on a first lymphocyte cell and PD-L1 or PD-L2 on a second non-lymphocyte cell.

In the methods, kits and uses of the invention, the first molecule can be located on the cell surface of the first cell and the second molecule can be located on the cell surface of the second cell.

In the methods, kits and uses of the invention, the at least two primary binding agents can bind to the first molecule or second molecule in such a manner that the checkpoint inhibitor or activator can bind to the first molecule or second molecule at the same time or subsequently.

In some methods, kits and uses of the invention, the at least two primary binding agents do not inhibit the binding of a checkpoint inhibitor or activator to the first molecule or the second molecule.

The present invention also provides the use of the aforementioned in vitro methods for detecting the interaction between a first molecule expressed on a first cell and a second molecule expressed on a second cell.

The present invention further provides a kit for use in an in vitro method for detecting cell-cell interactions, the kit comprising:
  a) at least two primary binding agents, wherein the first primary binding agent binds to the first molecule on the first cell and the second primary binding agent binds to the second molecule on the second cell, and wherein the first and secondary primary binding agents are immunologically distinct;
  b) at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary antibody; and wherein:
    (i) the first secondary binding agent is labelled with a FRET donor and the second secondary binding agent is labelled with a FRET acceptor;
    (ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
    (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;
  c) instructions for performing a method comprising:
    i. contacting an isolated sample containing cells with the at least two primary binding agents;
    ii. contacting the sample with the at least two secondary binding agents;
    iii. performing a wash step;
    iv. detecting the interaction between the secondary binding agents.

In the kits of the invention, the instructions for detecting the interaction between the secondary binding agents can be for detection by detecting the emitted fluorescence.

In the kits of the invention, the instructions for detecting the interaction between the secondary binding agents can be for detection by detecting the altered fluorescence behaviour.

In the kits of the invention, detecting the altered fluorescence behaviour can be time-resolved.

In the kits of the invention, the first cell and the second cell can be the same type of cell.

In the kits of the invention, the first cell and the second cell can be different types of cell i.e. not the same type of cell. In the kits of the invention, the isolated sample can be a fixed cell sample.

In the kits of the invention, the isolated sample can be fixed tumour cell sample.

In the kits of the invention, the first and second molecules can be proteins, preferably endogenous proteins. Preferably, the proteins are immune checkpoint proteins.

In the kits of the invention, the first molecule can be PD-1 and the second molecule can be PD-L1 or PD-L2.

In the kits of the invention, the first molecule can be CTLA-4 or CD28 and the second molecule can be CD80 or CD86.

In the kits of the invention, the first molecule can be an MHC Class I or II peptide and the second molecule can be selected from TCR, CD8, CD3 and combinations thereof.

In the kits of the invention, the at least two primary binding agents can be selected from the group consisting of whole immunoglobulins, antibody scaffolds, antibody or antigen-binding fragments thereof or combinations thereof.

In the kits of the invention, the at least two secondary binding agents can be selected from the group consisting of whole immunoglobulins, antibody scaffolds or antibody or antigen-binding fragments thereof or combinations thereof.

In the kits of the invention, at least one of the secondary binding agents can be an antibody scaffold, antibody or antigen-binding fragment. In the methods, kits and uses of the invention, the at least two secondary binding agents can be antibody scaffolds, antibody binding fragments or antigen-binding fragments.

In the kits of the invention, the antibody or antigen-binding fragments can Fab fragments, scFv fragments or combinations thereof.

In the kits of the invention, the antibody scaffolds can be adnectins, affibodies, affilins, anticalins, atrimers, avimers, bicyclic peptides, centyrins, cys-knots, DARPins, fynomers, Kunitz domains, Obodies, and Tn3s.

In the kits of the invention, the primary binding agents can be unlabelled.

In the kits of the invention, the first primary binding agent can be a murine binding agent and the at least one other primary binding agent can be a rabbit binding agent.

In the kits of the invention, the first primary binding agent can bind to PD-1 and the at least one other primary binding agent can bind to PD-L1 or PD-L2.

In the kits of the invention, the first primary binding agent can bind to CTLA-4 or CD28 and the second primary binding agent can bind to either CD80 or CD86.

In the kits of the invention, the first primary binding agent can bind to an MHC Class I or II peptide and the second primary binding agent can bind to TCR, CD8, CD3 and combinations thereof.

In the kits of the invention, the first secondary binding agent can be an anti-murine binding agent and the at least one other binding agent binding agent can be an anti-rabbit binding agent.

In the kits of the invention, the FRET donor can be selected from the group consisting of ORG 488, GFP, fluorescein, IAEDANS, EDANS, BODIPY FL, ATTO488 and combinations thereof.

In the kits of the invention, the FRET acceptor can be selected from the group consisting of: ALX 594, mRFP, tetramethylrhodamine, fluorescein, dabcyl, BODIPY FL, QSY 7, QSY 9 and combinations thereof.

In the kits of the invention, the enzyme can selected from the group consisting of oxidoreductases, hydrolases, lyases, transferases, isomerases, and ligases.

In the kits of the invention, the enzyme can be selected from the group consisting of peroxidases, oxidases, phosphatases, esterases and glycosidases. Preferably, the enzyme can be selected from the group consisting of horseradish peroxidase, glucose oxidase, alkaline phosphatase and beta-galactosidase.

In the kits of the invention, the substrate can be tyramide.

In the kits of the invention, the first cell is a T-cell and the second cell is a tumour cell.

In the kits of the invention, the instructions can provide for contacting the at least two primary binding agents simultaneously or sequentially to one another.

In the kits of the invention, the instructions can provide for contacting the at least two secondary binding agents simultaneously or sequentially to one another.

In the kits of the invention, the instructions can provide for contacting the at least two primary binding agents with the sample simultaneously to the at least two secondary binding agents.

In the kits of the invention, the instructions can provide for contacting the at least two primary binding agents with the sample before the at least two secondary binding agents.

In the kits of the invention, the instructions can provide for performing a wash step after the at least two primary binding agents are contacted with the sample and before the at least two secondary binding agents are contacted with the sample.

In the kits of the invention, the instructions provide a method further comprising the step of quantifying the interaction between the first site on the first cell and the second site on the second cell.

In the kits of the invention, the first cell can be a lymphocyte and the second cell can be a non-lymphocyte cell type.

In the kits of the invention, the instructions can provide for a method that detects the interaction between PD-1 on the first lymphocyte cell and PD-L1 or PD-L2 on the second non-lymphocyte cell.

In the kits of the invention, the first molecule can be located on the cell surface of the first cell and the second molecule can be located on the cell surface of the second cell.

In the kits of the invention, the at least two primary binding agents can bind to the first molecule or second molecule in such a manner that the checkpoint inhibitor or activator can bind to the first molecule or second molecule at the same time or subsequently.

In some aspects of the kits of the invention, the at least two primary binding agents do not inhibit the binding of an inhibitor or activator to the first molecule or the second molecule.

The present invention also provides use of the aforementioned kits of the invention in an in vitro method for detecting cell-cell interactions.

Preferably the use of the kits is in an in vitro coincidence assay method for detecting the interaction between a first molecule expressed on a first cell and a second molecule expressed on a second cell.

The present invention further provides a method of selecting a patient with cancer for treatment, the method comprising:

at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;

at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:

(i) the first secondary binding agent is labelled with a FRET donor and the second secondary binding agent is labelled with a FRET acceptor;

(ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:

(a) contacting an isolated tumour cell sample from the patient with the at least two primary binding agents;

(b) contacting the sample with the at least two secondary binding agents;

(c) performing a wash step;

(d) detecting the interaction between the secondary binding agents by determining the overall fluorescence score; wherein:

a. where the intended therapy comprises a checkpoint activator targeting at least one of the first and second checkpoint target molecules:

i. if the overall score is less than or equal to a threshold score, the overall score indicates or predicts that the patient will respond to the intended therapy; or ii. if the overall score is greater than a threshold score, the overall score indicates or predicts that the patient will not respond to the intended therapy; or b. where the intended therapy comprises a checkpoint inhibitor targeting at least one of the first and second checkpoint target molecules:
   (i) if the overall score is less than or equal to a threshold score, the overall score indicates or predicts that the patient will not respond to the intended therapy; or
   (ii) if the overall score is greater than a threshold score, the overall score indicates or predicts that the patient will respond to the intended therapy.

In the methods of the invention, the first checkpoint target molecule can be PD-1 and the second checkpoint target molecule can be PD-L1, and wherein in determining the fluorescence signal score:
   (i) if the overall score is less than or equal to a threshold score, the overall score indicates or predicts that the patient will not respond to treatment with an anti-PD-1, anti-PD-1:L1 or anti-PD-L2 binding agent; or
   (ii) if the overall score is greater than a threshold score, the overall score indicates or predicts that the patient will respond to treatment with an anti-PD-1, anti-PD-1:L1 or anti-PD-L2 binding agent.

In the methods of the invention, the first checkpoint target molecule can be CTLA-4 or CD28 and the second checkpoint target molecule can be CD80 or CD86, and wherein determining the fluorescence signal score:
   (i) if the overall score is less than or equal to a threshold score, the overall score indicates or predicts that the patient will not respond to treatment with an anti-CTLA-4/CD28 binding agent or an anti-CD80/86 binding agent; or
   (ii) if the overall score is greater than a threshold score, the overall score indicates or predicts that the patient will respond to treatment with an anti-CTLA-4/CD28 binding agent or an anti-CD80/86 binding agent.

In the methods of the invention, the first checkpoint target molecule can be an MHC Class I or II peptide and the second checkpoint target molecule can be TCR, CD8, CD3 and combinations thereof, and wherein determining the fluorescence signal score:
   (i) if the overall score is less than or equal to a threshold score, the overall score indicates or predicts that the patient will respond to treatment with an anti-MHC Class I or II binding agent or an anti-TCR/CD8/CD3 binding agent; or
   (ii) if the overall score is greater than a threshold score, the overall score indicates or predicts that the patient will not respond to treatment with an anti-MHC Class I or II binding agent or an anti-TCR/CD8/CD3 binding agent.

In some aspects of the methods of the invention, the patient has not previously received cancer therapy or the patient has not previously received a therapy targeting at least one of the checkpoint target molecules.

In the methods of the invention, if the overall score is 0.5% to 5%, this can indicate the patient will not respond to a therapy targeting at least one of the checkpoint target molecules.

In the methods of the invention, if the overall score is 5% to 10%, this can indicate the patient may respond to a therapy targeting at least one of the checkpoint target molecules.

In the methods of the invention, if the overall score is greater than 10%, this can indicate the patient will respond to a therapy targeting at least one of the checkpoint target molecules.

In the methods of the invention, if the overall score is 0.5% to 5%, this can indicate the patient will respond to a therapy targeting the MHC Class I/II-TCR/CD8/CD3 interaction.

In the methods of the invention, if the overall score is 5% to 10%, this can indicate the patient may respond to a therapy targeting the MHC Class I/II-TCR/CD8/CD3 interaction.

In the methods of the invention, if the overall score is greater than 10%, this can indicate the patient will not respond to a therapy targeting the MHC Class I/II-TCR/CD8/CD3 interaction.

In the methods of the invention, the overall score can be the percentage FRET efficiency.

In the methods of the invention, the at least two primary binding agents can bind to the first molecule or second molecule in such a manner that the checkpoint inhibitor or activator can bind to the first molecule or second molecule at the same time or subsequently.

In some aspects of the methods of the invention, the at least two primary binding agents do not inhibit the binding of the checkpoint inhibitor or activator to the first molecule or the second molecule.

The present invention also provides for the use of the aforementioned methods of the invention in selecting a patient with cancer for treatment, wherein:
   a. where the intended therapy comprises a checkpoint activator targeting at least one of the first and second checkpoint target molecules:
      i. if the overall score is less than or equal to a threshold score, the overall score indicates or predicts that the patient will respond to the intended therapy; or
      ii. if the overall score is greater than a threshold score, the overall score indicates or predicts that the patient will not respond to the intended therapy; or
   b. where the intended therapy comprises a checkpoint inhibitor targeting at least one of the first and second checkpoint target molecules:
      i. if the overall score is less than or equal to a threshold score, the overall score indicates or predicts that the patient will not respond to the intended therapy; or
      ii. if the overall score is greater than a threshold score, the overall score indicates or predicts that the patient will respond to the intended therapy.

The present invention further provides an in vitro coincidence assay method for detecting whether a checkpoint activator or inhibitor is effective in inhibiting or modulating a tumour response, the method comprising:
   at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;
   at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary antibody; and wherein:
      (i) the first secondary binding agent is labelled with a FRET donor and the second secondary binding agent is labelled with a FRET acceptor;

(ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(a) contacting an isolated tumour cell sample with the at least two primary binding agents;
(b) contacting the sample with the at least two secondary binding agents; (c) performing a wash step;
(d) detecting the interaction between the secondary binding agents by determining the overall fluorescence score;
(e) contacting the sample with the checkpoint activator or inhibitor;
(f) detecting any change in the interaction between the secondary binding agents, wherein:
   a. where the checkpoint molecule is an inhibitor:
      i. if the overall score decreases between steps (d) and (f) it is indicated or predicted that the checkpoint inhibitor is effective; or
      ii. if the overall score is unchanged between steps (d) and (f) it is indicated or predicted that the checkpoint inhibitor is not effective; or
   b. where the checkpoint molecule is an activator:
      i. if the overall score increases between steps (d) and (f) it is indicated or predicted that the checkpoint activator is effective; or
      ii. if the overall score is unchanged between steps (d) and (f) it is indicated or predicted that the checkpoint activator is not effective.

In the methods of the invention, the checkpoint inhibitor can be an anti-PD-1 binding agent, and the first primary binding agent can bind to PD-1 and the second primary binding agent can bind to PD-L1 or PD-L2.

In the methods of the invention, the checkpoint inhibitor can be an anti-CTLA-4 or CD28 binding agent, and the first primary binding agent can bind to CTLA-4 or CD28 and the second primary binding agent can bind to CD80 or CD86.

In the methods of the invention, the checkpoint activator can be an anti-MHC class I or II binding agent, and the first primary binding agent can bind to MHC class I or II and the second primary binding agent can bind to TCR, CD8, CD3 and combinations thereof. In the methods of the invention, the checkpoint inhibitor can be selected from the group consisting of ipilimumab, nivolumab (BMS-936558, DX 1106 or ONO-4538), pembrolizumab (iambrolizumab or MK-3475), pidilizumab (CT-Q1 1), ED-0680 (AMP-514), AMP-224, BMS-936559 (MDX-1 105), ED 4736, MPDL3280A (RG7448), MSB0010718C, and fragments and salts thereof.

In the methods of the invention, an overall score increase between steps (d) and (f) of 0.5% to 5%, preferably 5% to 10%, more preferably greater than 10%, can indicate that the checkpoint activator will be effective.

In the methods of the invention, an overall score decrease between steps (d) and (f) of 0.5% to 5%, preferably 5% to 10%, more preferably greater than 10%, can indicate that the checkpoint inhibitor will be effective.

In the methods of the invention, the at least two primary binding agents can bind to the first molecule or second molecule in such a manner that the checkpoint inhibitor or activator can bind to the first molecule or second molecule at the same time or subsequently.

In some aspects of the methods of the invention, the at least two primary binding agents do not inhibit the binding of the checkpoint inhibitor or activator to the first molecule or the second molecule.

The invention also provides for the use of the aforementioned in vitro coincidence assay methods of the invention for detecting whether a checkpoint inhibitor or activator will be effective in inhibiting or modulating a tumour response, wherein:
   a. where the checkpoint molecule is an inhibitor:
      i. if the overall score decreases between steps (d) and (f) it is indicated or predicted that the checkpoint inhibitor is effective; or
      ii. if the overall score is unchanged between steps (d) and (f) it is indicated or predicted that the checkpoint inhibitor is not effective; or
   b. where the checkpoint molecule is an activator:
      i. if the overall score increases between steps (d) and (f) it is indicated or predicted that the checkpoint activator is effective; or
      ii. if the overall score is unchanged between steps (d) and (f) it is indicated or predicted that the checkpoint activator is not effective.

The present invention further provides a kit for use in an in vitro coincidence assay method for detecting whether a checkpoint inhibitor or activator is effective in inhibiting or modulating a tumour response, the kit comprising:
(a) at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;
(b) at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
   (i) the first secondary binding agent is labelled with a FRET donor and the second secondary binding agent is labelled with a FRET acceptor;
   (ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
   (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

(c) instructions for performing a method comprising:
  a. contacting an isolated tumour cell sample with the at least two primary binding agents;
  b. contacting the sample with the at least two secondary binding agents;
  c. performing a wash step;
  d. detecting the interaction between the secondary binding agents by determining the overall fluorescence score;
  e. contacting the sample with the checkpoint activator or inhibitor;
  f. detecting any change in the interaction between the secondary binding agents, wherein:
  where the checkpoint molecule is an inhibitor:
    i. if the overall score decreases between steps (d) and (f) it is indicated or predicted that the checkpoint inhibitor is effective; or
    ii. if the overall score is unchanged between steps (d) and (f) it is indicated or predicted that the checkpoint inhibitor is not effective; or
  where the checkpoint molecule is an activator:
    iii. if the overall score increases between steps (d) and (f) it is indicated or predicted that the checkpoint activator is effective; or
    iv. if the overall score is unchanged between steps (d) and (f) it is indicated or predicted that the checkpoint activator is not effective.

In the kits of the invention, the instructions for detecting the interaction between the secondary binding agents can be for detection by detecting the emitted fluorescence.

In the kits of the invention, the instructions for detecting the interaction between the secondary binding agents can be for detection by detecting the altered fluorescence behaviour.

In the kits of the invention, detecting the altered fluorescence behaviour can be time-resolved.

In the kits of the invention, the first cell and the second cell can be the same type of cell.

In the kits of the invention, the first cell and the second cell can be different types of cell i.e. not the same type of cell. In the kits of the invention, the isolated sample can be a fixed cell sample.

In the kits of the invention, the isolated sample can be fixed tumour cell sample.

In the kits of the invention, the first and second molecules can be proteins, preferably endogenous proteins. Preferably, the proteins are immune checkpoint proteins.

In the kits of the invention, the first molecule can be PD-1 and the second molecule can be PD-L1 or PD-L2.

In the kits of the invention, the first molecule can be CTLA-4 or CD28 and the second molecule can be CD80 or CD86.

In the kits of the invention, the first molecule can be an MHC Class I or II peptide and the second molecule can be selected from TCR, CD8, CD3 and combinations thereof.

In the kits of the invention, the at least two primary binding agents can be selected from the group consisting of whole immunoglobulins, antibody scaffolds, antibody or antigen-binding fragments thereof or combinations thereof.

In the kits of the invention, the at least two secondary binding agents can be selected from the group consisting of whole immunoglobulins, antibody scaffolds or antibody or antigen-binding fragments thereof or combinations thereof.

In the kits of the invention, at least one of the secondary binding agents can be an antibody scaffold, antibody or antigen-binding fragment. In the methods, kits and uses of the invention, the at least two secondary binding agents can be antibody scaffolds, antibody binding fragments or antigen-binding fragments.

In the kits of the invention, the antibody or antigen-binding fragments can Fab fragments, scFv fragments or combinations thereof.

In the kits of the invention, the antibody scaffolds can be adnectins, affibodies, affilins, anticalins, atrimers, avimers, bicyclic peptides, centyrins, cys-knots, DARPins, fynomers, Kunitz domains, Obodies, and Tn3s.

In the kits of the invention, the primary binding agents can be unlabelled.

In the kits of the invention, the first primary binding agent can be a murine binding agent and the at least one other primary binding agent can be a rabbit binding agent.

In the kits of the invention, the first primary binding agent can bind to PD-1 and the at least one other primary binding agent can bind to PD-L1 or PD-L2.

In the kits of the invention, the first primary binding agent can bind to CTLA-4 or CD28 and the second primary binding agent can bind to either CD80 or CD86.

In the kits of the invention, the first primary binding agent can bind to an MHC Class I or II peptide and the second primary binding agent can bind to TCR, CD8, CD3 and combinations thereof.

In the kits of the invention, the first secondary binding agent can be an anti-murine binding agent and the at least one other secondary binding agent can be an anti-rabbit binding agent.

In the kits of the invention, the FRET donor can be selected from the group consisting of ORG 488, GFP, fluorescein, IAEDANS, EDANS, BODIPY FL, ATTO488 and combinations thereof.

In the kits of the invention, the FRET acceptor can be selected from the group consisting of: ALX 594, mRFP, tetramethylrhodamine, fluorescein, dabcyl, BODIPY FL, QSY 7, QSY 9 and combinations thereof.

In the kits of the invention, the enzyme can selected from the group consisting of oxidoreductases, hydrolases, lyases, transferases, isomerases, and ligases.

In the kits of the invention, the enzyme can be selected from the group consisting of peroxidases, oxidases, phosphatases, esterases and glycosidases. Preferably, the enzyme can be selected from the group consisting of horseradish peroxidase, glucose oxidase, alkaline phosphatase and beta-galactosidase.

In the kits of the invention, the substrate can be tyramide.

In the kits of the invention, the first cell is a T-cell and the second cell is a tumour cell.

In the kits of the invention, the instructions can provide for contacting the at least two primary binding agents simultaneously or sequentially to one another.

In the kits of the invention, the instructions can provide for contacting the at least two secondary binding agents simultaneously or sequentially to one another.

In the kits of the invention, the instructions can provide for contacting the at least two primary binding agents with the sample simultaneously to the at least two secondary binding agents.

In the kits of the invention, the instructions can provide for contacting the at least two primary binding agents with the sample before the at least two secondary binding agents.

In the kits of the invention, the instructions can provide for performing a wash step after the at least two primary binding agents are contacted with the sample and before the at least two secondary binding agents are contacted with the sample.

In the kits of the invention, the instructions provide a method further comprising the step of quantifying the interaction between the first site on the first cell and the second site on the second cell.

In the kits of the invention, the first cell can be a lymphocyte and the second cell can be a non-lymphocyte cell type.

In the kits of the invention, the instructions can provide for a method that detects the interaction between PD-1 on the first lymphocyte cell and PD-L1 or PD-L2 on the second non-lymphocyte cell.

In the kits of the invention, the instructions can provide for a method that detects the interaction between CTLA-4 or CD28 on the first lymphocyte cell and CD80 or 86 on the second non-lymphocyte cell.

In the kits of the invention, the instructions can provide for a method that detects the interaction between an MHC Class I or II peptide on the first lymphocyte cell and TCR, CD8, CD3 and combinations thereof on the second non-lymphocyte cell.

In the kits of the invention, the first molecule can be located on the cell surface of the first cell and the second molecule can be located on the cell surface of the second cell.

In the kits of the invention, the at least two primary binding agents can bind to the first molecule or second molecule in such a manner that the checkpoint inhibitor or activator can bind to the first molecule or second molecule at the same time or subsequently.

In some aspects of the kits of the invention, the at least two primary binding agents do not inhibit the binding of an inhibitor or activator to the first molecule or the second molecule.

The invention also provides for the use of the aforementioned kits of the invention in an in vitro coincidence assay method for detecting whether a checkpoint inhibitor or activator is effective in inhibiting or modulating a tumour response, wherein:
where the checkpoint molecule is an inhibitor:
i. if the overall score decreases between steps (d) and (f) it is indicated or predicted that the checkpoint inhibitor is effective; or
ii. if the overall score is unchanged between steps (d) and (f) it is indicated or predicted that the checkpoint inhibitor is not effective; or
where the checkpoint molecule is an activator:
iii. if the overall score increases between steps (d) and (f) it is indicated or predicted that the checkpoint activator is effective; or
iv. if the overall score is unchanged between steps (d) and (f) it is indicated or predicted that the checkpoint activator is not effective.

The present invention further provides an in vitro method of determining whether a therapy comprising a checkpoint activator or inhibitor is effective in a patient, the method comprising:
at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;
at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
(iv) the first secondary binding agent is labelled with a FRET donor and the second secondary binding agent is labelled with a FRET acceptor;
(v) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
(vi) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;
wherein the method comprises:
(a) contacting an isolated tumour cell sample obtained from the patient prior to the treatment comprising the checkpoint activator or inhibitor with at least two primary binding agents;
(b) contacting the sample with the at least two secondary binding agents;
(c) performing a wash step;
(d) detecting the interaction between the secondary binding agents by determining the overall fluorescence score;
(e) repeating steps (a) to (d) using an isolated tumour cell sample obtained from the patient during treatment comprising the checkpoint activator or inhibitor in step (a);
(f) comparing the overall fluorescence scores between the samples, wherein:
a. where the therapy comprises a checkpoint inhibitor:
i. if the overall score decreases, it is indicated or predicted that the therapy is effective; or
ii. if the overall score is unchanged, it is indicated or predicted that the therapy is not effective; or
b. where the therapy comprises a checkpoint activator:
i. if the overall score increases, it is indicated or predicted that the therapy is effective; or
ii. if the overall score is unchanged, it is indicated or predicted that the therapy is not effective.

In the methods of the invention, the checkpoint inhibitor can be an anti-PD-1 or PD-L1 binding agent, and the first primary binding agent can bind to PD-1 and the second primary binding agent can bind to PD-L1 or PD-L2. The first and second primary agents may not be the same as the checkpoint inhibitor and may not bind the same epitope as the checkpoint inhibitor.

In the methods of the invention, the checkpoint inhibitor can be an anti-CTLA-4 or CD28 binding agent, and the first primary binding agent can bind to CTLA-4 or CD28 and the second primary binding agent can bind to CD80 or CD86.

In the methods of the invention, the checkpoint inhibitor can be selected from the group consisting of nivoiumab (BMS-936558, DX 1106 or ONO-4538), pembroiizumab (iambroiizumab or MK-3475), pidilizumab (CT-Q1 1), ED-0680 (AMP-514), AMP-224, BMS-936559 (MDX-1 105), ED 4736, MPDL3280A (RG7448), MSB0010718C, and fragments and salts thereof.

In the methods of the invention, an overall score increase of 0.5% to 5%, preferably 5% to 10%, more preferably greater than 10%, can indicate that the therapy comprising a checkpoint activator will be effective.

In the methods of the invention, an overall score decrease of 0.5% to 5%, preferably 5% to 10%, more preferably greater than 10%, can indicate that the therapy comprising a checkpoint inhibitor will be effective.

In the methods of the invention, the at least two primary binding agents can bind to the first molecule or second molecule in such a manner that the checkpoint inhibitor or activator can bind to the first molecule or second molecule at the same time or subsequently.

In some aspects of the methods of the invention, the at least two primary binding agents do not inhibit the binding of the checkpoint inhibitor or activator to the first molecule or the second molecule.

The present invention also provides for the use of the aforementioned methods of the invention for determining whether a therapy comprising a checkpoint activator or inhibitor is effective in a patient, wherein:
a. where the therapy comprises a checkpoint inhibitor:
 i. if the overall score decreases, it is indicated or predicted that the therapy is effective; or
 ii. if the overall score is unchanged, it is indicated or predicted that the therapy is not effective; or
b. where the therapy comprises a checkpoint activator:
 i. if the overall score increases, it is indicated or predicted that the therapy is effective; or
 ii. if the overall score is unchanged, it is indicated or predicted that the therapy is not effective.

The present invention further provides a kit for use in an in vitro method of determining whether a therapy comprising a checkpoint activator or inhibitor is effective in a patient, the kit comprising:
at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;
at least two secondary binding agents, wherein a first secondary binding agent binds to the first primary binding agent; and a second secondary binding agent binds the second primary binding agent, wherein the first secondary binding agent does not bind the second primary binding agent and the second secondary binding does not bind the first primary binding agent; and wherein:
 (i) the first secondary binding agent is labelled with a FRET donor and the second secondary binding agent is labelled with a FRET acceptor;
 (ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
 (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

instructions for performing a method comprising:
 (a) contacting an isolated tumour cell sample obtained from the patient prior to the treatment comprising the checkpoint activator or inhibitor with the at least two primary binding agents;
 (b) contacting the sample with the at least two secondary binding agents;
 (c) performing a wash step;
 (d) detecting the interaction between the secondary binding agents by determining the overall fluorescence score;
 (e) repeating steps (a) to (d) using an isolated tumour cell sample obtained from the patient during treatment comprising the checkpoint activator or inhibitor in step (a);
 (f) comparing the overall fluorescence scores between the samples, wherein:
  a. where the therapy comprises a checkpoint inhibitor:
   i. if the overall score decreases, it is indicated or predicted that the therapy is effective; or
   ii. if the overall score is unchanged, it is indicated or predicted that the therapy is not effective; or
  b. where the therapy comprises a checkpoint activator:
   i. if the overall score increases, it is indicated or predicted that the therapy is effective; or
   ii. if the overall score is unchanged, it is indicated or predicted that the therapy is not effective.

The present invention also provides for the use of the aforementioned kits of the invention in an in vitro method of determining whether a therapy comprising a checkpoint activator or inhibitor has is effective in a patient, wherein:
a. where the therapy comprises a checkpoint inhibitor:
 i. if the overall score decreases, it is indicated or predicted that the therapy is effective; or
 ii. if the overall score is unchanged, it is indicated or predicted that the therapy is not effective; or
b. where the therapy comprises a checkpoint activator:
 i. if the overall score increases, it is indicated or predicted that the therapy is effective; or
 ii. if the overall score is unchanged, it is indicated or predicted that the therapy is not effective.

The present invention further provides an in vitro coincidence assay method for identifying whether a molecule of interest is a checkpoint activator or a checkpoint inhibitor, the method comprising:
at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;
at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
 (i) the first secondary binding agent is labelled with a FRET donor and the second secondary binding agent is labelled with a FRET acceptor;
 (ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
(iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(a) contacting an isolated tumour cell sample with the at least two primary binding agents;
(b) contacting the sample with the at least two secondary binding agents;
(c) performing a wash step;
(d) detecting the interaction between the secondary binding agents by determining the overall fluorescence score;
(e) contacting the sample with the molecule of interest;
(f) detecting any change in the interaction between the secondary binding agents, wherein:
  a. the molecule is a checkpoint activator for at least one of the first and second checkpoint target molecules if the overall score increases between steps (d) and (f); or
  b. the molecule is a checkpoint inhibitor for at least one of the first and second checkpoint target molecules if the overall score is decreases between steps (d) and (f); or
  c. the molecule is neither a checkpoint activator nor inhibitor for at least one of the first and second checkpoint target molecules if the overall score is unchanged between steps (d) and (f).

In the methods of the invention, an overall score increase between steps (d) and (f) of 0.5% to 5%, preferably 5% to 10%, more preferably greater than 10%, can indicate that the molecule of interest is a checkpoint activator for at least one of the first and second checkpoint target molecules.

In the methods of the invention, an overall score decrease between steps (d) and (f) of 5% to 0.5%, preferably 10% to 5%, more preferably greater than 10%, can indicate that the molecule of interest is a checkpoint inhibitor for at least one of the first and second checkpoint target molecules.

In the methods of the invention, the at least two primary binding agents can bind to the first molecule or second molecule in such a manner that the molecule of interest can bind to the first molecule or second molecule at the same time or subsequently.

In some aspects of the methods of the invention, the at least two primary binding agents do not inhibit the binding of the molecule of interest to the first molecule or the second molecule.

The present invention also provides an in vitro method of determining whether a patient with cancer will be responsive to an agent that blocks the PD-1:PD-L1/PD-L2 pathway, the method comprising:
at least two primary binding agents, wherein a first primary binding agent binds to PD-1 on the first cell and a second primary binding agent binds to PD-L1 or PD-L2 on the second cell, and wherein the first and secondary primary binding agents are immunologically distinct; and
at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
(i) the first secondary binding agent is labelled with a FRET donor and the second secondary binding agent is labelled with a FRET acceptor;
(ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
(iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

the method comprising:
(a) contacting an isolated tumour cell sample obtained from the patient with the at least two primary binding agents;
(b) contacting the sample with the at least two secondary binding agents;
(c) performing a wash step;
(d) detecting the interaction between the secondary binding agents by determining the overall fluorescence signal score, wherein:
  (i) if the overall score is less than or equal to a threshold score, the overall score indicates or predicts that the patient will not respond to treatment with an agent that blocks the PD-1:PD-L1/PD-L2 pathway; or
  (ii) if the overall score is greater than a threshold score, the overall score indicates or predicts that the patient will respond to treatment with an agent that blocks the PD-1:PD-L1/PD-L2 pathway.

In the methods of the present invention, the sample can be a fixed tumour cell sample.

In the methods of the present invention, the method can be performed:
(i) on a biological sample obtained from the patient prior to treatment to guide the decision on selection of treatment with a single agent that blocks the PD-1:PD-L1/PD-L2 pathway, or with an agent that blocks the PD-1:PD-L1/PD-L2 pathway and at least one other anti-tumour agent in a combination therapy; and
(ii) on at least one biological sample obtained from the patient during treatment to monitor response of the subject to the current treatment regimen and to guide decision on selection of treatment with a single-agent PD-1:PD-L1/PD-L2 blockade therapy or with a combination therapy.

The present invention also provides for the use of the aforementioned in vitro methods of the invention for determining whether a patient with cancer will be responsive to an agent that blocks the PD-1:PD-L1/PD-L2 pathway, wherein:
(i) if the overall score is less than or equal to a threshold score, the overall score indicates or predicts that the patient will not respond to treatment with an agent that blocks the PD-1:PD-L1/PD-L2 pathway; or
(ii) if the overall score is greater than a threshold score, the overall score indicates or predicts that the patient will respond to treatment with an agent that blocks the PD-1:PD-L1/PD-L2 pathway.

The present invention further provides a kit for use in an in vitro method of determining whether a patient with cancer will be responsive to an agent that blocks the PD-1:PD-L1/PD-L2 pathway, the kit comprising:

at least two primary binding agents, wherein the first primary binding agent binds to PD-1 on the first cell and the second primary binding agent binds to PD-L1 or PD-L2 on the second cell, and wherein the first and secondary primary binding agent s are immunologically distinct; and at least two secondary binding agents, wherein the first secondary binding agent binds to the first primary binding agent; and the second secondary binding agent binds the second primary binding agent, wherein the first secondary binding agent does not bind the second primary binding agent and the second secondary binding agent does not bind the first primary binding agent; and wherein:
(i) the first secondary binding agent is labelled with a FRET donor and the second secondary binding agent is labelled with a FRET acceptor;
(ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
(iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme; and instructions for performing a method comprising:
a. contacting an isolated tumour cell sample obtained from the patient with the at least two primary binding agents;
b. contacting the sample with the at least two secondary binding agents;
c. performing a wash step;
d. detecting the interaction between the secondary binding agents by determining the overall fluorescence signal score, wherein:
(i) if the overall score is less than or equal to a threshold score, the overall score indicates or predicts that the patient will not respond to treatment with an agent that blocks the PD-1:PD-L1/PD-L2 pathway; or
(ii) if the overall score is greater than a threshold score, the overall score indicates or predicts that the patient will respond to treatment with an agent that blocks the PD-1:PD-L1/PD-L2 pathway.

In the kits of the invention, the sample can be a fixed tumour cell sample.

In the kits of the invention, the instructions for performing the method can further comprise instructions to perform the method:
(i) on a biological sample obtained from the patient prior to treatment to guide the decision on selection of treatment with a single agent that blocks the PD-1:PD-L1/PD-L2 pathway, or with an agent that blocks the PD-1:PD-L1/PD-L2 pathway and at least one other anti-tumour agent in a combination therapy; and
(ii) on at least one biological sample obtained from the patient during treatment to monitor response of the subject to the current treatment regimen and to guide decision on selection of treatment with a single-agent PD-1:PD-L1/PD-L2 blockade therapy or with a combination therapy.

The present invention also provides for the use of the aforementioned kits of the invention in an in vitro method of determining whether a patient with cancer will be responsive to an agent that blocks the PD-1:PD-L1/PD-L2 pathway, wherein:
(i) if the overall score is less than or equal to a threshold score, the overall score indicates or predicts that the patient will not respond to treatment with an agent that blocks the PD-1:PD-L1/PD-L2 pathway; or
(ii) if the overall score is greater than a threshold score, the overall score indicates or predicts that the patient will respond to treatment with an agent that blocks the PD-1:PD-L1/PD-L2 pathway.

The present invention further provides an in vitro coincidence assay method for detecting the interaction between a first molecule expressed on a first cell and a second molecule expressed on a second cell, the method comprising:

a first and second fusion protein, wherein each fusion protein comprises a detection domain, a recognition domain and a connector domain;

the detection domain comprises a DNA binding domain and is capable of binding a cognate specific nucleotide sequence in co-operation with a further detection domain;

the recognition domain is capable of binding a target molecule;

the connector domain is fused at one end to the detection domain and fused at the other end to the recognition domain;

the detection domain, recognition domain and connector domain are heterologous to one another;

the method comprising the steps of:
(i) contacting the sample with the first and fusion proteins;
(ii) incubating to allow binding;
(iii) removing unbound fusion protein;
(iv) contacting the sample with nucleic acid comprising the cognate specific nucleotide sequence;
(v) incubating to allow heterotrimeric binding of the nucleic acid; and
(vi) detecting nucleic acid bound to the sample;
wherein, if the nucleic acid is detected in step (vi), this indicates that the two target molecules are present coincidentally in the sample.

In the methods, kits and uses of the invention, detecting the interaction between the secondary binding agents can be by detecting the emitted fluorescence.

In the methods, kits and uses of the invention, detecting the interaction between the secondary binding agents can be by detecting the altered fluorescence behaviour. Preferably, detecting the altered fluorescence behaviour is time-resolved.

In the methods, kits and uses of the invention, the first cell and the second cell can be the same type of cell.

In the methods, kits and uses of the invention, the first cell and the second cell can be different types of cell i.e. not the same type of cell.

In the methods, kits and uses of the invention, the isolated sample can be a fixed cell sample.

In the methods, kits and uses of the invention, the isolated sample can be a fixed tumour cell sample.

In the methods, kits and uses of the invention, the first and second molecules can be proteins, preferably endogenous proteins. Preferably, the proteins are immune checkpoint proteins.

In methods, kits and uses of the invention, the first molecule can be PD-1 and the second molecule can be PD-L1 or PD-L2.

In the methods, kits and uses of the invention the first molecule can be CTLA-4 or CD28 and the second molecule can be CD80 or CD86.

In the methods, kits and uses of the invention, the first molecule can be an MHC Class I or II peptide and the second molecule can be selected from TCR, CD8, CD3 and combinations thereof.

In the methods, kits and uses of the invention, the at least two secondary binding agents can be selected from the group consisting of whole immunoglobulins, antibody scaffolds or antibody or antigen-binding fragments thereof or combinations thereof.

In the methods, kits and uses of the invention, at least one of the secondary binding agents can be an antibody scaffold, antibody or antigen-binding fragment. In the methods, kits and uses of the invention, the at least two secondary binding agents can be antibody scaffolds, antibody binding fragments or antigen-binding fragments.

In the methods, kits and uses of the invention, the antibody or antigen-binding fragments can Fab fragments, scFv fragments or combinations thereof.

In the methods, kits and uses of the invention, the antibody scaffolds can be adnectins, affibodies, affilins, anticalins, atrimers, avimers, bicyclic peptides, centyrins, cysknots, DARPins, fynomers, Kunitz domains, Obodies, and Tn3s.

In the methods, kits and uses of the invention, the primary bindings agents can be unlabelled.

In the methods, kits and uses of the invention, the first primary bindings agent can be a murine binding agent and the at least one other primary bindings agent can be a rabbit binding agent.

In the methods, kits and uses of the invention, the first primary bindings agent can bind to PD-1 and the at least one other primary bindings agent can bind to PD-L1 or PD-L2.

In the methods, kits and uses of the invention, the first primary bindings agent can bind to CTLA-4 or CD28 and the second primary bindings agents can bind to either CD80 or CD86.

In the methods, kits and uses of the invention, the first primary bindings agents can bind to MHC Class I or II peptide and the at least one other primary bindings agent can bind to TCR, CD8, CD3 or a combination thereof.

In the methods, kits and uses of the invention, the first secondary bindings agent can be an anti-murine binding agent and the at least one other secondary bindings agent can be an anti-rabbit binding agent.

In the methods, kits and uses of the invention, the FRET donor can selected from the group consisting of ORG 488, GFP, fluorescein, IAEDANS, EDANS, BODIPY FL, ATTO488 and combinations thereof.

In the methods, kits and uses of the invention, the FRET acceptor can be selected from the group consisting of: ALX 594, mRFP, tetramethylrhodamine, fluorescein, dabcyl, BODIPY FL, QSY 7, QSY 9 and combinations thereof.

In the methods, kits and uses of the invention, the enzyme can be selected from the group consisting of oxidoreductases, hydrolases, lyases, transferases, isomerases, and ligases.

In the methods, kits and uses of the invention, the enzyme can be selected from the group consisting of peroxidases, oxidases, phosphatases, esterases and glycosidases.

In the methods, kits and uses of the invention, the enzyme can be selected from the group consisting of horseradish peroxidase, glucose oxidase, alkaline phosphatase and beta-galactosidase.

In the methods, kits and uses of the invention, the substrate can be tyramide.

In the methods, kits and uses of the invention, the first cell can be a T-cell and the second cell can be a tumour cell.

In the methods, kits and uses of the invention, the at least two primary bindings agents can be contacted simultaneously or sequentially to one another.

In the methods, kits and uses of the invention, the at least two secondary bindings agents can be contacted simultaneously or sequentially to one another.

In the methods, kits and uses of the invention, the at least two primary bindings agents can be contacted with the sample simultaneously to the at least two secondary bindings agents.

In the methods, kits and uses of the invention, the at least two primary bindings agents can be contacted with the sample before the at least two secondary bindings agents.

In the methods, kits and uses of the invention, a wash step can be performed after the at least two primary bindings agents are contacted with the sample and before the at least two secondary bindings agents are contacted with the sample.

In the methods, kits and uses of the invention, the method can further comprise the step of quantifying the interaction between the first site on the first cell and the second site on the second cell.

In the methods, kits and uses of the invention, the first cell can be a lymphocyte and the second cell can be a non-lymphocyte cell type.

In the methods, kits and uses of the invention, the method can detect the interaction between PD-1 on the first lymphocyte cell and PD-L1 or PD-L2 on the second non-lymphocyte cell.

In the methods, kits and uses of the invention, the first cell can be a lymphocyte and the second cell can be a non-lymphocyte cell type.

In the methods, kits and uses of the invention, the method can detect the interaction between CTLA-4 or CD28 on the first lymphocyte cell and CD80 or CD86 on the second non-lymphocyte cell.

In the methods, kits and uses of the invention, the first cell can be a lymphocyte and the second cell can be a non-lymphocyte cell type.

In the methods, kits and uses of the invention, the method can detect the interaction between an MHC Class I or II peptide on the first lymphocyte cell and TCR, CD8, CD3 or combinations thereof on the second non-lymphocyte cell.

In the methods, kits and uses of the invention, the first molecule can be located on the cell surface of the first cell and the second molecule can be located on the cell surface of the second cell.

In the methods, kits and uses of the invention, the at least two primary binding agents can bind to the first molecule or second molecule in such a manner that the checkpoint inhibitor or activator can bind to the first molecule or second molecule at the same time or subsequently.

In some methods, kits and uses of the invention, the at least two primary binding agents do not inhibit the binding of a checkpoint inhibitor or activator to the first molecule or the second molecule.

The skilled person would understand that the optional features outlined above can be applied in combination in the methods, uses and kits of the invention.

DESCRIPTION OF THE DRAWINGS

Non-limiting embodiments of the present invention will now further be described by way of reference to the figures, in which:

FIG. 2 shows variations in PD-1: PD-L1 interactions by TSA-FRET.

FIG. 4 shows PD-1 and PD-L1 interaction quantified by immune FRET (FRET).

FIG. 6 shows CTLA-4 and CD80 interaction quantified by immune FRET (iFRET).

FIG. 8 shows PD-1: PD-L1 interactions in primary renal cell carcinoma tissue.

FIG. 9 shows the use of an immune-Förster resonance energy transfer (i-FRET) assay for determining programmed death receptor-1 (PD-1) and programmed death-ligand 1 (PD-L1) interaction on clear cell renal cell carcinoma (ccRCC) tissue.

DETAILED DESCRIPTION OF INVENTION

Figure 1:
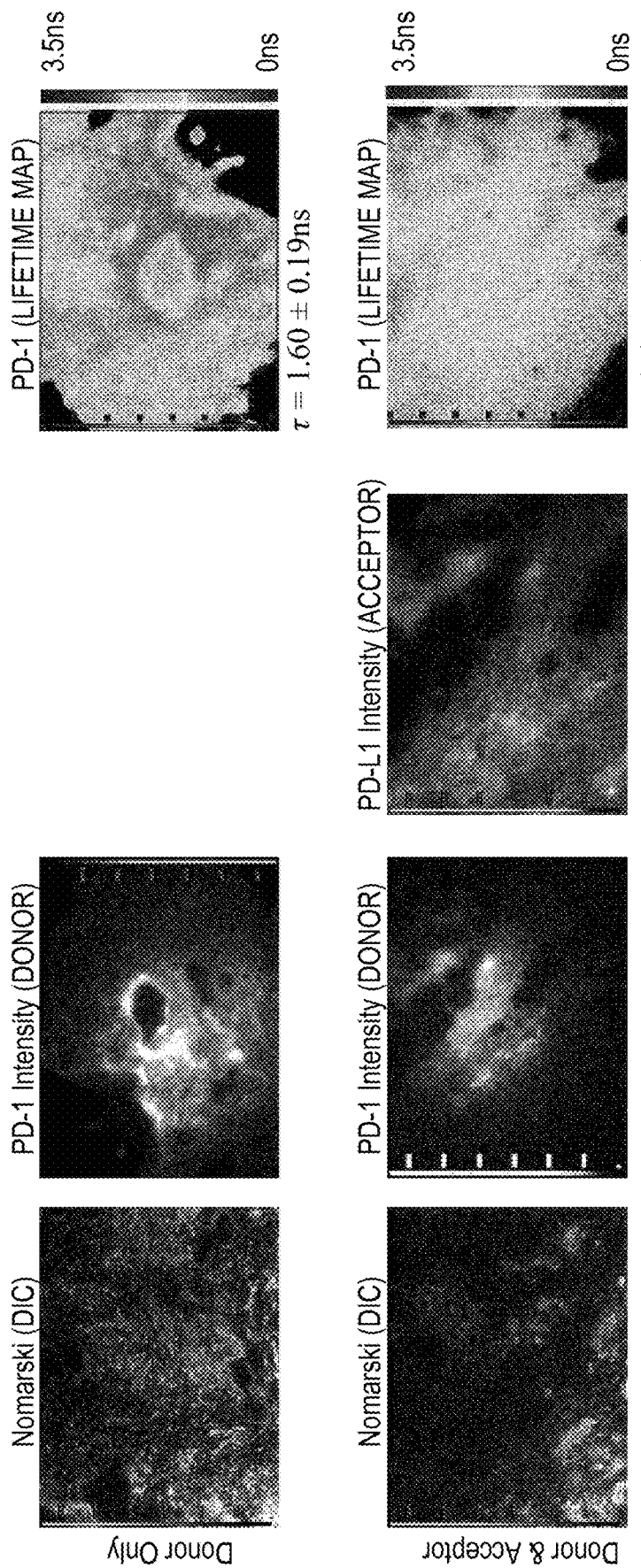
FIG. 1 shows variations in PD-1: PD-L1 interactions by TSA-FRET in patients treated with anti-RTK drugs and a binding agent blocking PD-1.

The present invention provides methods, kits and uses of coincidence assays, including FRET, FRET with amplification (e.g. TSA-FRET), proximity ligation and coincidence detection, in detecting interactions between molecules at the cellular level. In particular, the claimed invention provides, for the first time, for the detection and quantification of the interaction of two proteins, each on the cell surface of a different cell i.e. in trans. The present invention provides for the detection and/or quantification of the interaction between two proteins expressed on different cells.

The present invention provides an in vitro coincidence assay method for detecting the interaction between a first molecule expressed on a first cell and a second molecule expressed on a second cell, the method comprising:

at least two primary binding agents, wherein the first primary binding agent binds to the first molecule on the first cell and the second primary binding agent binds to the second molecule on the second cell, and wherein the first and secondary primary binding agents are immunologically distinct;

at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:

(i) the first secondary binding agent is labelled with a FRET donor and the second secondary binding agent is labelled with a FRET acceptor;

(ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(a) contacting an isolated sample containing cells with the at least two primary binding agents;
(b) contacting the sample with the at least two secondary binding agents;
(c) performing a wash step;
(d) detecting the interaction between the secondary binding agents.

The present invention also provides the use of the in vitro coincidence assay method above for detecting the interaction between a first molecule expressed on a first cell and a second molecule expressed on a second cell.

The invention further provides kits for use in the above in vitro assay methods for detecting the interaction between a first molecule expressed on a first cell and a second molecule expressed on a second cell.

The invention further provides methods of selecting a patient with cancer for treatment, the method comprising:

at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;

at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:

(i) the first secondary binding agent is labelled with a FRET donor and the second secondary binding agent is labelled with a FRET acceptor;

(ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(a) contacting an isolated tumour cell sample from the patient with the at least two primary binding agents;
(b) contacting the sample with the at least two secondary binding agents;
(c) performing a wash step;
(d) detecting the interaction between the secondary binding agents by determining the overall fluorescence score; wherein:
 a. where the intended therapy comprises a checkpoint activator targeting at least one of the first and second checkpoint target molecules:
  i. if the overall score is less than or equal to a threshold score, the overall score indicates or predicts that the patient will respond to the intended therapy; or
  ii. if the overall score is greater than a threshold score, the overall score indicates or predicts that the patient will not respond to the intended therapy; or
 b. where the intended therapy comprises a checkpoint inhibitor targeting at least one of the first and second checkpoint target molecules:
  (iii) if the overall score is less than or equal to a threshold score, the overall score indicates or predicts that the patient will not respond to the intended therapy; or
  (iv) if the overall score is greater than a threshold score, the overall score indicates or predicts that the patient will respond to the intended therapy.

The present invention also provides the use of the above in vitro coincidence assay methods for selecting a patient with cancer for treatment, and kits for use in this respect.

In additional aspects, the present invention provides in vitro coincidence assay methods for detecting whether a checkpoint activator or inhibitor is effective in inhibiting or modulating a tumour response, the method comprising:

at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;

at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
 (i) the first secondary binding agent is labelled with a FRET donor and the second secondary binding agent is labelled with a FRET acceptor;
 (ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
 (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(a) contacting an isolated tumour cell sample with the at least two primary binding agents;
(b) contacting the sample with the at least two secondary binding agents;
(c) performing a wash step;
(d) detecting the interaction between the secondary binding agents by determining the overall fluorescence score;
(e) contacting the sample with the checkpoint activator or inhibitor;
(f) detecting any change in the interaction between the secondary binding agents, wherein:
 a. where the checkpoint molecule is an inhibitor:
  i. if the overall score decreases between steps (d) and (f) it is indicated or predicted that the checkpoint inhibitor is effective; or
  ii. if the overall score is unchanged between steps (d) and (f) it is indicated or predicted that the checkpoint inhibitor is not effective; or
 b. where the checkpoint molecule is an activator:
  i. if the overall score increases between steps (d) and (f) it is indicated or predicted that the checkpoint activator is effective; or
  ii. if the overall score is unchanged between steps (d) and (f) it is indicated or predicted that the checkpoint activator is not effective.

The present invention also provides the use of the above in vitro coincidence assay methods for detecting whether a checkpoint activator or inhibitor is effective in inhibiting or modulating a tumour response, and kits for use in this respect.

In additional aspects, the present invention provides in vitro methods of determining whether a therapy comprising a checkpoint activator or inhibitor is effective in a patient, the method comprising:

at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;

at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
 (i) the first secondary binding agent is labelled with a FRET donor and the second secondary binding agent is labelled with a FRET acceptor;
 (ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(a) contacting an isolated tumour cell sample obtained from the patient prior to the treatment comprising the checkpoint activator or inhibitor with at least two primary binding agents;
(b) contacting the sample with the at least two secondary binding agents;
(c) performing a wash step;
(d) detecting the interaction between the secondary binding agents by determining the overall fluorescence score;
(e) repeating steps (a) to (d) using an isolated tumour cell sample obtained from the patient during treatment comprising the checkpoint activator or inhibitor in step (a);
(f) comparing the overall fluorescence scores between the samples, wherein:
  a. where the therapy comprises a checkpoint inhibitor:
    i. if the overall score decreases, it is indicated or predicted that the therapy is effective; or
    ii. if the overall score is unchanged, it is indicated or predicted that the therapy is not effective; or
  b. where the therapy comprises a checkpoint activator:
    i. if the overall score increases, it is indicated or predicted that the therapy is effective; or
    ii. if the overall score is unchanged, it is indicated or predicted that the therapy is not effective.

The present invention also provides the use of the above in vitro methods for determining whether a therapy comprising a checkpoint activator or inhibitor is effective in a patient, and kits for use in this respect.

The present invention further provides in vitro coincidence assay methods for identifying whether a molecule of interest is a checkpoint activator or a checkpoint inhibitor, the method comprising:
at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;
at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
(i) the first secondary binding agent is labelled with a FRET donor and the second secondary binding agent is labelled with a FRET acceptor;
(ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
(iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(a) contacting an isolated tumour cell sample with the at least two primary binding agents;
(b) contacting the sample with the at least two secondary binding agents;
(c) performing a wash step;
(d) detecting the interaction between the secondary binding agents by determining the overall fluorescence score;
(e) contacting the sample with the molecule of interest;
(f) detecting any change in the interaction between the secondary binding agents, wherein:
  a. the molecule is a checkpoint activator for at least one of the first and second checkpoint target molecules if the overall score increases between steps (d) and (f); or
  b. the molecule is a checkpoint inhibitor for at least one of the first and second checkpoint target molecules if the overall score is decreases between steps (d) and (f); or
  c. the molecule is neither a checkpoint activator or inhibitor for at least one of the first and second checkpoint target molecules if the overall score is unchanged between steps (d) and (f).

The present invention also provides the use of the above in vitro methods for identifying whether a molecule of interest is a checkpoint activator or a checkpoint inhibitor, and kits for use in this respect.

The present invention further provides in vitro methods of determining whether a patient with cancer will be responsive to an agent that blocks the PD-1:PD-L1/PD-L2 pathway, the method comprising:
at least two primary binding agents, wherein a first primary binding agent binds to PD-1 on the first cell and a second primary binding agent binds to PD-L1 or PD-L2 on the second cell, and wherein the first and secondary primary binding agents are immunologically distinct; and
at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
(i) the first secondary binding agent is labelled with a FRET donor and the second secondary binding agent is labelled with a FRET acceptor;
(ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
(iii) the first secondary binding agent is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme;
the method comprising:
(a) contacting an isolated tumour cell sample obtained from the patient with the at least two primary binding agents;
(b) contacting the sample with the at least two secondary binding agents;
(c) performing a wash step;
(d) detecting the interaction between the secondary binding agents by determining the overall fluorescence signal score, wherein:
(i) if the overall score is less than or equal to a threshold score, the overall score indicates or predicts that the patient will not respond to treatment with an agent that blocks the PD-1:PD-L1/PD-L2 pathway; or
(ii) if the overall score is greater than a threshold score, the overall score indicates or predicts that the patient will respond to treatment with an agent that blocks the PD-1:PD-L1/PD-L2 pathway.

The present invention also provides the use of the above in vitro methods for determining whether a patient with cancer will be responsive to an agent that blocks the PD-1:PD-L1/L2 pathway, and kits for use in this respect.

The present invention further provides in vitro coincidence assay methods for detecting the interaction between a first molecule expressed on a first cell and a second molecule expressed on a second cell, the method comprising:
a first and second fusion protein, wherein each fusion protein comprises a detection domain, a recognition domain and a connector domain;
the detection domain comprises a DNA binding domain and is capable of binding a cognate specific nucleotide sequence in co-operation with a further detection domain;
the recognition domain is capable of binding a target molecule; the connector domain is fused at one end to the detection domain and fused at the other end to the recognition domain;
the detection domain, recognition domain and connector domain are heterologous to one another;
the method comprising the steps of:
(i) contacting the sample with the first and second fusion proteins;
(ii) incubating to allow binding;
(iii) removing unbound fusion proteins;
(iv) contacting the sample with nucleic acid comprising the cognate specific nucleotide sequence;
(v) incubating to allow heterotrimeric binding of the nucleic acid; and
(vi) detecting nucleic acid bound to the sample;
wherein, if the nucleic acid is detected in step (vi), this indicates that the two target molecules are present coincidentally in the sample.

The methods and kits of the invention provide coincidence assays, including FRET, FRET with amplification (e.g. TSA-FRET), proximity ligation and coincidence detection, in detecting interactions between molecules at the cellular level.

The present invention also provides the use of the above in vitro methods for detecting the interaction between a first molecule expressed on a first cell and a second molecule expressed on a second cell, and kits for use in this respect.

The methods, kits and uses of the invention have the advantage of providing, for the first time, the detection and quantification of the interaction of two proteins, each on the cell surface of a different cell i.e. in trans, in a low cost, generic and robust methodology with an improved signal/noise ratio.

The novel uses of the invention can, in particular, be used to address the challenges of studying protein-protein interactions at the cellular level, preferably endogenous proteins, where the proteins are expressed on different cells, and serve in particular to allow the interaction between immune checkpoint inhibitors expressed on lymphocyte and non-lymphocyte cell types to be detected and quantified.

The present invention can thus lead to improved methods for identifying checkpoint inhibitor efficacy and for determining whether patient is likely to respond to a cancer therapy, such as, anti-PD-1, anti-PD-L1, anti-PD-L2, anti-CTLA-4, anti-CD28, anti-CD80, anti-CD86, anti-MHC Class I, anti-MHC Class II, anti-TCR, anti-CD8 and/or anti-CD3 therapy. The present invention also provides improved methods for stratifying patients towards response to cancer therapy, such as, anti-PD-1, anti-PD-L1, anti-PD-L2, anti-CTLA-4, anti-CD28, anti-CD80, anti-CD86, anti-MHC Class I, anti-MHC Class II, anti-TCR, anti-CD8 and/or anti-CD3 therapy, to aid with providing patients with more targeted cancer therapies.

Definitions

The present invention can employ the use of a variety of "coincidence assays", which enable the detection of two binding agents (e.g. antibodies) in close proximity. Exemplary coincidence assays of the present invention include Förster (fluorescence) resonance energy transfer (FRET), FRET with amplification (e.g. tyramide-signal amplification FRET (TSA-FRET)), proximity ligation assays (PLA), biomolecular fluorescence complementation (BiFC), enzyme fragment complementation and coincidence biodetection involving oligonucleotide capture using recombinant protein biodetectors produced in bacterial expression systems.

"Proximity ligation assay" refers to a coincidence assay that enables the detection of two binding agents in close proximity. Different antigens are detected by species-different primary binding agents, which are bound by species specific secondary binding agents covalently modified with circle forming oligonucleotides. The circle forming oligonucleotides can be ligated and used as a template for rolling circle amplification and fluorescence detection. Alternatively, the species-different primary binding agents can be directly ligated with circle forming oligonucleotides, which can be ligated and used as a template for rolling circle amplification and fluorescence detection. These methods can detect antibody distances up to about 40 nm. Preferably, theses method can detect antibody distances up to about 28 nm.

"Coincidence biodetection" refers to methods of detecting the coincidence of two target molecules. The method uses two fusion proteins, where each fusion protein comprises a detection domain, a recognition domain and a connector domain. The detection domain can comprise a DNA binding domain and is capable of binding a cognate specific nucleotide sequence in co-operation with a further detection domain. The recognition domain is capable of binding a target molecule. The connector domain is fused at one end to the detection domain and fused at the other end to the recognition domain. The detection domain, recognition domain and connector domain are heterologous to one another. The method involves the steps of (i) contacting the sample with the fusion proteins; (ii) incubating to allow binding; (iii) removing unbound fusion protein; (iv) contacting the sample with nucleic acid comprising the cognate specific nucleotide sequence; (v) incubating to allow heterotrimeric binding of the nucleic acid; and (vi) detecting nucleic acid bound to the sample. If the nucleic acid is detected in step (vi), this indicates that the two target molecules are present coincidentally in said sample. Such methods are disclosed in WO/2011/161420, which is incorporated herein by reference in its entirety.

Figure 10:
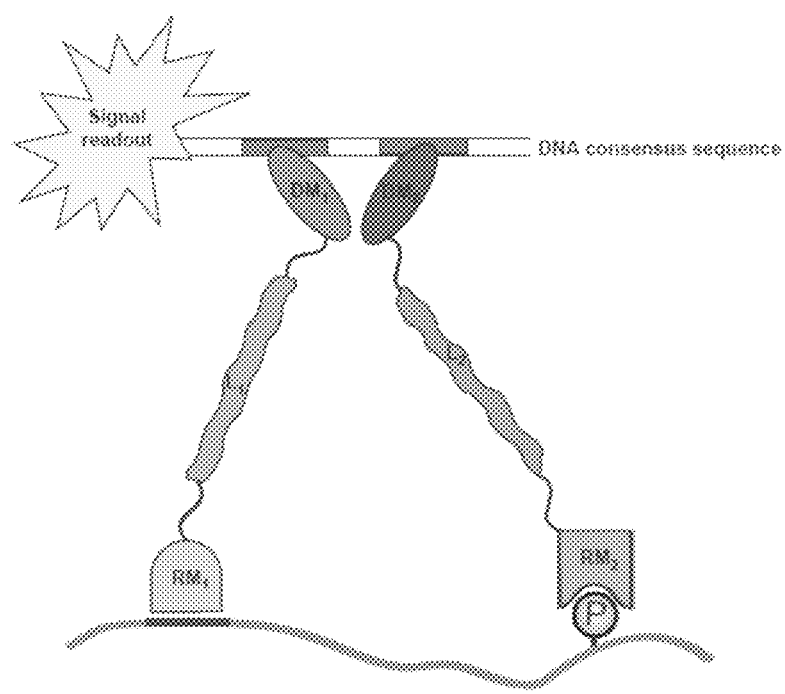
FIG. 10 shows the principles of coincidence biodetection.

More specifically, this refers to a coincidence binding assay where two distinct affinity probes (fusion proteins with recognition modules) bind two different sites/epitopes in two target proteins in close proximity. The method can use recombinant protein biodetectors produced in bacterial expression systems. The detection domains of the fusion proteins can form heterotrimeric complexes with their target double stranded DNA sequences (referred to as DNA consensus sequences). Recombinant fusion proteins can be used in the assay each comprising a detection module and a recognition module joined by a linker (connector domain). The linker can have a length between 5 nm and 40 nm. Preferably, the linker has a length between 5 nm and 30 nm, more preferably between 5 nm and 20 nm, or between 5 nm and 10 nm. The linker can also have a minimum length of 10 nm, 20 nm, or 30 nm or a maximum length of 40 nm, 30 nm, 20 nm or 10 nm. A signal is only generated when the detection domains simultaneously bind their DNA consensus sequence to form a heterotrimeric complex and the recognition domains bind their specific epitope targets in close proximity. The length of the linkers can be varied to modulate the distance between the target epitopes, as detailed above. FIG. 10 shows the principles of coincidence biodetection.

"Förster (fluorescence) resonance energy transfer (FRET)" can also be used in a coincidence assay that enables the detection of two binding agents (e.g. antibodies) in close proximity. FRET can be used by itself in the present methods or in combination with amplification, such as an enzyme activation system (e.g. tyramide signal amplification (TSA)).

FRET is a photophysical process in which energy is transferred from an excited FRET (donor) fluorophore to an adjacent FRET (acceptor) fluorophore via a non-radiative dipole-dipole interaction. The efficiency of energy transfer varies inversely with the sixth power of the distance, separating donor and acceptor fluorophores hence the distance over which FRET can occur is limited to 9 nm. Therefore, FRET is a "chemical ruler" used to measure molecular proximity.

Figure 11:
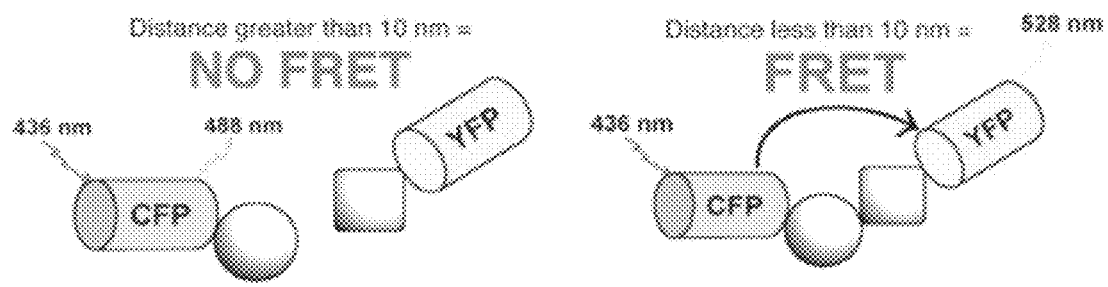
FIG. 11 shows the principles of Forster fluorescence resonance energy transfer (FRET).

FIG. 11 shows the principles of FRET.

FRET makes it possible to measure the interactions (association or dissociation) between two proteins in close proximity (<10 nm) that are labelled with a pair of fluorescence dyes.

"FRET donor" refers to a chromogenic or fluorogenic substrate that has shorter excitation/emission wavelengths than a FRET acceptor. In the above Figure, the FRET donor is cyan fluorescent protein (CFP).

"FRET acceptor" refers to a chromogenic or fluorogenic substrate that has longer excitation/emission wavelengths than a FRET donor. In the above Figure, the FRET acceptor is yellow fluorescent protein (YFP).

The donor chromophore (FRET donor) excites the acceptor molecule (FRET acceptor) when the emission spectrum of the donor and the excitation spectrum of the acceptor overlap. The FRET donor and FRET acceptor molecules need to be in close proximity (less than 10 nm). When the distance between the donor and acceptor is less than 10 nm, excitation of the acceptor occurs, providing a measurable fluorescent reporter signal. As well as detecting the reporter signal, it is possible to quantify the reporter signal. This approach can be used to determine the distance between the donor and acceptor chromophores. This approach can also be used to measure protein-protein interactions, protein-lipid interactions, protein-DNA interactions, and protein conformational changes, such as conformational and post-translational modification states of individual proteins.

The FRET efficiency (E) is the quantum yield of the energy transfer transition, i.e. the fraction of energy transfer event occurring per FRET donor excitation event:

$$E = \frac{k_{ET}}{k_f + k_{ET} + \sum k_i}$$

$$E = \frac{k_{ET}}{k_f + k_{ET} + \sum k_i}$$

where $k_{ET} k_{ET}$ is the rate of energy transfer, $k_f k_f$ the radiative decay rate and the $k_i k_i$ are the rate constants of any other de-excitation pathway.

The FRET efficiency depends on many physical parameters, including the distance between the donor and the acceptor, the spectral overlap of the FRET donor emission spectrum and the FRET acceptor absorption spectrum and the relative orientation of the FRET donor emission dipole moment and the FRET acceptor absorption dipole moment.

EE depends on the FRET donor-to-FRET acceptor separation distance rr with an inverse 6th power law due to the dipole-dipole coupling mechanism:

$$E = \frac{1}{1 + (r/R_0)^6}$$

$$E = \frac{1}{1 + (r/R_0)^6}$$

with $R_0 R_0$ being the Förster distance of this pair of FRET donor and FRET acceptor. This is the distance at which the energy transfer efficiency is about 50%.

Donors of the present invention include ORG 488, GFP, fluorescein, IAEDANS, EDANS, BODIPY FL and ATTO488.

Acceptors of the present invention include ALX 594, mRFP, fluorescein, tetramethylrhodamine, dabcyl, BODIPY FL and QSY 7 and QSY 9 dyes.

Combinations of the above donor and acceptor pairs are encompassed by the present invention.

Other exemplary donor—acceptor pairs include cyan fluorescent protein (CFP)—yellow fluorescent protein (YFP), YFP-CFP, ORG488-ALX594 and ATTO488-ALX594.

The donor and acceptor can be of two different types (hetero-FRET) or of the same type (homo-FRET). In the case of homo-FRET, spectral differences are not used to detect and measure FRET. Instead, differences in the anisotropy between the light which excites the donor and acceptor and the light which is emitted can be detected and measured. Exemplary methods for detecting homoFRET include FRET anisotropy imaging. The level of quantified anisotropy (the difference in polarisation between the excitation and emission beams) provides an indication of how many FRET events have occurred.

Table 1 below provides exemplary FRET donors and acceptor parings with their typical $R_0$ values:

| FRET Donor | FRET Acceptor | $R_0$ (Å) |
| --- | --- | --- |
| Fluorescein | Tetramethylrhodamine | 55 |
| IAEDANS | Fluorescein | 46 |
| EDANS | Dabcyl | 33 |
| Fluorescein | Fluorescein | 44 |
| BODIPY FL | BODIPY FL | 57 |
| Fluorescein | QSY 7 and QSY 9 dyes | 61 |

There are several ways of measuring the FRET efficiency by monitoring changes in the fluorescence emitted by the donor or the acceptor. These methods are well known to a person of skill in the art, such as sensitised emission, photobleaching FRET and lifetime measurements, and are encompassed with the present invention.

Exemplary uses for FRET include, determining the structure and conformation of proteins, determining the distribution and assembly of protein complexes, determining receptor/ligand interactions, immunoassays, enzymatic assays, probing interactions of single molecules, determining the structure and conformation of nucleic acids, real-time PCR assays and SNP detection, detecting nucleic acid hybridization, primer-extension assays for detecting mutations, automated DNA sequencing, determining the distribution and transport of lipids, membrane fusion assays, membrane potential sensing, indicators for cyclic AMP and calcium, and detecting and quantifying Akt activation in tumours, such as breast tumours.

"Coincidence FRET" or "two-site" FRET, describes the method of simultaneously labeling a single protein on two distinct sites with a donor and an acceptor pair, and detecting the FRET between them.

"Enzyme activation system" refers to an enzyme system where at least one enzyme is coupled, in any manner known to a person of skill in the art, to a member of a specific binding pair. For example, the enzyme can be conjugated or fused to the specific binding pair. In the present invention, the specific binding pair can be located on an antibody. In certain embodiments, the specific binding pair is located on an antibody selected from the first primary antibody, the second primary antibody, the first secondary antibody and the second secondary antibody and combinations thereof.

The enzyme, either by itself of or in connection with a second enzyme reacts with a conjugate comprising a detectably-labelled substrate, to form an activated conjugate. The activated conjugate binds to a receptor (e.g. electron rich moieties) on a molecular surface adjacent to the enzyme. The binding can be via covalent binding. The activated conjugate can be deposited wherever receptors (e.g. electron rich moieties) for the activated conjugate are found. The receptors (e.g. electron rich moieties) on the molecular surface are not reactive with the enzyme activation system. Therefore, the detectably-labelled substrate binds the receptors (e.g. electron rich moieties) only when the detectably-labelled substrate has been activated by the enzyme to form an activated conjugate. In the absence of the enzyme, the detectably-labelled substrate does not form an activated conjugate.

The detectably-labelled substrate of the conjugate can comprise one or more components. In one embodiment, the detectably-labelled substrate comprises one component containing the binding site for the receptor (e.g. electron rich moieties) and a detectable-label. In another embodiment, the substrate comprises two components; one component can contain the binding site for the receptor (e.g. electron rich moieties) and be detectably labelled. The other component can contain a constituent which prevents or interferes with binding to the receptors (e.g. electron rich moieties) until such a time as the enzyme activates the conjugate.

The term "detectably-labelled" means that the substrate is coupled either directly to a detectable label or indirectly to a detectable label.

The substrate can be detectably labelled using methods well known to a person of ordinary skill in the art.

In the case of indirect labelling, the substrate can be coupled to an unlabelled first member of a specific binding pair. Following activation and binding to the receptor (e.g. electron rich moieties) by the activated conjugate, the first member of the specific binding pair can be reacted with the second member of the specific binding pair, which is coupled to a detectable label. Alternatively, the first member of the specific binding pair can be pre-reacted with the second member of the specific binding pair, which is coupled to a reporter, prior to activation and binding of the receptor (e.g. electron rich moieties) by the activated conjugate.

In the present invention, the detectable label can comprise a FRET acceptor or a FRET donor. In preferred embodiments, the detectable label comprises a FRET acceptor. In some aspects of the present invention, the substrate comprises tyramide. In some embodiments, the detectably labelled substrate comprises tyramide labelled with a FRET donor. In preferred embodiments, the detectably labelled substrate comprises tyramide labelled with a FRET acceptor.

The enzyme can be selected from oxidoreductases, hydrolases, lyases, transferases, isomerases, ligases and combinations thereof. In certain embodiments, the enzyme is selected from peroxidases, oxidases, phosphatases, esterases, glycosidases and combinations thereof. In preferred embodiments, the enzyme is selected from horseradish peroxidase, glucose oxidase, alkaline phosphatase, beta-galactosidase and combinations thereof.

The term "activated conjugate" refers to a conjugate comprising a detectably labelled substrate that is specific for the enzyme activation system and has been activated by the enzyme of the system. Following activation, the activated conjugate can bind the receptors (e.g. electron rich moieties) on a molecular surface adjacent to the enzyme. A sample is subjected to reaction conditions sufficient to cause the enzyme to catalyse the activation of the substrate in order to form the activated conjugate.

The reaction conditions sufficient to cause the enzyme to catalyse the activation of the substrate are well known to a person of skill in the art. In the case of tyramide signal amplification (TSA), the enzyme employed is hydrogen peroxidase and the detectably-labelled substrate is detectably-labelled tyramide. The reactions conditions require the presence of hydrogen peroxide for hydrogen peroxidase to catalyse the activation of detectably-labelled tryamide to form an activated conjugate containing detectably-labelled tyramide radicals. In preferred embodiments, the detectable label is a FRET acceptor or a FRET donor. In particularly preferred embodiments, the detectable label is ALX594 or ORG488. In other preferred embodiments, the detectable label is ALX594 or ATTO488.

In preferred embodiments, the detectably-labelled substrate comprises tyramide labelled with a FRET acceptor and the enzyme (e.g. horseradish peroxidase) activates tyramide to form an activated conjugate comprising highly reactive, short-lived tyramide radicals coupled to the FRET acceptor, which radicals can covalently couple to electron rich moieties on a molecular surface adjacent to the enzyme. In preferred embodiments, the electron rich residues are tyrosine residues. The molecular surface can be a protein or nucleic acid sequence.

The term "amplification" refers to amplification of a reporter signal provided by the detectable label of the detectably-labelled substrate due to binding of conjugates comprising the detectably-labelled substrate that have been activated by the enzyme activation system to electron rich moieties on a molecular surface adjacent to the enzyme. In the present invention, the reporter signal can comprise fluorescence. In some embodiments, the reported signal comprises fluorescence emitted by a FRET acceptor or a FRET donor. In preferred embodiments, the reporter signal comprises fluorescence emitted by a FRET acceptor.

The enzyme activation system of the present invention can be applied to the first primary antibody, the second primary antibody, the first secondary antibody, the second secondary antibody or a combination thereof, provided that the system is applied to at least one of the first secondary antibody and the second secondary antibody.

"Adjacent to" in the context of the enzyme activation system refers to receptors located within close proximity to the enzyme. For example, the distance between the enzyme and receptors can be about 2 to 9 nm or less than a 100 kDa globular protein (preferably, 2 to 9 nm, 2 to 7 nm, 2 to 6 nm, 2 to 5 nm, 2 to 4 nm or 2 to 3 nm or less than 90 kDa, less than 80 kDa, less than 70 kDa, less than 60 kDa, less than 50 kDa, less than 40 kDa, less than 30 kDa, less than 20 kDa or less than 10 kDa).

One specific embodiment of a single enzyme activation system of the present invention is a tyramide signal amplification (TSA) system. The system utilises the catalytic activity of horseradish peroxididase, which activates reporter-coupled tyramide to form an activated conjugate comprising highly reactive, short-lived tyramide radicals, which radicals can covalently couple to tyrosine residues on a molecular surface adjacent to the horseradish peroxidase. The molecular surface can be a protein or nucleic acid residue.

In certain aspects, the cell sample is obtained from the patient prior to treatment or during treatment. "Obtained from the subject prior to treatment" can mean obtained from a patient that has been previously treated for cancer e.g. previously treated with an anti-tumour agent, or can mean obtained from a patient that has not previously been treated for cancer i.e. a treatment naïve patient.

In certain aspects, the "cell sample" is a tumour cell sample. The cell sample is preferably a fixed cell sample. The cell sample can be a tumour cell sample including the surrounding patient tissue (e.g. macrophages, T cells, B cells, etc.). The cell sample can be a tumour biopsy.

The term "tumour cells" includes cancer cells. This can include primary tumour cells, secondary (metastatic) tumour cells, solid tumours and the associated patient tissue (e.g. macrophages, T cells, B cells, etc.). The tumour sample can be, for example, a tumour biopsy or surgical incision obtained from the patient. Typically, the tumour sample comprises an invasive tumour margin. The tumour sample can be obtained from a metastatic lesion. The sample can comprise peripheral blood. The patient can be one who is suspected of having a metastatic cancer. Examples of cancer include, but are not limited to, melanoma, lung cancer, including for example non-small cell lung cancer, breast cancer, head and neck cancer, urothelial cancer. Further examples of cancer include adrenocortical carcinoma, anal cancer, bladder cancer, blood cancer, brain stem glioma, cerebellar astrocytoma, ependymoma, carcinoid tumour, carcinoma of unknown primary, cervical cancer, colon cancer, endometrial cancer, esophageal cancer, extrahepatic bile duct cancer, Ewings family of tumours (PNET), extracranial germ cell tumour, eye cancer, intraocular melanoma, gallbladder cancer, gastric cancer, germ ceil tumour, extragonadal, gestational trophoblastic tumor, hypopharyngeai cancer, islet cell carcinoma, kidney cancer (renal cell cancer), laryngeal cancer, acute lymphoblastic leukemia, acute myeloid leukemia, chronic lymphocytic leukemia, chronic myelogenous leukemia, hairy cell leukemia, lip and oral cavity cancer, liver cancer, small cell lung cancer, lymphoma, cutaneous T-cell lymphoma, Hodgkin's and non-Hodgkin's lymphoma, multiple myeloma and other plasma cell neoplasms, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell tumor, pancreatic cancer, islet cell carcinoma, paranasal sinus and nasal cavity cancer, parathyroid cancer, penile cancer, pituitary cancer, plasma cell neoplasm, prostate cancer, rhabdomyosarcoma, rectal cancer, renal cell cancer, salivary gland cancer, sezary syndrome, skin cancer, kaposi's sarcoma, melanoma, small intestine cancer, soft tissue sarcoma, stomach cancer, testicular cancer, thymoma, malignant, thyroid cancer, urethral cancer, uterine cancer, sarcoma, vaginal cancer, vulvar cancer, and Wilms' tumor.

The terms "anti-PD-1 antibody" or "anti-PD-L1 antibody" refer to an antibody that targets the programmed death 1 (PD-1) molecule or its ligands, PD-L1 and PD-L2, such as by disrupting interactions between PD-1 and PD-L1 or PD-L2, blocking activation of PD-1 independently of whether it is interacting with PD-L1 or PD-L2, or blocking PD-L1 or PD-L2 signaling pathways that are triggered upon PD-L1 or PD-L2 interacting with PD-1.

The terms "anti-PD-1" or "anti-PD-L1 therapy" mean a therapeutic strategy that targets the programmed death 1 (PD-1) molecule or its ligands, PD-L1 and PD-L2, such as by disrupting established, present interactions between PD-1 and PD-L1 or PD-L2, or blocking future interactions between PD-1 and PD-L1 or between PD-1 and PD-L2, blocking activation of PD-1 independently of whether it is interacting with PD-L1 or PD-L2, or blocking PD-L1 or PD-L2 signaling pathways that are triggered upon PD-L1 or PD-L2 interacting with PD-1. Examples of anti-PD-1 immunotherapeutic agents include, but are not limited to, pembrolizumab, nivolumab, and pidilizumab. Examples of anti-PD-L1 immunotherapeutic agents include, but are not limited to, BMS-936559 and atezoiizumab.

The terms "anti-CTLA-4" or "anti-CD80/86" mean a therapeutic strategy that targets the cytotoxic T-lymphocyte-associated protein 4 (CTLA-4) molecule or its ligands, CD80 or CD86, such as by disrupting interactions between CTLA-4 and CD80 or CD86, blocking activation of CTLA-4 independently of whether it is interacting with CD80 or CD86, or blocking CD80 or CD86 signaling pathways that are triggered upon CD80 or CD86 interacting with CTLA-4.

The terms "anti-CTLA-4 therapy" or "anti-CD80/86 therapy" mean a therapeutic strategy that targets the cytotoxic T-lymphocyte-associated protein 4 (CTLA-4) molecule or its ligands, CD80 and CD86, such as by disrupting established, present interactions between CTLA-4 and CD80 or CD86, or blocking future interactions between CTLA-4 and CD80 or between CTLA-4 and CD86, blocking activation of CTLA-4 independently of whether it is interacting with CD80 or CD86, or blocking CD80 or CD86 signaling pathways that are triggered upon CD80 or CD86 interacting with CTLA-4. Examples of anti-CTLA-4 immunotherapeutic agents include, but are not limited to ipilimumab.

The terms "anti-MHC class I", "anti-MHC class II" or "anti-TCR" mean a therapeutic strategy that targets the T-cell receptor (TCR) or its ligands MHC class I or MHC class II, such as by disrupting interactions between TCR and MHC class I or MHC class II, blocking activation of TCR independently of whether it is interacting with MHC class I or MHC class II, or blocking TCR signalling pathways that are triggered upon MHC class I or MHC class II interacting with TCR.

The terms "anti-TCR therapy", "anti-MHC class I therapy" or "anti-MHC class II therapy" mean a therapeutic strategy that targets the T-cell receptor molecule of its ligands MHC class I or MHC class II such as by disrupting established, present interactions between TCR and MHC class I or MHC class II, or blocking further interactions between TCR and MHC class I or MHC class II, blocking activation independently of whether it is interacting with MHC class I or MHC class II, or blocking MHC class I or MHC class II signalling pathways that are triggered upon MHC class I or MHC class II interacting with TCR.

"Treating" or "treatment" of a disease in a patient refers to (1) preventing the symptoms or disease from occurring in a human or animal that is does not yet display symptoms of the disease; (2) inhibiting the disease or arresting its progression; or (3) ameliorating or causing regression of the disease or the symptoms associated with the disease.

"Immunologically distinct" in the context of binding agents, refers to binding agents raised in different host species or different isotypes from the same species. In an embodiment of the present invention, the primary binding agents are a first and second antibodies wherein the first primary antibody is raised in a different host species to the second primary antibody or the first primary antibody is a first isotype from a species and the second primary antibody is a second isotype from the same species, where the first and second isotypes are different. Exemplary host species include, mouse, rat, rabbit, goat, camel, sheep or horse. For example, the first primary antibody can be raised in mouse and the second primary antibody can be raised in rabbit. This enables the first secondary binding agent to be a generic anti-mouse antibody (labelled with a donor) and the second secondary binding agent to be a generic anti-rabbit antibody (conjugated to an enzyme). This provides a generic, high throughput methodology. In a preferred embodiment, the first primary antibody is an anti-PD-1 mouse antibody and the second primary antibody is an anti-PD-L1 or PD-L2 rabbit antibody. In other preferred embodiments, the first primary antibody is an anti-CTLA-4 or CD28 mouse antibody and the second primary antibody is an anti-CD80 or CD86 rabbit antibody. In another preferred embodiment, the first primary antibody is an anti-MHC Class I or II mouse antibody and the second primary antibody is an anti-TCR, CD8, CD3 and/or combinations thereof rabbit antibody.

"Binding agent" refers to any molecule capable of binding another molecule and can necessarily include, but is not limited to, whole immunoglobulins, antibody scaffolds and antibody or antigen-binding fragments.

"Antibody" is used in the broadest sense and specifically encompasses whole immunoglobulins as well as antibody or antigen-binding fragments thereof, such as variable domains. Exemplary whole immunoglobulins include full-length and native antibodies, monoclonal antibodies (including full-length monoclonal antibodies), polyclonal antibodies, multispecific antibodies (e.g. bispecific antibodies), chimeric antibodies.

"Monoclonal antibody" refers to an antibody obtained from a population of substantially homogeneous antibodies; that is, the individual antibodies comprising the population are identical except for naturally occurring mutations that may be present in minor amounts. Monoclonal antibodies are highly specific, being directed against a single antigenic determinant, also referred to as an epitope. Monoclonal antibodies can be made by any technique or methodology known in the art including, hybridoma methods, recombinant DNA methods and isolation from phage antibody libraries.

In contrast, "polyclonal antibodies" are typically a heterogeneous population of immunoglobulin isotypes and/or classes and also exhibit a variety of epitope specificity.

"Chimeric antibody" refers to a type of monoclonal antibody in which a portion of or the complete amino acid sequence in one or more regions or domains of the heavy and/or light chain is identical with, homologous to, or a variant of the corresponding sequence in a monoclonal antibody from another species or belonging to another immunoglobulin class or isotype, or from a consensus sequence. Chimeric antibodies include fragments of such antibodies, provided that the antibody exhibits the desired biological activity of its parent antibody, for example binding to the same epitope.

"Antibody or antigen-binding fragment", refers to a portion of a full-length antibody in which a variable region or a functional capability of the parent antibody is retained, for example, specific epitope binding. The antibody or antigen-binding fragments of the invention have a conserved epitope in the constant region for secondary recognition. Examples of antibody fragments include, but are not limited to, a Fab, Fab', F(ab')$_2$, Fd, Fv, scFv and scFv-Fc fragments, diabody, triabody, tetrabody, linear antibody, single-chain antibody, and other multispecific antibodies formed from antibody fragments.

Antibody scaffold refers to a non-native antigen-binding protein, peptide, or antibody fragment. Antibody scaffolds include adnectins, affibodies, affilins, anticalins, atrimers, avimers, bicyclic peptides, centyrins, cys-knots, DARPins, fynomers, Kunitz domains, Obodies, and Tn3s.

"Fab fragment" refers to fragment-antigen binding fragment, which is a region on an antibody that binds to antigens. It is composed of one constant and one variable domain of each of the heavy and the light chain. These domains shape the antigen-binding site at the amino terminal end of the fragment. The two variable domains bind the epitope on their specific antigens. The Fab fragments of the invention have a conserved epitope in the constant region for secondary antibody recognition.

Methods of preparing Fab fragments are well known to the skilled person, for example, the enzyme papain can be used to cleave a whole immunoglobulin into two Fab fragments and an Fc fragment.

Fab fragments can be further cleaved to form F(ab')$_2$ and Fab' fragments, using methods known to the skilled person. For example, the enzyme pepsin can be used to cleave a Fab fragment below the hinge region to produce a F(ab')$_2$ fragment and a pFc' fragment. Alternatively, the enzyme IdeS (Immunoglobulin degrading enzyme from *Streptococcus pyogenes*, trade name FabRICATOR) can be used to cleave IgG in a sequence specific manner at neutral pH to produce F(ab')$_2$ fragments. F(ab')$_2$ fragments can be split into two Fab' fragments, for example, by mild reduction.

A "single-chain Fv" or "scFv" antibody fragment is a single chain Fv variant comprising the heavy chain variable domain ($V_H$) and the light chain variable domain ($V_L$) of an antibody, in which the domains are present in a single polypeptide chain and which is capable of recognising and binding antigen. The scFv fragments of the invention have a conserved epitope in the constant region for secondary antibody recognition. The scFv polypeptide optionally contains a polypeptide linker positioned between the $V_H$ and $V_L$ domains that enables the scFv to form a desired three-dimensional structure for antigen binding.

Methods for producing scFvs are well known to the skilled person. For example, separate $V_H$ and $V_L$ chains can be fused together. scFvs are approximately half the size of Fab fragments, yet retain the original specificity of the parent antibody.

"Diabody" refers to a small antibody fragment having two antigen-binding sites. Each fragment contains a $V_H$ domain concatenated to a $V_L$ to form a $V_H$-$V_L$ or $V_L$-$V_H$ polypeptide. By using a linker that is too short to allow pairing between the two domains on the same chain, the linked $V_H$-$V_L$ domains are forced to pair with complementary domains of another chain, creating two antigen-binding sites.

"Linear antibody" refers to antibodies that comprise a pair of tandem Fd segments ($V_H$-$C_H$1-$V_H$-$C_H$1) that form a pair of antigen binding regions. Linear antibodies can be bi-specific or mono-specific.

The antibodies, antibody scaffolds and antibody or antigen-binding fragments thereof of the invention can be tagged. In preferred embodiments, the tag is FLAG.

"Primary binding agent" refers to any molecule capable of binding another molecule and can necessarily include, but is not limited to, whole immunoglobulins, antibody scaffolds and antibody or antigen-binding fragments. For example the primary binding agent can be an antibody, antibody scaffold or an antibody or antigen-binding fragment thereof that binds to a first site on a molecule, such as a protein, DNA or a lipid. The primary binding agent has binding specificity for a site on a molecule. The first primary binding agent binds to a first site on a molecule, such as a protein.

In preferred embodiments, the first site is PD-1. The second primary binding agent binds to a second site on a molecule, such as a protein. In preferred embodiments, the second site is PD-L1.

In other preferred embodiments, the first site is CTLA-4 or CD28. The second primary binding agent binds to a second site on a molecule, such as a protein. In preferred embodiments, the second site is CD80 or CD86.

In another preferred embodiment, the first site is an anti-MHC Class I or II peptide. The second primary binding agent binds to a second site on a molecule, such as a protein. In preferred embodiments, the second site is TCR, CD8, CD3 and/or combinations thereof.

In preferred embodiments, the primary binding agents are unlabelled. In other embodiments, the primary binding agents can be labelled. For example, the label can be a tag, such as a FLAG tag.

In embodiments of the invention, the primary binding agents can be whole immunoglobulins, antibody scaffolds or antibody or antigen-binding fragments thereof. Combinations of the above are also envisaged. Preferred antibody fragments are Fab fragments or scFv fragments. For example, in methods of the invention, both the first primary antibody and the second primary antibody can be whole immunoglobulins. Alternatively, both the first primary antibody and the second primary antibody can be an antibody or antigen-binding fragment. In some embodiments, the first primary antibody and the second primary antibody are Fab fragments, scFv fragments or combinations thereof. Alternatively, the first primary can be a whole immunoglobulin and the second primary antibody can be an antibody or antigen-binding fragment or the second primary antibody can be an antibody or antigen-binding fragment and the second primary antibody can be a whole immunoglobulin. In some embodiments, the primary antibodies can be tagged (for example, with a FLAG tag) and the secondary antibodies can have a binding specificity for the tag (e.g. anti-FLAG).

"Secondary binding agent" refers to any molecule capable of binding another molecule and can necessarily include, but is not limited to, whole immunoglobulins, antibody scaffolds and antibody or antigen-binding fragments. For example, the secondary binding agent can be an antibody, an antibody scaffold or an antibody or antigen-binding fragment thereof that binds to a primary binding agent, such as the first or second primary binding agent, or a label on a primary binding agent, such as a FLAG tag.

In embodiments of the invention, the secondary binding agents can be whole immunoglobulins, antibody scaffolds or antibody or antigen-binding fragments thereof. Combinations of the above are also envisaged. Preferred antibody fragments are Fab fragments or scFv fragments. In particularly preferred embodiments, at least one secondary binding agent is an antibody, antibody scaffold or antigen-binding fragments. In preferred embodiments, both the first primary binding agents and the second primary binding agents are antibodies, antibody scaffolds or antigen-binding fragments. In some embodiments, the first secondary binding agent and the second secondary binding agent are Fab fragments, scFv fragments or combinations thereof. Alternatively, the first secondary binding agent can be an antibody, antibody scaffold or antigen-binding fragment and the second secondary binding agent can be a whole immunoglobulin or the first secondary binding agent can be a whole immunoglobulin and the second secondary binding agent can be an antibody, antibody scaffold or antigen-binding fragment. In some embodiments, the first secondary binding agent and the second secondary binding agent are not both whole immunoglobulins. The present invention was found not to work for some secondary binding agents where both were whole immunoglobulins, presumably because of conformational issues causing the FRET donor and FRET acceptors distances to be greater than required for FRET to occur (>10 nm). This was found to be the case regardless of the order of application of the primary and secondary binding agents.

In some embodiments, an enzyme is conjugated to or fused to a secondary binding agent. In preferred embodiments, the enzyme is conjugated to or fused to the second secondary binding agent. In embodiments where the second secondary binding agent is a scFv fragment, the scFv fragment can be recombinantly fused with the enzyme.

In the present invention, the first site is different from the second site to enable FRET to be detected between the different sites. In preferred embodiments, the first and second sites are on the same molecule. In particularly preferred embodiments, the first and second sites are on the same protein. In other embodiments, the first and second sites are on a different molecule, for example different proteins in a complex. Preferably, the proteins being detected in the isolated sample are endogenous proteins.

An "isolated" sample is a biological sample that has been isolated from a subject, for example, an isolated tumour sample. The biological sample can include organs, tissues, cells and/or fluids.

The term "subject" refers to any animal, particularly an animal classified as a mammal, including humans, domesticated and farm animals, and zoo, sports, or pet animals, such as dogs, horses, cats, cows, and the like. Preferably, the subject is human.

"Wash step" in the context of the present invention is used in its usual sense in immunohistochemistry to mean that the sample is washed with an acceptable solution, such as saline solution. For example, the wash step can be used to remove any unbound binding agent from a preceding step or to remove any detectably labelled substrate that has not been activated to form an activated conjugate.

"Checkpoint proteins" are known in the art. Under normal physiological conditions, immune checkpoints prevent autoimmunity and protect tissues from damage when the immune system is responding to pathogenic infection. The expression of checkpoint proteins can be dysregulated by tumours as part of the immune resistance mechanism. Immune checkpoint proteins can be activators or inhibitors of the immune checkpoint pathway, and can be used in the treatment of various cancers by providing an anti-tumour immune response or inflammatory diseases to enhance resolution of an immune response. In particular, checkpoint protein inhibition or activation can provide amplification of antigen-specific T cell responses. Exemplary checkpoint proteins include programmed cell death protein 1 (PD-1), PD-1 ligand (PD-L1), PD2 ligand (PD-L2), cytotoxic T-lymphocyte-associated antigen 4 (CTLA-4), B7 family proteins, TNF family proteins, CD40L, adenosine A2a receptor (A2aR), B7-related protein 1 (B7RP1), B and T lymphocyte attenuator (BTLA), galactin 9 (GAL9), herpesvirus entry mediator (HVEM), inducible T cell co-stimulator (ICOS), interleukin (IL), killer cell immunoglobulin-like receptor (KIR), lymphocyte activation gene 3 (LAG3), transforming growth factor-β (TGF-β), T cell membrane protein 3 (TIM3) and MHC Class I or II peptides. A preferred checkpoint target is PD-1. PD-L1 is also a preferred checkpoint target. CTLA-4 is a preferred checkpoint target. MHC Class I or II peptides are preferred checkpoint targets. LAG3, B7-H3, B7-H4 and TIM3 are also preferred checkpoint targets.

CTLA-4, PD-1, LAG3 and TIM3 are inhibitory receptors. PD-1, B7-H3 and B7-H4 are inhibitory ligands. All are undergoing clinical development for various cancer treatments.

CTLA-4 is expressed exclusively on T cells where it primarily regulates the amplitude of the early stages of T cell activation. Primarily, CTLA-4 counteracts the activity of the T cell co-stimulatory receptor, CD28. CD28 and CTLA-4 share the identical ligands CD80 (also known as B7.1) and CD86 (also known as B7.2).

PD-1 is an immune checkpoint receptor that limits the activity of T cells in peripheral tissues at the time of an inflammatory response to infection and limits autoimmunity. PD-1 expression is induced when T cells become activated. When engaged by one of its two ligands, PD-L1 or PD-L2 (B7 family members), PD-1 inhibits kinases that are involved in T cell activation. PD-L1 can also interact with CD80.

The B7 family of membrane-bound ligands binds both co-stimulatory and inhibitory receptors. All of the B7 family members and their known ligands belong to the immunoglobulin superfamily.

Tumour necrosis factor (TNF) family members that bind to cognate TNF receptor family molecules represent a second family of regulatory ligand-receptor pairs. These receptors predominantly deliver co-stimulatory signals when engaged by their cognate ligands.

Another major category of signals that regulate the activation of T cells comes from soluble cytokines in the microenvironment. Communication between T cells and APCs is bidirectional. In some cases, this occurs when ligands themselves signal to the APC. In other cases, activated T cells upregulate ligands, such as CD40L, that engage cognate receptors on APCs. A2aR, adenosine A2a receptor; B7RP1, B7-related protein 1; BTLA, B and T lymphocyte attenuator; GAL9, galectin 9; HVEM, herpesvirus entry mediator; ICOS, inducible T cell co-stimulator; IL, interleukin; KIR, killer cell immunoglobulin-like receptor; LAG3, lymphocyte activation gene 3; PD-1, programmed cell death protein 1; PDL, PD-1 ligand; TGFβ, transforming growth factor-β; TIM3, T cell membrane protein 3.

"Checkpoint target molecule" refers to a molecule, such as a protein, which is targeted by the coincidence assay methods of the invention. As explained above, "checkpoints" are immune checkpoints that prevent autoimmunity and protect tissues from damage when the immune system is responding to pathogenic infection. The expression of checkpoint proteins can be dysregulated by tumours as part of the immune resistance mechanism. Exemplary checkpoint target molecules include programmed cell death protein 1 (PD-1), PD-1 ligand (PD-L1), PD2 ligand (PD-L2), cytotoxic T-lymphocyte-associated antigen 4 (CTLA-4), B7 family proteins, TNF family proteins, CD40L, adenosine A2a receptor (A2aR), B7-related protein 1 (B7RP1), B and T lymphocyte attenuator (BTLA), galactin 9 (GAL9), herpesvirus entry mediator (HVEM), inducible T cell co-stimulator (ICOS), interleukin (IL), killer cell immunoglobulin-like receptor (KIR), lymphocyte activation gene 3 (LAG3), transforming growth factor-β (TGF-β), T cell membrane protein 3 (TIM3) and MHC Class I or II peptides. A preferred checkpoint target is PD-1. PD-L1 is also a preferred checkpoint target. CTLA-4 is a preferred checkpoint target. MHC Class I or II peptides are preferred checkpoint targets. LAG3, B7-H3, B7-H4 and TIM3 are also preferred checkpoint targets.

"Checkpoint activator" means a molecule, such as a protein, that activates the immune checkpoint pathway. Exemplary checkpoint activators include those from the TNF receptor and the B7-CD28 superfamilies, including CD40 (TNFSFR5) agonists, GITR (Glucocorticoid-Induced Tumor Necrosis Factor Receptor; TNFSFR18) stimulators, OX40 (CD134; TNFSFR4) agonists, 4-1BB (CD137; TNFSFR9) agonists, CD27 (TNFSFR7) agonists, ICOS (Inducible Co-Stimulator) molecule agonists, Trail receptor agonists and/or HVEM (Herpesvirus entry mediator) receptor agonists. Preferred checkpoint activators include OX-40, GITR and/or 4-1BB agonists.

"Checkpoint inhibitor" means a molecule, such as a protein, that inhibits the immune checkpoint pathway. Exemplary checkpoint inhibitors include anti-PD-1 binding agents, anti-PD-L1 binding agents, anti-PD-L2 binding agents, anti-CTLA-4 binding agents, anti-MHC Class I binding agents and/or anti-MHC Class II binding agents. An exemplary anti-CTLA-4 binding agent is ipilimumab. Exemplary anti-PD-1 binding agents include nivolumab (BMS-936558, DX 1106 or ONO-4538) and pembrolizumab (iambrolizumab or MK-3475).

Exemplary checkpoint inhibitors include those selected from the group comprising or consisting of ipilimumab, nivolumab (BMS-936558, DX 1106 or ONO-4538), pembrolizumab (iambrolizumab or MK-3475), pidilizumab (CT-Q1 1), ED-0680 (AMP-514), AMP-224, BMS-936559 (MDX-1 105), ED 4736, MPDL3280A (RG7448), MSB0010718C, and fragments and salts thereof.

METHODS OF THE INVENTION

The methods of the invention can be used in detecting and quantifying cell-cell interactions, particularly the interaction of two proteins, each on the cell surface of a different cell. Preferably, the proteins being detected in the isolated sample are endogenous proteins.

Advantageously, the methods and kits of the present invention can measure cell-cell interactions by quantitatively calculating the FRET by measuring the decrease of a donor chromophore lifetime in the presence of an acceptor chromophore. The present invention thus provides an average measure of the total amount of interaction between one molecule expressed on a first cell and a second molecule expressed on a second cell in a sample.

This leads to an improved dynamic range of measurable interactions, which is useful in a clinical setting to stratify cancer patients into groups to determine patients that will respond well to therapy and also to stratify the effectiveness of therapeutics, such as new therapeutics, that modulate the binding of one cell to another.

An exemplary use of the methods of the present invention is in examining the interaction of PD-1 and PD-L1 or PD-L2, which are immune checkpoint proteins identified as playing a part in tumour progression in a variety of cancers.

A further exemplary use of the methods of the present invention is in examining the interaction of CTLA-4 or CD28 and CD80 or CD86, which are also immune checkpoint proteins identified as playing a part in tumour progression in a variety of cancers.

A further exemplary use of the methods of the present invention is in examining the interaction of MHC-peptide (e.g. MHC Class I or Class II) with TCR (or CD8 or CD3). In particular, the methods of the present invention can be used in detecting and/or quantifying the interaction between a member of the TCR complex on T cells (e.g. TCR or CD8 or any member of the CD3 complex) and MHC Class I or Class II complexed with an antigenic peptide.

The methods of the present invention can also be used to examine the interaction between other immune checkpoint proteins, such as those exemplified herein.

The methods of the invention are sensitive, quantitative and allow determination of the localization of (altered) molecular pathways using conventional binding agents. Such methods aid in the detection of pharmacodynamic markers and facilitate the discovery/development of new small molecule inhibitors.

The methods of the invention preferably utilise coincidence assays.

The methods of the invention can be used in combination with detection by fluorescence lifetime imaging microscopy (FLIM). Time resolved FRET can provide such information in single cells.

Two-Site FRET without Amplification

In one aspect, the present invention uses two-site FRET without amplification.

In the two-site FRET without amplification methods of the invention, the methodology employs at least two primary binding agents that bind to different target molecules and that are immunologically distinct, and at least two secondary binding agents that bind their respective primary binding agents and are respectively labelled with a FRET donor and a FRET acceptor. In particular, the first primary binding agent binds to a first molecule (e.g. a checkpoint target protein) on a first cell and the second primary binding agent binds to a second molecule (e.g. another or a different checkpoint target protein) on a second cell, and the first and second primary binding agents are immunologically distinct. The first secondary binding agent is labelled with a FRET donor and binds to the first primary binding agent; and the second secondary binding agent is labelled with a FRET acceptor and binds the second primary binding agent, wherein the first secondary binding agent does not bind the second primary binding agent and the second secondary binding agent does not bind the first primary binding agent.

In embodiments where the FRET donor on the bound first secondary binding agent is in close enough proximity (less than or equal to 10 nm to the FRET acceptor on the second secondary binding agent, a positive FRET signal can be detected.

Where the FRET donor on the bound first secondary binding agent is not in close enough proximity (greater than 10 nm) to the FRET acceptor on the second secondary binding agent, the FRET signal will be reduced or absent.

Where either or both of the first and second molecules are not present in the sample, no FRET signal will be detected.

In one example, primary, whole immunoglobulins anti-PD-1 (mouse) and anti-PD-L1 (T308) (rabbit) are contacted with a fixed tumour cell sample from a cancer patient. Secondary, Fab fragments anti-mouse-ORG488 and anti-rabbit-ALX594 are contacted with the sample and bind the anti-PD-1 (mouse) and anti-PD-L1 (T308) (rabbit) antibodies, respectively. A positive FRET signal is generated between ORG488 and ALX594 where PD-1 and PD-L1 are in close proximity on the cell surface of different cells (less than or equal to 10 nm). The FRET signal can be detected in a time resolved manner by multiple frequency domain FLIM (mFD-FLIM).

Two-Site FRET with Amplification

In another aspect, the present invention provides a methodology employing at least two primary binding agents, at least two secondary binding agents and a conjugate (e.g. two-site FRET with amplification, such as two-site TSA-FRET).

The first primary binding agent binds to a first molecule (e.g. a checkpoint target protein) on a first cell and the second primary binding agent binds to a second molecule (e.g. another or a different checkpoint target protein) on a second cell, and the first and second primary binding agents are immunologically distinct.

The first secondary binding agent is labelled with a fluorescence resonance energy transfer (FRET) donor and binds to the first primary binding agent; and the second secondary binding agent is conjugated to an enzyme and binds the second primary binding agent, wherein the first secondary binding agent does not bind the second primary binding agent and the second secondary binding agent does not bind the first primary binding agent.

The conjugate comprises a FRET acceptor and a substrate specific for the enzyme, wherein when the substrate reacts with the enzyme, an activated conjugate, which activated conjugate binds to electron rich moieties on a molecular surface adjacent to the enzyme.

The methods of the present invention can comprise the steps of contacting a cell sample with the at least two primary binding agents, contacting the sample with the at least two secondary binding agents, performing a wash step, contacting the sample with the conjugate, and detecting any FRET signal generated by the FRET acceptor.

Using the methods of the invention, it is possible to detect a FRET signal if the first molecule and second molecule are in close spatial proximity (less than or equal to 9 nm), even if the first molecule and second molecule are expressed at low levels.

In the methods of the invention, the at least two primary binding agents are contacted with the cell sample. The at least two primary binding agents can be contacted with the sample at the same time as one another or sequentially to one another. Therefore, the first primary binding agent can be contacted with the sample first and then the second primary binding agent can be contacted with the sample. Alternatively, the second primary binding agent can be contacted with the sample first and then the second primary binding agent. When the first and second primary binding agents are contacted with the sample sequentially to one another, an optional wash step can be performed between the steps in the sequence.

The first primary binding agent binds to any first molecule on a first cell present in the sample and the second primary binding agent binds to any second molecule on a second cell present in the sample. The optional wash step removes any unbound primary binding agent.

The at least two secondary binding agents can be contacted with the cell sample at the same time as the at least two primary binding agents or the at least two primary binding agents can be contacted with the sample before the at least two secondary binding agents. The at least two secondary binding agents can be contacted with the sample at the same time as one another or sequentially to one another. Therefore, the first secondary binding agent can be contacted with the sample first and then the second secondary binding agent can be contacted with the sample. Alternatively, the second secondary binding agent can be contacted with the sample first and then the first secondary binding agent. When the first and second secondary binding agents are contacted with the sample sequentially to one another, an optional wash step can be performed between the steps in the sequence. In embodiments where the at least two primary binding agents are contacted with the sample before the at least two secondary binding agents, an optional wash step can be performed between administration of the at least two primary binding agents and the administration of the at least two secondary binding agents.

The first secondary binding agent binds to the first primary binding agent and the second primary binding agent binds to the second primary binding agent. The optional wash step removes any unbound secondary binding agent or any secondary binding agent that has bound to primary binding agent that has not bound the first or second site (i.e. unbound primary binding agent).

Following contact of the at least two primary binding agents and the at least two secondary binding agents with the sample, a wash step is performed before the conjugate is contacted with the sample. The wash step removes any binding agent (primary or secondary) that has not bound its target (e.g. the first site, second site, first primary binding agent or second primary binding agent). Saline solution or another suitable solution can be used to perform the wash steps in the methods of the invention. The conditions used in the wash step are well known to a person of ordinary skill in the art.

In some aspects, following the wash step, the conjugate is contacted with the sample. Where the second primary binding agent has bound the second molecule and the second secondary binding agent has bound the second primary binding agent, the substrate of the conjugate reacts with the enzyme conjugated to the second secondary binding agent to form an activated conjugate. The activated conjugate will binds to electron rich moieties on a molecular surface (e.g. a protein surface) adjacent to the enzyme. The enzyme can activate multiple conjugates, providing for the binding of multiple activated conjugates to electron rich moieties on a molecular surface adjacent to the enzyme. This amplifies the number of activated conjugates containing FRET acceptors that are bound in the vicinity of the second site.

Any FRET signal generated by the FRET acceptor is detected.

In embodiments where the FRET donor on the bound first secondary antibody is in close enough proximity (less than or equal to 10 nm) to the FRET acceptors on the bound activated conjugate, a positive FRET signal can be detected.

Where the FRET donor on the bound first secondary antibody is not in close enough proximity (greater than 10 nm) to the FRET acceptors on the bound activated conjugate, the FRET signal will be reduced or absent.

Where either or both of the first and second molecules are not present in the sample, no FRET signal will be detected.

In another aspect of the invention, the enzyme activation system can be applied to the first secondary binding agent in addition to the second secondary binding agent. This advantageously amplifies both the FRET donor signal and the FRET acceptor signal. In this aspect, the first secondary binding agent is conjugated to an enzyme in place of a FRET donor. The method further employs a second conjugate comprising a FRET donor and a substrate specific for the enzyme, wherein when the substrate reacts with the enzyme, a second activated conjugate forms, which second activated conjugate binds to electron rich moieties on a molecular surface adjacent to the enzyme. The substrate does not react with the enzyme conjugated to the second secondary binding agent.

The methods of the invention are adapted accordingly. For example, the method can comprise the steps of contacting a sample with the at least two primary binding agents, contacting the sample with the at least two secondary binding agents, performing a wash step, contacting the sample with a first conjugate specific for the enzyme conjugated to the first secondary binding agent and a second conjugate specific for the enzyme conjugated to the second secondary binding agent, and detecting any FRET signal generated by the FRET acceptor. The first conjugate can be applied simultaneously or sequentially to the second conjugate. For example, the first conjugate can be contacted with the sample first and then the second conjugate can be contacted with the sample. Alternatively, the second conjugate can be contacted with the sample first and then the first conjugate.

When the first and second conjugates are contacted with the sample sequentially to one another, an optional wash step can be performed between the steps in the sequence.

In embodiments where the FRET donors on the bound first activated conjugate are in close enough proximity (less than or equal to 10 nm) to the FRET acceptors on the bound second activated conjugate, a positive FRET signal can be detected.

Where the FRET donors on the bound first activated conjugate are not in close enough proximity (greater than 9 nm) to the FRET acceptors on the bound second activated conjugate, the FRET signal will be reduced or absent.

Where either or both of the first and second molecules are not present in the sample, no FRET signal will be detected.

In one aspect of the invention, the primary binding agents are unlabelled. For example, the primary binding agents are not labelled with a FRET donor or FRET acceptor. This has the advantage that the methods of the invention can provide a high throughput, generic methodology that is not reliant on producing primary binding agents with individual binding specificities that are labelled with a FRET donor or FRET acceptor, which is time-consuming and costly.

The primary binding agents can be labelled. For example, the primary binding agents can be labelled with a FRET donor or FRET acceptor. In this aspect, the secondary binding agents can be dispensed with. Alternatively, a labelled primary binding agent can be used in combination with a primary binding agent-second binding agent pairing and a conjugate. For example, a first primary binding agent labelled with a FRET acceptor can be used in combination with a second primary binding agent that is bound by a second secondary binding agent conjugated to an enzyme and a conjugate. In this instance, the first secondary binding agent can be dispensed with. Alternatively, a first primary binding agent that is bound by a first secondary binding agent labelled with a FRET acceptor can be used in combination with a second primary binding agent that is conjugated to an enzyme and a conjugate. In this instance, the second secondary binding agent can be dispensed with. In these embodiments, the enzyme activation system can be applied to the first primary binding agent in addition to the second primary/secondary binding agent. This advantageously amplifies both the FRET donor signal and the FRET acceptor signal. In this aspect, the first primary binding agent is conjugated to an enzyme in place of a FRET donor. The method further employs a second conjugate comprising a FRET donor and a substrate specific for the enzyme, wherein when the substrate reacts with the enzyme, a second activated conjugate forms, which second activated conjugate binds to electron rich moieties on a molecular surface adjacent to the enzyme. The substrate does not react with the enzyme conjugated to the second primary/secondary binding agent.

The methods of the invention are adapted accordingly. For example, the method can comprise the steps of contacting a sample with the at least two primary binding agents, optionally contacting the sample with at least one secondary binding agent, performing a wash step, contacting the sample with a first conjugate specific for the enzyme conjugated to the first primary/secondary binding agent and a second conjugate specific for the enzyme conjugated to the second primary/secondary binding agent, and detecting any FRET signal generated by the FRET acceptor. The first conjugate can be applied simultaneously or sequentially to the second conjugate. For example, the first conjugate can be contacted with the sample first and then the second conjugate can be contacted with the sample. Alternatively, the second conjugate can be contacted with the sample first and then the first conjugate. When the first and second conjugates are contacted with the sample sequentially to one another, an optional wash step can be performed between the steps in the sequence.

In embodiments where the FRET donors on the bound first activated conjugate, first primary binding agent or first secondary binding agent are in close enough proximity (less than or equal to 10 nm) to the FRET acceptors on the bound second activated conjugate, a positive FRET signal can be detected.

Where the FRET donors on the bound first activated conjugate, first primary binding agent or first secondary binding agent are not in close enough proximity (greater than 10 nm) to the FRET acceptors on the bound second activated conjugate, the FRET signal will be reduced or absent.

Where either or both of the first and second molecules are not present in the sample, no FRET signal will be detected.

In some embodiments, the methods of the invention employ more than two primary binding agents.

In some embodiments, the methods of the invention employ more than two secondary binding agents.

The samples of the invention include isolated biological samples, isolated cells and tissue sections. In preferred embodiments, the samples are breast tumour samples, including breast tumour tissue sections.

Advantageously, the secondary binding agents employed in the invention can be antibody or antigen-binding fragments, such as Fab fragments or scFv fragments, rather than whole immunoglobulins. The secondary binding agents can be a combination of Fab fragments, antibody scaffolds and whole immunoglobulins (Fab fragment mixtures). Embodiments of the invention employing antibody or antigen-binding fragments (for example, ranging in size from 50 kDa to 100 kDa) or Fab fragment mixtures for the secondary binding agents have been found to be particularly effective. Particular advantages are a reduced FRET donor to FRET acceptor chromophore distance and increased FRET efficiency, easy penetration of tissues and binding to their targets. Additionally, their inherent specificity is further enhanced by the fact that they lack the Fc region, therefore any background that results from non-specific binding to endogenous Fc receptors is significantly reduced. This is particularly advantageous where the two target sites are on the same molecule.

The use of an enzyme activation system in combination with the FRET methods of the invention improves the FRET efficiency, particularly in two-site FRET. Previously, it was anticipated that the size of the system would increase the distance between the FRET donor and FRET acceptor, leading to loss of FRET. However, the inventors found that the methods of the invention provide an improved signal/noise ratio, as well as a low cost, generic and robust high throughput methodology.

Advantageously, the enzyme activation system increases the detection of low-expressed proteins, preferably endogenous proteins and also allows dilution of primary binding agents, itself reducing non-specific interactions and therefore improving specificity.

The methods of the invention have the advantage of a significant increase in sensitivity, without an increase in the background.

In one example, primary, whole immunoglobulins anti-PD-1 (mouse) and anti-PD-L1 (T308) (rabbit) are contacted with a fixed tumour cell sample from a cancer patient. Secondary, Fab fragments anti-mouse-ORG488 and anti-rabbit-HRP are contacted with the sample and bind the anti-PD-1 (mouse) and anti-PD-L1 (T308) (rabbit) antibodies, respectively. After a wash step, tyramide (TSA)-ALX594 is applied to the sample. HRP catalyses the activation of multiple copies of TSA-ALX594. The resulting, short-lived tyramide radicals covalently couple to electron rich residues adjacent to the HRP, which deposits multiple copies of ALX594 adjacent to the PD-L1 target site. The short half-life of the tyramide radicals results in minimal diffusion-related loss of ALX594 signal localisation. A positive FRET signal is generated between ORG488 and ALX594 where PD-1 and PD-L1 are in close proximity on the cell surface of different cells (less than or equal to 10 nm). The FRET signal can be detected in a time resolved manner by multiple frequency domain FLIM (mFD-FLIM).

In one aspect, the invention relates a highly sensitive quantitative coincidence assay. In certain embodiments, two-site TSA-FRET combines the immunofluorescence tyramide signal amplification (TSA) with Fab fragment secondary antibody conjugates, in order to maximise sensitivity and specificity.

A "plug-in" algorithm can be used to automate an mFD-FLIM. Such a miniaturised instrument automatically distinguishes between regions of interest (ROI) in cells and tumours, which allows for unbiased selection of specific ROIs.

In embodiments of the invention, miniaturised automated mFD-FLIM can be used in combination with two-site TSA-FRET to readily detect the activation of PD-1 and/or PD-L1/PD-L2, in tumour samples. The methods can be used to routinely to inform on prognostic, predictive and diagnostic immune checkpoint inhibitors.

Advantageously, the methods of the invention combine the spatio-temporal and quantitative attributes of time resolved FRET detected by multiple frequency domain FLIM (mFD-FLIM) with the sensitivity of the tyramide signal amplification (TSA) system.

In a further example, primary, whole anti-CTLA-4 or anti-CD28 immunoglobulins (mouse) and primary, whole anti-CD80 or anti-CD86 immunoglobulins (rabbit) are contacted with a fixed tumour cell sample from a cancer patient. Secondary, Fab fragments anti-mouse-ORG488 and anti-rabbit-HRP are contacted with the sample and bind the anti-CTLA-4/CD28 (mouse) and anti-CD80/CD86 (rabbit) antibodies, respectively. After a wash step, tyramide (TSA)-ALX594 is applied to the sample. HRP catalyses the activation of multiple copies of TSA-ALX594. The resulting, short-lived tyramide radicals covalently couple to electron rich residues adjacent to the HRP, which deposits multiple copies of ALX594 adjacent to the CD80/CD86 target site. The short half-life of the tyramide radicals results in minimal diffusion-related loss of ALX594 signal localisation. A positive FRET signal is generated between ORG488 and ALX594 where CTLA-4/CD28 and CD80/CD86 are in close proximity on the cell surface of different cells (less than or equal to 10 nm). The FRET signal can be detected in a time resolved manner by multiple frequency domain FLIM (mFD-FLIM).

In another example, primary, whole anti-MHC Class I or II peptide immunoglobulins (mouse) and primary, whole anti-TCR, CD8 or CD3 immunoglobulins (rabbit) are contacted with a fixed tumour cell sample from a cancer patient. Secondary, Fab fragments anti-mouse-ORG488 and anti-rabbit-HRP are contacted with the sample and bind the anti-MHC Class I/II peptide (mouse) and anti-TCR/CD8/CD3 (rabbit) antibodies, respectively. After a wash step, tyramide (TSA)-ALX594 is applied to the sample. HRP catalyses the activation of multiple copies of TSA-ALX594. The resulting, short-lived tyramide radicals covalently couple to electron rich residues adjacent to the HRP, which deposits multiple copies of ALX594 adjacent to the TCR/CD8/CD3 target site. The short half-life of the tyramide radicals results in minimal diffusion-related loss of ALX594 signal localisation. A positive FRET signal is generated between ORG488 and ALX594 where MHC Class I/II peptide and TCR/CD8/CD3 are in close proximity on the cell surface of different cells (less than or equal to 10 nm). The FRET signal can be detected in a time resolved manner by multiple frequency domain FLIM (mFD-FLIM). The skilled person would appreciate that the claimed methods, uses and kits can be applied to other immune checkpoint target pairs, to detect and/or quantify the interaction between immune check point targets at the cellular level.

Proximity Ligation

In another aspect, the present invention provides a methodology employing at least two primary binding agents and at least two secondary binding agents conjugated or fused to a DNA sequence. The DNA sequence conjugated or fused to the first secondary binding agent can be different to the DNA sequence conjugated or fused to the second secondary binding agent. The DNA sequences ligate to form a circle by rolling circle DNA amplification, and are bound by externally applied fluorescently labelled DNA probes complimentary to that of the amplified circular DNA sequences.

The externally applied DNA probes can be labelled with a detectable label, such as a fluorescent label. Other detectable labels are envisaged, such as HRP and chromophores.

The first primary binding agent binds to a first molecule (e.g. a checkpoint target protein) on a first cell and the second primary binding agent binds to a second molecule (e.g. another or a different checkpoint target protein) on a second cell, and the first and second primary binding agents are immunologically distinct.

The first secondary binding agent is conjugated or fused to a first DNA sequence and binds to the first primary binding agent; and the second secondary binding agent is conjugated or fused to a second DNA sequence and binds the second primary v. The first and second DNA sequences can be different. The first secondary v does not bind the second primary binding agent and the second secondary binding agent does not bind the first primary binding agent.

The DNA sequences are ligated to form a circle, amplified by rolling circle DNA amplification, and are bound by externally applied fluorescently labelled DNA probes complimentary to that of the amplified DNA sequences.

More specifically, the secondary binding agents directed against the constant regions of the respective primary binding agents, called PLA probes, bind to the respective primary binding agents. The first secondary binding agent directed against the constant regions of the first primary binding agent, called the first PLA probe, binds to the first primary binding agent. The second secondary binding agent directed against the constant regions of the second primary binding agent, called the second PLA probe, binds to the second primary binding agent. The first and second PLA probes have different short DNA strands attached to them. If the first and second PLA probes are in close proximity (up to about 40 nm; preferably up to about 28 nm), that is, if the two target cells of interest are in close proximity, the DNA strands can be ligated and then amplified in the presence of appropriate substrates and enzymes. The ligation is determined by the distance between the PLA probes, such that ligation occurs when the probes are in close proximity (up to about 40 nm; preferably up to about 28 nm). Once ligated, amplification occurs in the presence of appropriate substrates and enzymes. Such substrates and enzymes are known in the art.

The rolling circle DNA synthesis step can result in a several-hundredfold amplification of the DNA circle, which when contacted with the fluorescently-labelled oligonucleotide probes that bind the amplified DNA, a high concentration of fluorescence can be detected, for example, by fluorescence microscopy.

The methods of the present invention can comprise the steps of contacting a cell sample with the at least two primary binding agents, contacting the sample with the at least two secondary binding agents, performing a wash step, performing rolling circle DNA amplification, contacting the sample with fluorescently labelled DNA probes complimentary to that of the amplified circular DNA sequences, and detecting any fluorescence signal generated.

Using the methods of the invention, it is possible to detect a fluorescence signal if the first molecule and second molecule are in close spatial proximity (less than about 40 nm; preferably less than about 28 nm).

In the methods of the invention, the at least two primary binding agents are contacted with the cell sample. The at least two primary binding agents can be contacted with the sample at the same time as one another or sequentially to one another. Therefore, the first primary binding agent can be contacted with the sample first and then the second primary binding agent can be contacted with the sample. Alternatively, the second primary binding agent can be contacted with the sample first and then the second primary binding agent. When the first and second primary binding agents are contacted with the sample sequentially to one another, an optional wash step can be performed between the steps in the sequence.

The first primary binding agent binds to any first molecule on a first cell present in the sample and the second primary binding agent binds to any second molecule on a second cell present in the sample. The optional wash step removes any unbound primary binding agent.

The at least two secondary binding agents can be contacted with the cell sample at the same time as the at least two primary binding agents or the at least two primary binding agents can be contacted with the sample before the at least two secondary binding agents. The at least two secondary binding agents can be contacted with the sample at the same time as one another or sequentially to one another. Therefore, the first secondary binding agent can be contacted with the sample first and then the second secondary binding agent can be contacted with the sample. Alternatively, the second secondary binding agent can be contacted with the sample first and then the first secondary binding agent. When the first and second secondary binding agents are contacted with the sample sequentially to one another, an optional wash step can be performed between the steps in the sequence. In embodiments where the at least two primary binding agents are contacted with the sample before the at least two secondary binding agents, an optional wash step can be performed between administration of the at least two primary binding agents and the administration of the at least two secondary binding agents.

The first secondary binding agent binds to the first primary binding agent and the second primary binding agent binds to the second primary binding agent. The optional wash step removes any unbound secondary binding agent or any secondary binding agent that has bound to primary binding agent that has not bound the first or second site (i.e. unbound primary binding agent).

Following contact of the at least two primary binding agents and the at least two secondary binding agents with the sample, a wash step is performed before the conjugate is contacted with the sample. The wash step removes any binding agent (primary or secondary) that has not bound its target (e.g. the first site, second site, first primary antibody or second primary binding agent). Saline solution or another suitable solution can be used to perform the wash steps in the methods of the invention. The conditions used in the wash step are well known to a person of ordinary skill in the art.

Rolling circle DNA amplification is performed. The DNA sequences are ligated to form a circle and then amplified by rolling circle DNA amplification. The amplified DNA is then contacted with externally applied fluorescently labelled DNA probes complimentary to that of the amplified circular DNA sequences. An optional wash step is performed. The bound probes are then detected via their detectable label.

The rolling circle DNA amplification step amplifies the number of circular DNA sequences that are bound by the externally applied fluorescently labelled DNA probes, indicating the presence of a target molecule interaction. Any detectable signal generated is detected.

In embodiments where the first target molecule is in close enough proximity (less than about 40 nm; preferably less than about 28 nm) to the second target molecule, a positive detectable (fluorescence) signal can be detected.

Where the first target molecule is not in close enough proximity (greater than about 40 nm; preferably greater than about 28 nm) to the second target molecule, the detectable (fluorescence) signal will be reduced or absent.

Where either or both of the first and second molecules are not present in the sample, no detectable (fluorescence) signal will be detected.

The methods of the invention are adapted accordingly. For example, the method can comprise the steps of contacting a sample with the at least two primary binding agents, contacting the sample with the at least two secondary binding agents, performing a wash step, performing rolling circle DNA amplification, contacting the sample with externally applied fluorescently labelled DNA probes complimentary to that of the amplified circular DNA sequences, and detecting any detectable (fluorescence) signal generated.

In some embodiments, the methods of the invention employ more than two primary binding agents.

In some embodiments, the methods of the invention employ more than two secondary binding agents.

Advantageously, the secondary binding agents employed in the invention can be antibody or antigen-binding fragments, such as Fab fragments or scFv fragments, rather than whole immunoglobulins. The secondary binding agents can be a combination of Fab fragments, antibody scaffolds and whole immunoglobulins (Fab fragment mixtures). Embodiments of the invention employing antibody or antigen-binding fragments (for example, ranging in size from 50 kDa to 100 kDa) or Fab fragment mixtures for the secondary binding agents have been found to be particularly effective. Particular advantages are a reduced target distance and increased the fluorescence efficiency, easy penetration of tissues and binding to their targets. Additionally, their inherent specificity is further enhanced by the fact that they lack the Fc region, therefore any background that results from non-specific binding to endogenous Fc receptors is significantly reduced.

The methods of the invention have the advantage of a significant increase in sensitivity, without an increase in the background.

In one example, primary, whole immunoglobulins anti-PD-1 (mouse) and anti-PD-L1 (T308) (rabbit) are contacted with a fixed tumour cell sample from a cancer patient. Secondary, Fab fragments anti-mouse-fused to a DNA sequence and anti-rabbit-fused to another DNA sequence are contacted with the sample and bind the anti-PD-1 (mouse) and anti-PD-L1 (T308) (rabbit) antibodies, respectively.

The DNA sequences are ligated to form a circle and amplified by rolling circle DNA amplification, and are bound by externally applied fluorescently labelled DNA probes complimentary to that of the amplified circular DNA sequences where PD-1 and PD-L1 are in close proximity on the cell surface of different cells (less than about 40 nm, preferably less than about 28 nm). The fluorescence signal can be detected by fluorescence microscopy. The invention relates to a highly sensitive quantitative coincidence assay.

In a further example, primary, whole anti-CTLA-4 or anti-CD28 immunoglobulins (mouse) and primary, whole anti-CD80 or anti-CD86 immunoglobulins (rabbit) are contacted with a fixed tumour cell sample from a cancer patient. Secondary, Fab fragments anti-mouse-fused to a DNA sequence and anti-rabbit-fused to another DNA sequence are contacted with the sample and bind the anti-CTLA-4/CD28 (mouse) and anti-CD80/CD86 (rabbit) antibodies, respectively.

The DNA sequences are ligated to form a circle and amplified by rolling circle DNA amplification, and are bound by externally applied fluorescently labelled DNA probes complimentary to that of the amplified circular DNA sequences where CTLA-4/CD28 and CD80/CD86 are in close proximity on the cell surface of different cells (less than about 40 nm, preferably less than about 28 nm). The fluorescence signal can be detected by fluorescence microscopy. The invention relates to a highly sensitive quantitative coincidence assay.

In another example, primary, whole anti-MHC Class I or II peptide immunoglobulins (mouse) and primary, whole anti-TCR, CD8 or CD3 immunoglobulins (rabbit) are contacted with a fixed tumour cell sample from a cancer patient. Secondary, Fab fragments anti-mouse-fused to a DNA sequence and anti-rabbit-fused to another DNA sequence are contacted with the sample and bind the anti-MHC Class I/I peptide (mouse) and anti-TCR/CD8/CD3 (rabbit) antibodies, respectively.

The DNA sequences are ligated to form a circle and amplified by rolling circle DNA amplification, and are bound by externally applied fluorescently labelled DNA probes complimentary to that of the amplified circular DNA sequences where MHC Class I/II peptide and TCR/CD8/CD3 are in close proximity on the cell surface of different cells (less than about 40 nm, preferably less than about 28 nm). The fluorescence signal can be detected by fluorescence microscopy. The invention relates to a highly sensitive quantitative coincidence assay.

Although the methods of the invention can employ PLA, such methodology was only found to determine distances in the range of 20 nm to 40 nm. PLA distances lower than 20 nm could not be determined.

In contrast, the two-site TSA FRET methods of the present invention were able to measure distances in the range of 10 nm or less. Such methods also allow a quantitative rather than merely qualitative assay that has universal application (not limited to specific cancer types or specific cell-cell interactions).

Coincidence Detection

In another aspect, the present invention uses a coincidence detection method to detect the interaction between two target molecules presented on the surface of separate cells.

The method uses two fusion proteins, where each fusion protein comprises a detection domain, a recognition domain and a connector domain. The detection domain can comprise a DNA binding domain and is capable of binding a cognate specific nucleotide sequence in co-operation with a further detection domain. The recognition domain is capable of binding a target molecule. The connector domain is fused at one end to the detection domain and fused at the other end to the recognition domain. The detection domain, recognition domain and connector domain are heterologous to one another. The method involves the steps of (i) contacting the sample with the fusion proteins; (ii) incubating to allow binding; (iii) removing unbound fusion protein; (iv) contacting the sample with nucleic acid comprising the cognate specific nucleotide sequence; (v) incubating to allow heterotrimeric binding of the nucleic acid; and (vi) detecting nucleic acid bound to the sample. If the nucleic acid is detected in step (vi), this indicates that the two target molecules are present coincidentally in said sample. Such methods are disclosed in WO/2011/161420, which is incorporated herein by reference in its entirety.

The present invention provides an in vitro coincidence assay method for detecting the interaction between a first molecule expressed on a first cell and a second molecule expressed on a second cell, the method comprising:
   a first and second fusion protein, wherein each fusion protein comprises a detection domain, a recognition domain and a connector domain;
   the detection domain comprises a DNA binding domain and is capable of binding a cognate specific nucleotide sequence in co-operation with a further detection domain;
   the recognition domain is capable of binding a target molecule;
   the connector domain is fused at one end to the detection domain and fused at the other end to the recognition domain;
   the detection domain, recognition domain and connector domain are heterologous to one another;
   the method comprising the steps of:
   (i) contacting the sample with the first and fusion proteins;
   (ii) incubating to allow binding;
   (iii) removing unbound fusion protein;
   (iv) contacting the sample with nucleic acid comprising the cognate specific nucleotide sequence;
   (v) incubating to allow heterotrimeric binding of the nucleic acid; and
   (vi) detecting nucleic acid bound to the sample;
wherein, if the nucleic acid is detected in step (vi), this indicates that the two target molecules are present coincidentally in the sample.

In one example, the first fusion protein detects PD-1 and the second fusion protein detects PD-L1. In another example, the first fusion protein binds CTLA-4 or CD28 and the second fusion protein binds CD80 or CD86. In a further example, the first fusion protein binds an MHC Class I or II peptide and the second fusion protein binds TCR, CD8 or CD3.

Selecting and Stratifying Cancer Patients

The present invention provides methods of selecting a patient with cancer for treatment. The methods provide coincidence assays, including FRET, FRET with amplification (e.g. TSA-FRET), proximity ligation and coincidence detection, for use in methods of selecting a patient for cancer treatment. The methods provide for detecting interactions between molecules at the cellular level to guide patient selection.

The invention provides methods of selecting a patient with cancer for treatment, the method comprising:
   at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;
   at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:

(iv) the first secondary binding agent is labelled with a FRET donor and the second secondary binding agent is labelled with a FRET acceptor;
(v) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
(vi) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(e) contacting an isolated tumour cell sample from the patient with the at least two primary binding agents;
(f) contacting the sample with the at least two secondary binding agents;
(g) performing a wash step;
(h) detecting the interaction between the secondary binding agents by determining the overall fluorescence score; wherein:
a. where the intended therapy comprises a checkpoint activator targeting at least one of the first and second checkpoint target molecules:
i. if the overall score is less than or equal to a threshold score, the overall score indicates or predicts that the patient will respond to the intended therapy; or
ii. if the overall score is greater than a threshold score, the overall score indicates or predicts that the patient will not respond to the intended therapy; or
b. where the intended therapy comprises a checkpoint inhibitor targeting at least one of the first and second checkpoint target molecules:
(v) if the overall score is less than or equal to a threshold score, the overall score indicates or predicts that the patient will not respond to the intended therapy; or
(vi) if the overall score is greater than a threshold score, the overall score indicates or predicts that the patient will respond to the intended therapy.

The present invention also provides the use of the above in vitro coincidence assay methods for selecting a patient with cancer for treatment, and kits for use in this respect.

The patient may not previously have received cancer therapy or may have previously received cancer therapy but for a different target molecule to the target molecule (e.g. checkpoint target protein) for which the patient is being selected in the aforementioned methods.

If the overall score is 0.5% to 5%, this indicates the patient will not respond to a therapy targeting at least one of the checkpoint target molecules. If the overall score is 5% to 10%, this indicates the patient may respond to a therapy targeting at least one of the checkpoint target molecules. If the overall score is greater than 10%, this indicates the patient will respond to a therapy targeting at least one of the checkpoint target molecules. The overall score can be the percentage FRET efficiency.

In some methods the at least two primary binding agents bind to the first molecule or second molecule in such a manner that the checkpoint inhibitor or activator can bind to the first molecule or second molecule at the same time or subsequently. In some methods, the at least two primary binding agents do not inhibit the binding of the checkpoint inhibitor or activator to the first molecule or the second molecule.

The tumour cell sample can be obtained from the patient prior to treatment or following treatment for the different target molecule.

The cell sample is preferably a fixed cell sample. The tumour cell sample can include primary tumour cells, secondary (metastatic) tumour cells, solid tumours and the associated patient tissue (e.g. macrophages, T cells, B cells, etc.). The cell sample can be a tumour biopsy or surgical incision obtained from the patient. Typically, the tumour sample comprises an invasive tumour margin. The tumour sample can be obtained from a metastatic lesion. The sample can comprise peripheral blood.

The patient can be one who is suspected of having a metastatic cancer. Examples of cancer include, but are not limited to, melanoma, lung cancer, including for example non-small cell lung cancer, breast cancer, head and neck cancer, urothelial cancer. Further examples of cancer include adrenocortical carcinoma, anal cancer, bladder cancer, blood cancer, brain stem glioma, cerebellar astrocytoma, ependymoma, carcinoid tumour, carcinoma of unknown primary, cervical cancer, colon cancer, endometrial cancer, esophageal cancer, extrahepatic bile duct cancer, Ewings family of tumours (PNET), extracranial germ cell tumour, eye cancer, intraocular melanoma, gallbladder cancer, gastric cancer, germ ceil tumour, extragonadal, gestational trophoblastic tumor, hypopharyngeai cancer, islet ceil carcinoma, kidney cancer (renal cell cancer), laryngeal cancer, acute lymphoblastic leukemia, acute myeloid leukemia, chronic lymphocytic leukemia, chronic myelogenous leukemia, hairy ceil leukemia, lip and oral cavity cancer, liver cancer, small cell lung cancer, lymphoma, cutaneous T-ceil lymphoma, Hodgkin's and non-Hodgkin's lymphoma, multiple myeloma and other plasma cell neoplasms, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell tumor, pancreatic cancer, islet cell carcinoma, paranasal sinus and nasal cavity cancer, parathyroid cancer, penile cancer, pituitary cancer, plasma cell neoplasm, prostate cancer, rhabdomyosarcoma, rectal cancer, renal cell cancer, salivary gland cancer, sezary syndrome, skin cancer, kaposi's sarcoma, melanoma, small intestine cancer, soft tissue sarcoma, stomach cancer, testicular cancer, thymoma, malignant, thyroid cancer, urethral cancer, uterine cancer, sarcoma, vaginal cancer, vulvar cancer, and Wilms' tumor.

In one example, the first fusion protein binds a first checkpoint protein target on a first cell and the second fusion protein detects a second checkpoint protein target on a second cell, such that the fusion proteins detect cell-cell interactions.

Exemplary checkpoint target molecules include programmed cell death-1 (PD-1) receptor, PD-ligand 1 (PD-L1), PD-ligand 2 (PD-L2), cytotoxic T-lymphocyte-associated antigen 4 (CTLA-4), B7 family proteins, tumour necrosis factor (TNF) family proteins, cluster of differentiation 40 L (CD40L), adenosine A2a receptor (A2aR), B7-related protein 1 (B7RP1), B and T lymphocyte attenuator (BTLA), galactin 9 (GAL9), herpesvirus entry mediator (HVEM), inducible T cell co-stimulator (ICOS), interleukin (IL), killer cell immunoglobulin-like receptor (KIR), lymphocyte activation gene 3 (LAG3), transforming growth factor-β (TGF-β), T cell membrane protein 3 (TIM3) and MHC Class I or II peptides. A preferred checkpoint target is PD-1. PD-L1 or PD-L2 is also a preferred checkpoint target. CTLA-4 is a preferred checkpoint target. MHC Class I or II peptides are preferred checkpoint targets. LAG3, B7-H3, B7-H4 and TIM3 are also preferred checkpoint targets.

In one example, the first fusion protein binds PD-1 and the second fusion protein binds PD-L1 or PD-L2. In determining the fluorescence signal score:
  (i) if the overall score is less than or equal to a threshold score, the overall score indicates or predicts that the patient will not respond to treatment with an anti-PD-1, anti-PD-L1 or PD-L2 antibody; or
  (ii) if the overall score is greater than a threshold score, the overall score indicates or predicts that the patient will respond to treatment with an anti-PD-1, anti-PD-L1 or PD-L2 antibody.

In another example, the first fusion protein binds CTLA-4 or CD28 and the second fusion protein binds CD80 or CD86. In determining the fluorescence signal score:
  (i) if the overall score is less than or equal to a threshold score, the overall score indicates or predicts that the patient will not respond to treatment with an anti-CTLA-4, anti-CD28, anti-CD80 or anti-CD86 antibody; or
  (ii) if the overall score is greater than a threshold score, the overall score indicates or predicts that the patient will respond to treatment with an anti-CTLA-4, anti-CD28, anti-CD80 or anti-CD86 antibody.

In a further example, the first fusion protein binds an MHC Class I or II peptide and the second fusion protein binds TCR, CD8 or CD3. In determining the fluorescence signal score:
  (i) if the overall score is less than or equal to a threshold score, the overall score indicates or predicts that the patient will not respond to treatment with an anti-MHC Class I, anti-MHC Class II, anti-TCR, anti-CD8 or anti-CD3 antibody; or
  (ii) if the overall score is greater than a threshold score, the overall score indicates or predicts that the patient will respond to treatment with an anti-MHC Class I, anti-MHC Class II, anti-TCR, anti-CD8 or anti-CD3 antibody.

In additional aspects, the present invention provides in vitro coincidence assay methods for detecting whether a checkpoint activator or inhibitor is effective in inhibiting or modulating a tumour response, the method comprising:
  at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;
  at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
    (i) the first secondary binding agent is labelled with a FRET donor and the second secondary binding agent is labelled with a FRET acceptor;
    (ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
    (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;
  wherein the method comprises:
    (a) contacting an isolated tumour cell sample with the at least two primary binding agents;
    (b) contacting the sample with the at least two secondary binding agents;
    (c) performing a wash step;
    (d) detecting the interaction between the secondary binding agents by determining the overall fluorescence score;
    (e) contacting the sample with the checkpoint activator or inhibitor;
    (f) detecting any change in the interaction between the secondary binding agents, wherein:
      a. where the checkpoint molecule is an inhibitor:
        i. if the overall score decreases between steps (d) and (f) it is indicated or predicted that the checkpoint inhibitor is effective; or
        ii. if the overall score is unchanged between steps (d) and (f) it is indicated or predicted that the checkpoint inhibitor is not effective; or
      b. where the checkpoint molecule is an activator:
        i. if the overall score increases between steps (d) and (f) it is indicated or predicted that the checkpoint activator is effective; or
        ii. if the overall score is unchanged between steps (d) and (f) it is indicated or predicted that the checkpoint activator is not effective.

The present invention also provides the use of the above in vitro coincidence assay methods for detecting whether a checkpoint activator or inhibitor is effective in inhibiting or modulating a tumour response, and kits for use in this respect.

Exemplary checkpoint inhibitors include anti-PD-1 binding agents, anti-PD-L1 binding agents, anti-PD-L2 binding agents, anti-CTLA-4 binding agents, anti-MHC Class I and/or anti-MHC Class II binding agents. An exemplary anti-CTLA-4 antibody is ipilimumab. Exemplary anti-PD-1 binding agents include nivolumab (BMS-936558, DX 1106 or ONO-4538) and pembrolizumab (iambrolizumab or MK-3475).

Further exemplary checkpoint inhibitors include those selected from the group comprising or consisting of ipilimumab, nivolumab (BMS-936558, DX 1106 or ONO-4538), pembrolizumab (iambrolizumab or MK-3475), pidilizumab (CT-Q1 1), ED-0680 (AMP-514), AMP-224, BMS-936559 (MDX-1 105), ED 4736, MPDL3280A (RG7448), MSB0010718C, and fragments and salts thereof.

Exemplary checkpoint activators include those from the TNF receptor and the B7-CD28 superfamilies, including CD40 (TNFSFR5) agonists, GITR (Glucocorticoid-Induced Tumor Necrosis Factor Receptor; TNFSFR18) stimulators, OX40 (CD134; TNFSFR4) agonists, 4-1BB (CD137; TNFSFR9) agonists, CD27 (TNFSFR7) agonists CD27 (TNFSFR7) agonists, ICOS (Inducible Co-Stimulator) molecule agonists, Trail receptor agonists and/or HVEM (Herpesvirus entry mediator) receptor agonists. Preferred checkpoint activators include OX-40, GITR and/or 4-1BB agonists.

In the above methods, an overall score increase between steps (d) and (f) of 0.5% to 5%, preferably 5% to 10%, more preferably greater than 10%, indicates that the checkpoint activator will be effective. An overall score decrease between steps (d) and (f) of 0.5% to 5%, preferably 5% to 10%, more preferably greater than 10%, indicates that the checkpoint inhibitor will be effective.

In the above methods, at least two primary binding agents can bind to the first molecule or second molecule in such a manner that the checkpoint inhibitor or activator can bind to the first molecule or second molecule at the same time or subsequently. In some aspects, the at least two primary binding agents do not inhibit the binding of the checkpoint inhibitor or activator to the first molecule or the second molecule.

In additional aspects, the present invention provides in vitro methods of determining whether a therapy comprising a checkpoint activator or inhibitor is effective in a patient, the method comprising:
- at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;
- at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
  - (i) the first secondary binding agent is labelled with a FRET donor and the second secondary binding agent is labelled with a FRET acceptor;
  - (ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
  - (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
- (a) contacting an isolated tumour cell sample obtained from the patient prior to the treatment comprising the checkpoint activator or inhibitor with at least two primary binding agents;
- (b) contacting the sample with the at least two secondary binding agents;
- (c) performing a wash step;
- (d) detecting the interaction between the secondary binding agents by determining the overall fluorescence score;
- (e) repeating steps (a) to (d) using an isolated tumour cell sample obtained from the patient during treatment comprising the checkpoint activator or inhibitor in step (a);
- (f) comparing the overall fluorescence scores between the samples, wherein:
  - a. where the therapy comprises a checkpoint inhibitor:
    - i. if the overall score decreases, it is indicated or predicted that the therapy is effective; or
    - ii. if the overall score is unchanged, it is indicated or predicted that the therapy is not effective; or
  - b. where the therapy comprises a checkpoint activator:
    - i. if the overall score increases, it is indicated or predicted that the therapy is effective; or
    - ii. if the overall score is unchanged, it is indicated or predicted that the therapy is not effective.

The present invention also provides the use of the above in vitro methods for determining whether a therapy comprising a checkpoint activator or inhibitor is effective in a patient, and kits for use in this respect.

The present invention further provides in vitro methods of determining whether a patient with cancer will be responsive to an agent that blocks the PD-1:PD-L1/PD-L2 pathway, the method comprising:
- at least two primary binding agents, wherein a first primary binding agent binds to PD-1 on the first cell and a second primary binding agent binds to PD-L1 or PD-L2 on the second cell, and wherein the first and secondary primary binding agents are immunologically distinct; and
- at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
  - (iv) the first secondary binding agent is labelled with a FRET donor and the second secondary binding agent is labelled with a FRET acceptor;
  - (v) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
  - (vi) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

the method comprising:
- (d) contacting an isolated tumour cell sample obtained from the patient with the at least two primary binding agents;
- (e) contacting the sample with the at least two secondary binding agents;
- (f) performing a wash step;
- (d) detecting the interaction between the secondary binding agents by determining the overall fluorescence signal score, wherein:
  - (i) if the overall score is less than or equal to a threshold score, the overall score indicates or predicts that the patient will not respond to treatment with an agent that blocks the PD-1:PD-L1/PD-L2 pathway; or
(ii) if the overall score is greater than a threshold score, the overall score indicates or predicts that the patient will respond to treatment with an agent that blocks the PD-1:PD-L1/PD-L2 pathway.

The method can be performed:
(iii) on a biological sample obtained from the patient prior to treatment to guide the decision on selection of treatment with a single agent that blocks the PD-1:PD-L1/PD-L2 pathway, or with an agent that blocks the PD-1:PD-L1/PD-L2 pathway and at least one other anti-tumour agent in a combination therapy; and
(iv) on at least one biological sample obtained from the patient during treatment to monitor response of the subject to the current treatment regimen and to guide decision on selection of treatment with a single-agent PD-1:PD-L1/PD-L2 blockade therapy or with a combination therapy.

In the above method, an overall score decrease between steps (d) and (f) of 0.5% to 5%, preferably 5% to 10%, more preferably greater than 10%, indicates that the PD-1:PD-L1/PD-L2 pathway will be effective.

The above method can also be applied to other agents that block the immune checkpoint pathway or activate the immune checkpoint pathway. Exemplary checkpoint inhibitors and activators are described above. For example, the agent could block CTLA-4, CD28, CD80 and/or CD86. The agent could block an MHC Class I peptide, MHC Class II peptide, TCR, CD8 and/or CD3.

Where the agent is a checkpoint inhibitor, an overall score decrease between steps (d) and (f) of 0.5% to 5%, preferably 5% to 10%, more preferably greater than 10%, indicates that the agent will be effective.

Where the agent is a checkpoint activator, an overall score increase between steps (d) and (f) of 0.5% to 5%, preferably 5% to 10%, more preferably greater than 10%, indicates that the agent will be effective.

In the above methods, at least two primary binding agents can bind to the first molecule or second molecule in such a manner that the checkpoint inhibitor or activator can bind to the first molecule or second molecule at the same time or subsequently. In some aspects, the at least two primary binding agents do not inhibit the binding of the checkpoint inhibitor or activator to the first molecule or the second molecule.

The sample used in the above methods can be a fixed tumour cell sample. In certain aspects, the cell sample is obtained from the patient prior to treatment or during treatment. The sample can be obtained from a patient that has been previously treated for cancer e.g. previously treated with an anti-tumour agent, or can mean obtained from a patient that has not previously been treated for cancer i.e. a treatment naïve patient.

The cell sample can include primary tumour cells, secondary (metastatic) tumour cells, solid tumours and the associated patient tissue (e.g. macrophages, T cells, B cells, etc.). The tumour sample can be, for example, a tumour biopsy or surgical incision obtained from the patient. Typically, the tumour sample comprises an invasive tumour margin. The tumour sample can be obtained from a metastatic lesion. The sample can comprise peripheral blood vessels. The patient can be one who is suspected of having a metastatic cancer. Examples of cancer include, but are not limited to, melanoma, lung cancer, including for example non-small cell lung cancer, breast cancer, head and neck cancer, urothelial cancer. Further examples of cancer include adrenocortical carcinoma, anal cancer, bladder cancer, blood cancer, brain stem glioma, cerebellar astrocytoma, ependymoma, carcinoid tumour, carcinoma of unknown primary, cervical cancer, colon cancer, endometrial cancer, esophageal cancer, extrahepatic bile duct cancer, Ewings family of tumours (PNET), extracranial germ cell tumour, eye cancer, intraocular melanoma, gallbladder cancer, gastric cancer, germ ceil tumour, extragonadal, gestational trophoblastic tumor, hypopharyngeai cancer, islet cell carcinoma, kidney cancer (renal cell cancer), laryngeal cancer, acute lymphoblastic leukemia, acute myeloid leukemia, chronic lymphocytic leukemia, chronic myelogenous leukemia, hairy cell leukemia, lip and oral cavity cancer, liver cancer, small cell lung cancer, lymphoma, cutaneous T-cell lymphoma, Hodgkin's and non-Hodgkin's lymphoma, multiple myeloma and other plasma cell neoplasms, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell tumor, pancreatic cancer, islet cell carcinoma, paranasal sinus and nasal cavity cancer, parathyroid cancer, penile cancer, pituitary cancer, plasma cell neoplasm, prostate cancer, rhabdomyosarcoma, rectal cancer, renal cell cancer, salivary gland cancer, sezary syndrome, skin cancer, kaposi's sarcoma, melanoma, small intestine cancer, soft tissue sarcoma, stomach cancer, testicular cancer, thymoma, malignant, thyroid cancer, urethral cancer, uterine cancer, sarcoma, vaginal cancer, vulvar cancer, and Wilms' tumor.

Methods of Selecting Checkpoint Inhibitors or Activators

The present invention further provides in vitro coincidence assay methods for identifying whether a molecule of interest is a checkpoint activator or a checkpoint inhibitor, the method comprising:
  at least two primary binding agents, wherein the first primary binding agent binds to a first checkpoint target molecule on the first cell and the second primary binding agent binds to a second checkpoint target molecule on the second cell, and wherein the first and secondary primary binding agents are immunologically distinct;
  at least two secondary binding agents, wherein a first secondary binding agent binds to the first primary binding agent; and a second secondary binding agent binds the second primary binding agent, wherein the first secondary binding agent does not bind the second primary binding agent and the second secondary binding agent does not bind the first primary binding agent; and wherein:
    (i) the first secondary binding agent is labelled with a FRET donor and the second secondary binding agent is labelled with a FRET acceptor;
    (ii) the first and second secondary binding agents are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
    (iii) the first secondary binding agent is labelled with a FRET donor and the second secondary binding agent is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(a) contacting an isolated tumour cell sample with the at least two primary binding agents;
(b) contacting the sample with the at least two secondary binding agents;
(c) performing a wash step;
(d) detecting the interaction between the secondary binding agents by determining the overall fluorescence score;
(e) contacting the sample with the molecule of interest;
(f) detecting any change in the interaction between the secondary binding agents, wherein:
  a. the molecule is a checkpoint activator for at least one of the first and second checkpoint target molecules if the overall score increases between steps (d) and (f); or
  b. the molecule is a checkpoint inhibitor for at least one of the first and second checkpoint target molecules if the overall score is decreases between steps (d) and (f); or
  c. the molecule is neither a checkpoint activator or inhibitor for at least one of the first and second checkpoint target molecules if the overall score is unchanged between steps (d) and (f).

An overall score increase between steps (d) and (f) of 0.5% to 5%, preferably 5% to 10%, more preferably greater than 10%, indicates that the molecule of interest is a checkpoint activator for at least one of the first and second checkpoint target molecules. An overall score decrease between steps (d) and (f) of 5% to 0.5%, preferably 10% to 5%, more preferably greater than 10%, indicates that the molecule of interest is a checkpoint inhibitor for at least one of the first and second checkpoint target molecules.

In the above method, the at least two primary binding agents can bind to the first molecule or second molecule in such a manner that the molecule of interest can bind to the first molecule or second molecule at the same time or subsequently.

In some aspects, the at least two primary binding agents do not inhibit the binding of the molecule of interest to the first molecule or the second molecule.

The present invention also provides the use of the above in vitro methods for identifying whether a molecule of interest is a checkpoint activator or a checkpoint inhibitor, and kits for use in this respect.

EXAMPLES

The present invention is described in more detail with reference to the following non-limiting examples, which are offered to more fully illustrate the invention, but are not to be construed as limiting the scope thereof.

The methods of the invention can be used to quantify the changes in donor lifetime.

Example 1—Two Site TSA-FRET Analysed by High Throughput Frequency Domain Fluorescence Lifetime Imaging Microscopy (f-FLIM) in Fixed Tissue Sections For the PD-1:PD-L1 interaction studies, FFPE sections were covered and heated with Tris-EDTA buffer and subsequently incubated for a further 10 minutes. The slide vessels were then cooled for 20-30 minutes, before being washed twice with PBS for 5 minutes. The slides were marked with a PAP pen, preventing liquid from leaking from the tissue in the next steps. Every time liquid was added to the tissue, enough liquid was added so that the tissue was completely covered. The endogenous peroxidases were quenched via the addition of endogenous peroxidase suppressor for 30 minutes at room temperature and the tissue was then washed with PBS. The tissues were then blocked using (10 mg/ml) BSA in PBS for 60 minutes at room temperature.

The tissue sections were then split into two conditions: donor only (D) and donor and acceptor (D/A). The two primary antibodies used were mouse anti-PD-1 and rabbit anti PD-L1, diluted 1:100 and 1:500, respectively, in 1% BSA/PBS buffer. Donor only conditions were incubated with mouse anti-PD-1, while donor and acceptor conditions were incubated with both mouse anti-PD-1 and rabbit anti-PD-L1. The primary antibody incubation was left overnight at 4° C.

After incubation, the tissue sections were washed twice with PBS+0.02% Tween 20 to remove non-specific binding of primary antibodies. Sections labelled with just mouse anti-PD-1 (donor only) were further incubated with anti-mouse FAB-ATTO488 (1:100). Sections labelled mouse anti-PD-1 and rabbit anti-PD-L1 were incubated with both anti-mouse FAB-ATT0488 (1:100) and anti-rabbit FabHRP (1:200). The anti-rabbit FabHRP antibody was then further reacted with and amplified with Tyramide-Alexa 594. The tissues were incubated for two hours at room temperature and then washed twice with PBS. The slides where then incubated with tyramide buffer for 20 minute at room temperature before being washed twice with PBS. The slides were then mounted.

Three patients with different types of stage four melanoma were treated with anti-receptor tyrosine kinase (RTK) drugs and an antibody blocking PD-1.

Tissue samples were taken from the three patients, which had the following characteristics:
MM14 (82-year-old female with mucosal melanoma stage 4).
  BRAF wild type.
  cKIT mutant.
  KIT is a receptor tyrosine kinase, which undergoes a hyperactive mutation.
  No active therapy.
  Patient previously treated with nilotinib—which is a tyrosine kinase inhibitor.
  Tissue was a lymph node metastasis.
MM17 (61-year-old male with cutaneous melanoma stage 4).
  BRAF wild type.
  No active therapy
  Prior treatment with ipilimumab (anti-CTLA-4) and nivolumab (anti-PD-1).
  Tissue was a lymph node metastasis.
MM19 (49-year-old male with cutaneous melanoma stage 4.)
  BRAF wild type.
  NRAS mutant.
  NRAS is an oncogene which causes hyper activation of the MAPK pathway.
  Treatment naïve.
  Tissues were a lymph node metastasis and a transverse colon metastasis.

The results are shown in FIGS. 1 and 2. FIGS. 1 and 2 show the variations in PD-1:PD-L1 interactions by TSA-FRET in the patients treated with anti-RTK and an antibody blocking PD-1. The changes in the donor (PD-1), ATTO488 life time are indicated in FIG. 1 by a decrease in lifetime in the presence of the acceptor (PD-L1) fluorophore, ALX 594.

FIG. 2 provides Box and Whiskers plots showing the median FRET Efficiencies and highlighting the variations in PD-1:PD-L1 interactions. The P values indicate the highly significant differences in the FRET efficiencies. Each data point represents a region on the provided tissue where there was the highest receptor (PD-1) concentration. The results show that the methods of the invention allow quantification of molecular interactions, such as PD-1 and PD-L1 interaction in tissue, and that differences in the molecular interactions can be detected following drug treatment.

Example 2—Two Site TSA-FRET Analysed by High Throughput Frequency Domain Fluorescence Lifetime Imaging Microscopy (f-FLIM) in Cells The interaction between PD-1 and PD-L1 in cells was determined using the following assay. The experiments were performed in the presence and anti-PD-1 antibody using 8 well plates as shown in Table 1.

TABLE 1

PD-1: PD-L1 blockade assay in 8 well plates in the presence and absence of 25 μg/ml anti-PD-1 antibody)

| | % of mAb Blocking interaction | | | |
|---|---|---|---|---|
| | 0% | 0% | 100% | 100% |
| Donor | Well 1 | Well 2 | Well 3 | Well 4 |
| Donor/Acceptor | Well 5 | Well 6 | Well 7 | Well 8 |

PD-L1 APC/CHO-K1 cells were added to the 8 well plates and incubated for 19 hours in a 37° C., 5% $CO_2$ incubator. The medium was removed and 25 μg/ml of blocking anti-PD-1 antibody was added to half of the plate while assay buffer was added to the rest. PD-1 Effector Cells (Jurkat) were added and incubated for 22 h in a 37° C., 5% $CO_2$ incubator.

The unbound cells were removed, and the plates were washed twice with PBS. The cells were fixed with 4% PFA, washed again twice with PBS and stored at 4° C. in PBS. The cells were not permeablised with any detergent prior to antibody treatment.

Fret Protocol:

Endogenous peroxidases were quenched using an endogenous peroxidase suppressor for 30 min at room temperature. Wells were washed twice with PBS, blocked with BSA 1% for 1 hour at room temperature and washed twice with PBS.

The wells were incubated overnight at 4° C. with 80 μl of primary antibody against PD-1 (1:100) in BSA 1% and in the case of the donor/acceptor conditions they were simultaneously incubated with primary antibody against PD-L1 (1:500). The plates were washed twice with PBS-Tween 0.02%.

The donor only conditions were labelled with secondary anti-mouse FabATTO 488 (1:100) while the donor/acceptor conditions were labelled with both secondary anti-mouse FabATTO 488 (1:100) and anti-rabbit Fab-HRP (1:200). The Fab fragments were incubated in both conditions for 2 hours. The plates were washed twice with PBS-Tween 0.02% and tyramide signal amplification was utilised for the amplification of the acceptor. The slide was then mounted. A monoclonal blocking antibody to promote the disruption of the interaction was used as a negative control.

Time Resolved FRET Acquisition:

An automated multiple frequency high-throughput lifetime imaging microscope was created by modifying a multiple frequency domain FLIM lifetime imaging microscope from Lambert Instruments.

The FRET efficiency ($E_f$) was determined using the following formula: $E_f(\%) = [1-(t_{D/A}/t_D)]100$; where (upon FRET $t_{D/A} \ll t_D$); $t_D$ is donor lifetime and $t_{D/A}$ is the donor plus acceptor lifetime.

The data acquisition was performed using the 60× oil objective (N/A 1.49), and the donor lifetimes and intensities of ATTO 488 were determined at a peak power of 70 mW using a modulated 473 nm laser beam at 40 MHz and an exposure time of 70 ms with a threshold of 35%. For the acceptor intensity acquisition the mercury source with a TRITC excitation/emission filter, was used for 1 ms with an 8 times neutral density filter.

Figure 3:
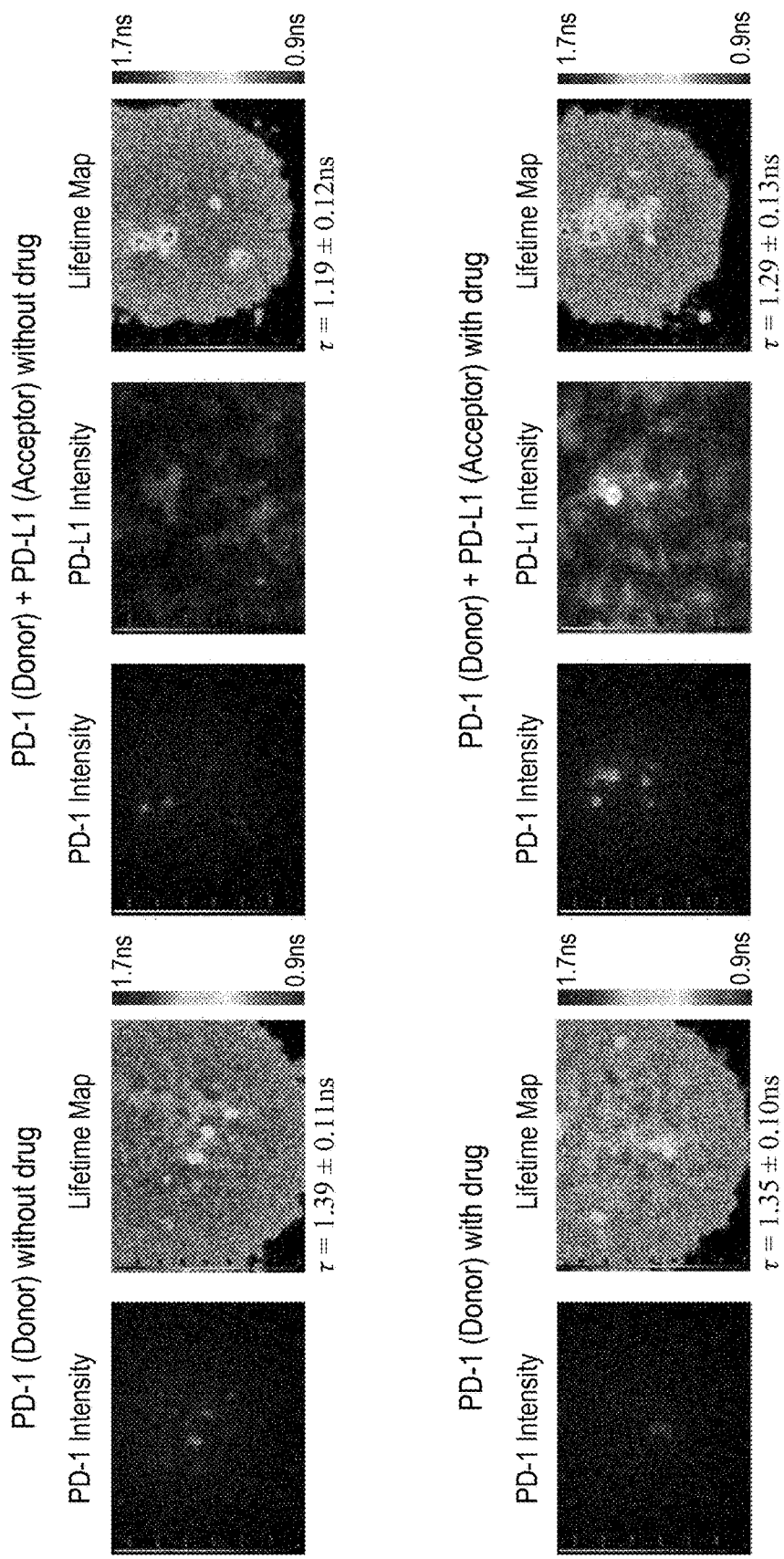
FIG. 3 shows representative intensity and lifetime images for PD-1 only and PD-1: PD-L1 in the presence and absence of a blocking monoclonal binding agent.

Data Analysis:

The results are shown in FIGS. 3 and 4. The upper panel of FIG. 3 shows the donor lifetime decreases from 1.39 to 1.19 ns in the presence of the acceptor PD-L1. This reduction in the lifetime is due to the interaction of these two proteins. In the presence of the blocking antibody the lifetime of the donor (with the acceptor) is 1.29 ns. Thus, the donor lifetime with blocking antibody does not decrease to the same extent.

The FRET efficiencies were calculated from the changes in the donor life times in the presence of acceptor, with and without blocking antibody, and plotted as box and whiskers distributions, as shown in FIG. 4.

FIG. 4 shows that PD-1:PD-L1 interaction can be quantified by FRET. The data shows highly significant differences between the receptor and the ligand interaction and its inhibition with the blocking antibody. Each point on the Box and Whiskers plots was a region of interest containing an average of 5 cells. The P value was determined by a Mann-Whitney non parametric test.

The results show that the methods of the invention allow quantification of molecular interactions, such as PD-1 and PD-L1 interaction in cells, and that differences in the molecular interactions can be detected following drug treatment.

Example 3—i-FRET Assay for CTLA-4 and CD80 Interaction in Cell Culture

The Promega Blockade Bioassay (CS186907) protocol, originally designed to measure the antibody blockade of Cytotoxic T-Lymphocyte Antigen 4 and cluster of differentiation 80 interaction (CTLA-4-CD80) by luminescence, was adapted for an i-FRET protocol.

Plate Preparation

CTLA-4-expressing Jurkat cells, provided by the Promega blockade bioassay, were seeded at 100 μl/well onto a Millicell® 8-well plate. Anti-CTLA-4 antibody (ipilimumab), acquired from Qualasept, was added to half of the wells to give a final concentration of 100 μl/ml (Table 1). 100 μl of CD80-expressing Raji cells were added to each well and the plate was incubated 19 hours at 37° C. and 5% $CO_2$. Unbound cells were removed by PBS wash and the cells fixed with 4% paraformaldehyde (PFA) for 12 minutes. PFA was removed and all wells washed with PBS.

TABLE 2

Design of Millicell ® 8-well plate. Wells 1-4 represent the donor only condition while wells 5-8 represent the donor/acceptor condition. Culture medium was added to wells 1, 2, 5 and 6 and 100 µl/ml anti-CTLA-4 antibody, ipilimumab, to wells 3, 4, 7 and 8.

| | Ipilimumab (µl/ml) | | | |
|---|---|---|---|---|
| Condition | 0 | 0 | 100 | 100 |
| Donor | Well 1 | Well 2 | Well 3 | Well 4 |
| Donor/Acceptor | Well 5 | Well 6 | Well 7 | Well 8 |

Primary Antibody Staining with Anti-CTLA-4 and Anti-CD80

Pierce Endogenous Peroxidase Suppressor, from Thermo Fisher Scientific, was added to each well and incubated for 30 minutes at room temperature. Cells were washed with PBS, incubated for 1 hour with 1% (10 mg/ml) Bovine Serum Albumin (BSA) and washed again with PBS. Primary antibody staining was carried out using mouse monoclonal anti-CTLA-4 and rabbit polyclonal anti-CD80, acquired from Abcam and MyBioSource respectively. Both were diluted (1:100) in BSA. Anti-CTLA-4 was used to label the donor only condition (1-4) while both anti-CTLA-4 and anti-CD80 were used to label the donor/acceptor condition (5-8). The plate was incubated overnight at 4° C. before being washed twice with 0.02% Tween20 in PBS (PBST) and once with PBS.

Secondary Staining with Anti-Mouse Fab-ATTO488 and Anti-Rabbit Fab-HRP

The secondary FabATTO488 was diluted (1:15) using 1% BSA and added to both the donor and donor/acceptor wells (1-8). FabATTO488 conjugation contained 4.1 molecules of ATTO488 per molecule of Fab fragment protein. Secondary FabHRP was diluted (1:200) using 1% BSA and added to the donor/acceptor wells only (5-8). The plate was incubated for 2 hours before being washed twice with 0.02% PBST and once with PBS.

Tyramide Amplification

Alexa594 conjugated tyramide was diluted in amplification buffer (1:100) in the presence of 0.15% H2O2. Of this mixture, 100 µl was added to each donor/acceptor well (5-8) and the plate was incubated in darkness for 20 minutes. To remove Tyramide, wells were washed twice with PBST and once with PBS. 5 µl of Prolong Diamond anti-fade mount was added to each well and mounted using a coverslip.

CTLA-4-CD80 Interaction Determined Using i-FRET

Figure 5:
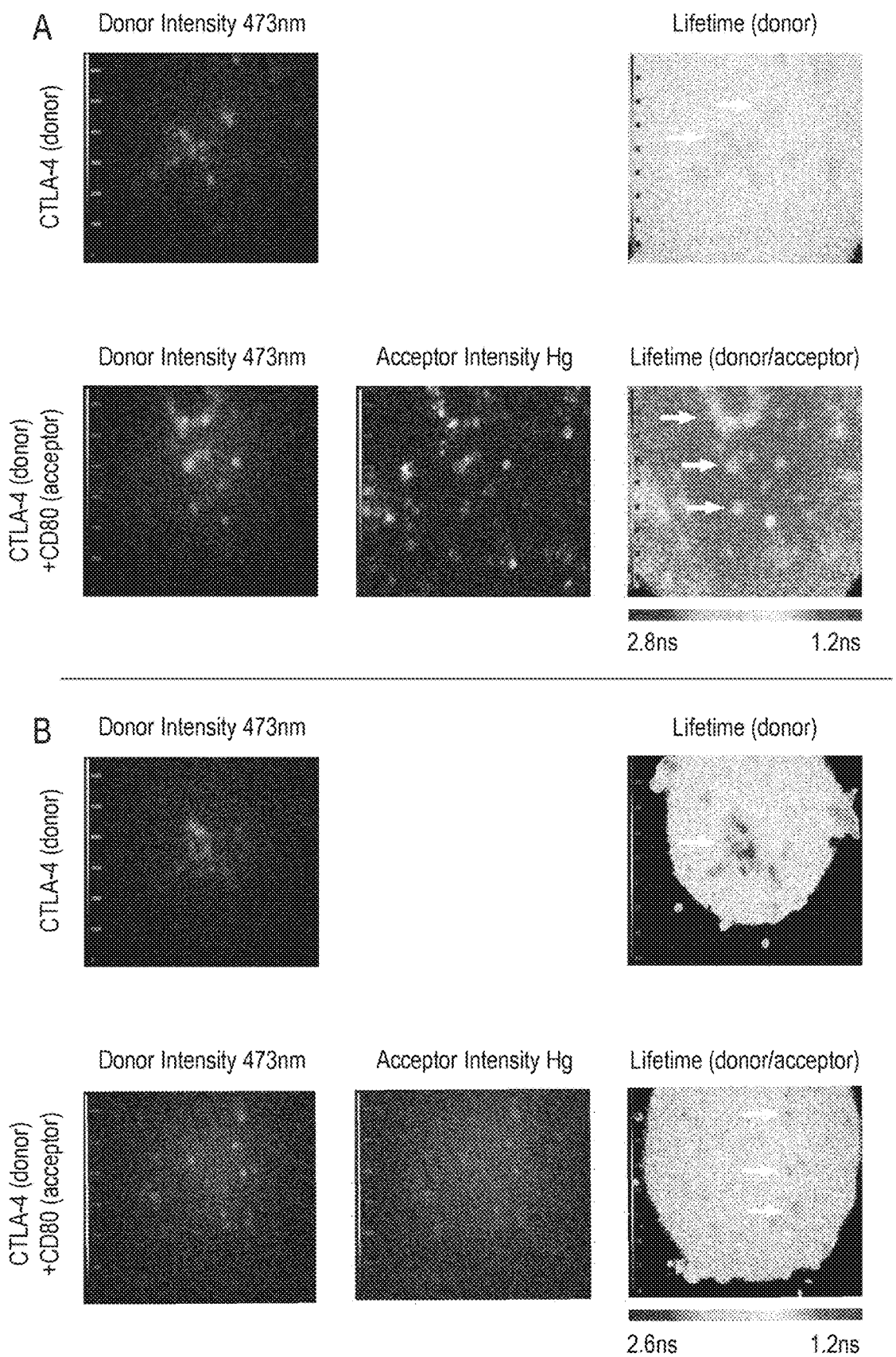
FIG. 5 shows variations in CTLA-4: CD80 interactions in single cells in the absence or presence of the anti-CTLA-4 antibody ipilimumab.

Intercellular CTLA-4-CD80 interaction was assessed using Förster resonance energy transfer (FRET). CTLA-4 and CD80 intensities were determined using a modulated 473 nm laser beam at 40 MHz and a mercury source respectively. CTLA-4 intensity, CD80 intensity and lifetime maps are displayed in FIG. 5. When comparing donor only to donor/acceptor wells, a greater decrease in the donor lifetime ($\tau$) is observed in the no treatment condition compared to the 100 µl ipilimumab condition.

FRET efficiency values (FIG. 6) were significantly (***) higher (p=0.00044, p=0.00024) in 0 µl/ml ipilimumab condition compared to 100 µl/ml ipilimumab condition. FRET values were not significantly different (p=0.054) between wells containing no ipilimumab.

Conclusions

1) Cell-cell contact can be quantified by i-FRET using the CTLA-4-CD80 pair.
2) FRET efficiency decreases significantly in the presence of ipilimumab compared to untreated cells.
3) FRET Efficiency values decreased in the 100l/ml ipilimumab condition, which strongly suggests that the interaction observed in the absence of ipilimumab was due to the specific interaction between CTLA-4 and CD80.

Example 4—iFRET Assay for CTLA-4 and CD80 Interaction in Metastatic Melanoma Tissue Immune-Förster resonance energy transfer (i-FRET) assay determining cytotoxic T-lymphocyte associated protein-4 (CTLA-4) and cluster of differentiation 80 (CD80) interaction was carried out on metastatic melanoma tissue. Samples were obtained from different patients as detailed in Table 3 (below).

Methods

Antigen Retrieval

Antigen retrieval was carried out at Fastbase laboratory using a PTLink before adding 1-2 drops/slide of Pierce Endogenous Peroxidase Suppressor to quench endogenous peroxidases and incubated for 30 minutes. 300 µl of 10 mg/ml Bovine Serum Albumin (BSA), diluted in phosphate buffered saline (PBS), was then added to each slide in order to prevent non-specific primary antibody binding. Both incubations were carried out in a humidified tray.

Primary Antibody Staining

Primary antibody staining was carried out using mouse monoclonal anti-CTLA-4 and rabbit polyclonal anti-CD80. Both were diluted (1:100) in 1% BSA in PBS. Anti-CTLA-4 was used to label the donor only condition while both anti-CTLA-4 and anti-CD80 were used to label the donor/acceptor condition. 150 µl was added to each slide before being incubated overnight.

Secondary Antibody Staining

Donor only slides were incubated with anti-mouse Fab-ATTO488 (1:15) final dilution and donor acceptor slides with anti-mouse Fab-ATTO488 (1:15)+anti-rabbit Fab-HRP (1:200). Dilutions were made using 1% BSA in PBS. 150 µl was added to each slide before being incubated for 2 hours at room temperature in a humidified tray.

Tyramide Labelling

Alexa594 conjugated tyramide was diluted in amplification buffer (1:100) in the presence of 0.15% H2O2. Of this mixture, 150 µl was added to each donor/acceptor slide and incubated at room temperature in darkness for 20 minutes. 150 µl of Prolong Diamond anti-fade mount was added to each slide and mounted using a coverslip.

Haematoxylin and Eosin Staining

Haematoxylin and eosin (H&E) staining was carried out on additionally provided slides of corresponding samples. H&E staining allowed pathological analysis in order to identify areas of immune cell infiltration. Selected areas were the focus for i-FRET analysis in this assay.

Table 3 shows the patient background of the samples used for this assay, including genetic background, details of past and active treatment and sample origin.

TABLE 3

Patient background.

| Patient | Details |
|---|---|
| MM14 | 82 year old female with stage 4 mucosal melanoma.<br>v-RAF murine sarcoma viral oncogene homolog B (B-RAF) wild type.<br>c-KIT mutant. c-KIT is a cell surface receptor tyrosine kinase which activates signalling pathways, such as the mitogen activated protein kinase pathway (MAPK), and signalling proteins including protein kinase B (AKT) and phospholipase C gamma (PLCγ). The mutant version of c-KIT has undergone an oncogenic mutation, increasing its activity. Hyperadivation of the MAPK pathway can lead to uncontrolled cell growth and proliferation by changes in protein activation and expression within the cell. AKT is a component of the phosphoinositide 3-kinase (PI3K) pathway which activates cell growth.<br>No active therapy.<br>Patient was previously treated with nilotinib, a tyrosine kinase inhibitor.<br>Tissue was a lymph node metastasis. |
| MM17 | 61 year old male with stage 4 cutaneous melanoma.<br>B-RAF wild type.<br>No active therapy<br>Prior treatment with ipilimumab (anti-cytotoxic T-lymphocyte associated protein-4) and nivolumab (anti-programmed death receptor-1). Tissue was a lymph node metastasis. |
| MM19 | 49 year old male with stage 4 cutaneous melanoma.<br>B-RAF wild type.<br>Neuroblastoma RAS viral oncogene homolog (NRAS) mutant. The NRAS gene codes for a small guanine triphosphate binding protein) which is a component on the MAPK pathway. An oncogenic mutation of NRAS causes the hyperactivation of the MAPK pathway.<br>Treatment naïve.<br>Tissues were a lymph node metastasis and a transverse colon metastasis. |

FIG. 6 shows that the interaction between CTLA-4 and CD80 can be measured by FRET in metastatic melanoma tissue.

Example 5—Detecting Cell-Cell Contact in Renal Cell Carcinomas Using i-FRET and PD-1/PD-L1 Pair Immune-Förster resonance energy transfer (i-FRET) assay determining programmed death receptor-1 (PD-1) and programmed death-ligand 1 (PD-L1) interaction, and thus cell-cell contact, was carried out on renal cell carcinoma tissue. Samples were obtained from different patients and include a variety of renal cell carcinomas, namely clear cell renal cell carcinoma (ccRCC), papillary renal cell carcinoma (PRCC) and chromophobe renal cell carcinoma (ChRCC). All samples were primary tumours.

Methods

Antigen Retrieval

Antigen retrieval was carried out at Fastbase laboratory using a PTLink before adding 1-2 drops/slide of Pierce Endogenous Peroxidase Suppressor to quench endogenous peroxidases and incubated for 30 minutes. 300 µl of 10 mg/ml Bovine Serum Albumin (BSA), diluted in phosphate buffered saline (PBS), was then added to each slide in order to prevent non-specific primary antibody binding. Both incubations were carried out in a humidified tray.

Primary Antibody Staining

Primary antibody staining was carried out using mouse monoclonal anti-PD-1 and rabbit monoclonal anti-PD-L1 diluted (1:100) and (1:500) respectively in 1% BSA in PBS. Anti-PD-1 was used to label the donor only condition while both anti-PD-1 and anti-PD-L1 were used to label the donor/acceptor condition. 150 µl was added to each slide before being incubated overnight.

Secondary Antibody Staining

Donor only slides were incubated with anti-mouse Fab-ATTO488 (1:15) final dilution and donor acceptor slides with anti-mouse Fab-ATTO488 (1:15)+anti-rabbit Fab-HRP (1:200). Dilutions were made using 1% BSA in PBS. 150 µl was added to each slide before being incubated for 2 hours at room temperature in a humidified tray.

Tyramide Labelling

Alexa594 conjugated tyramide was diluted in amplification buffer (1:100) in the presence of 0.15% H2O2. Of this mixture, 150 µl was added to each donor/acceptor slide and incubated at room temperature in darkness for 20 minutes. 150 µl of Prolong Diamond anti-fade mount was added to each slide and mounted using a coverslip.

Figure 7:
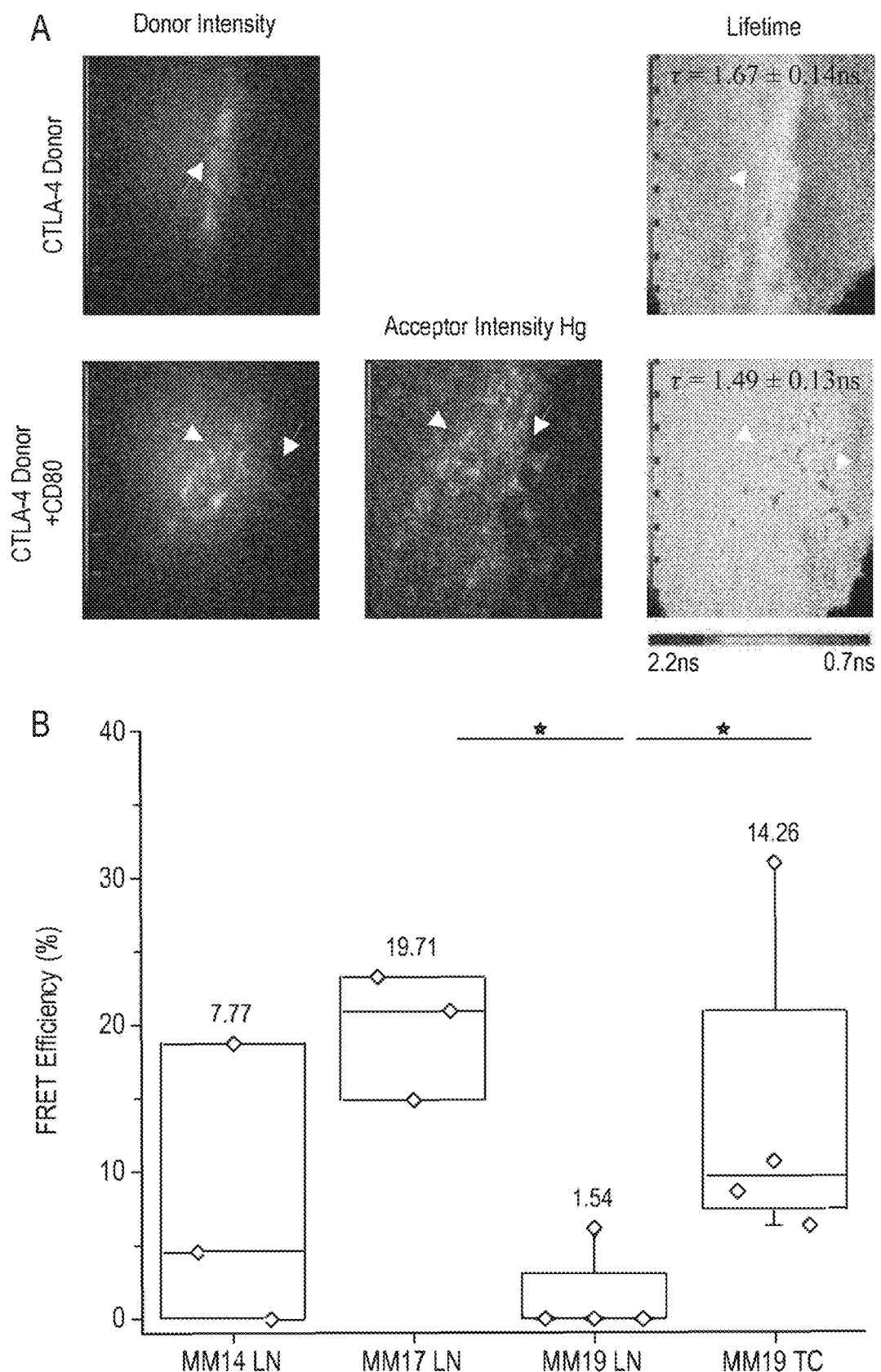
FIG. 7 shows variations in CTLA-4-CD80 interactions in metastatic melanoma tissue in the absence or presence of the anti-CTLA-4 antibody ipilimumab (A) and the quantification of each result for each sample (B).

The results of the above example are shown in FIG. 7.

Example 6—Detecting Cell-Cell Interaction in ccRCC Tissue Using i-FRET and PD-1/PD-L1 Pair Immune-Förster resonance energy transfer (i-FRET) assay determining programmed death receptor-1 (PD-1) and programmed death-ligand 1 (PD-L1) interaction, and thus cell-cell interaction, was carried out on clear cell renal cell carcinoma (ccRCC) tissue. Samples were obtained from Cruces Hospital, Bilbao. Prior to the assay, samples were determined PD-L1+/+ or PD-L1 −/−.

Methods

Antigen Retrieval

Antigen retrieval was carried out at FASTBASE SOLUTIONS laboratory using a PTLink before adding 1-2 drops/slide of Pierce Endogenous Peroxidase Suppressor to quench endogenous peroxidases and incubated for 30 minutes. 300 µl of 10 mg/ml bovine serum albumin (BSA) in phosphate buffered saline (PBS) was then added to each slide in order to prevent non-specific primary antibody binding. Both incubations were carried out in a humidified tray.

Primary Antibody Labelling

Primary antibody labelling was carried out using mouse monoclonal anti-PD-1 and rabbit monoclonal anti-PD-L1 diluted (1:100) and (1:500) respectively in 1% BSA in PBS. Anti-PD-1 was used to label the donor only condition while both anti-PD-1 and anti-PD-L1 were used to label the donor/acceptor condition. 150 μl was added to each slide before being incubated overnight.

Secondary Antibody Labelling

Donor only slides were incubated with anti-mouse Fab-ATTO488 (1:15) final dilution and donor acceptor slides with anti-mouse Fab-ATTO488 (1:15)+anti-rabbit Fab-HRP (1:200). Dilutions were made using 1% BSA in PBS. 150 μl was added to each slide before being incubated for 2 hours at room temperature in a humidified tray.

Tyramide Labelling

Alexa594 conjugated tyramide was diluted in amplification buffer (1:100) in the presence of 0.15% H2O2. Of this mixture, 150 μl was added to each donor/acceptor slide and incubated at room temperature in darkness for 20 minutes. 150 μl of Prolong Diamond anti-fade mount was added to each slide and mounted using a coverslip.

The results of the above example are shown in FIG. 8 and shows that i-FRET determines the specific interaction of PD-1 and PD-L1 in infiltrated regions with low PD-L1 expression. This is not the case when using PLA, where the proximity of PD-1 and PD-L1 cannot be detected at low PD-L1 expression. Moreover, the heterogeneity of the infiltrated regions can be quantified by i-FRET. The precision of i-FRET allows the identification of outliers, possibly excluded by other methods for therapeutic treatment.

Example 7—Two Site TSA-FRET Analysed by High Throughput Frequency Domain Fluorescence Lifetime Imaging Microscopy (f-FLIM) in Fixed Tissue Sections T-cells recognise antigens by interaction of T Cell Receptor (TCR) with peptides embedded in MHC molecules (pMHC) on the surface of Antigen Presenting Cells (APCs). Cytotoxic T lymphocyte TCRs recognise epitopes displayed by MHC class I molecules on the surface of cells in the body in order to distinguish between 'self'-antigens and foreign antigens (viral-infected cells), as well as neo antigens presented by tumour cells. Helper T cell TCRs recognise epitopes displayed by MHC class II molecules on the surface of antigen-presenting immune cells. TCRs on other type of T cells also interact with MHC-like molecules from the CD1d family—e.g. interaction between the semi-invariant TCR expressed by invariant NKT cells and CD1d-lipid complexes, interaction of TCR expressed by Mucosal-associated invariant T cells (MAIT cells) and MHC like molecule MR1 (Bhati et al, 2013). The TCR interacts with CD3 molecules to form the TCR complex. CD3 contains 3 distinct polypeptide chains: $\gamma$, $\varepsilon$, and $\delta$. The TCR complex may also further interact with CD4 or CD8 molecule depending on the type of T cell expressing the TCR.

In the methods, kits and uses of the invention, the first molecule can be the TCR or other members of the TCR complex including CD3$\gamma$, CD3$\varepsilon$, and CD3$\delta$ or CD8 or CD4 and combinations thereof 1 and the second molecule can be an antigen loaded MHC Class I, MHC Class II or MHC like molecules such as CD1d or MR.

Measurement of TCR-pMHC interaction has been hitherto accomplished by FRET using recombinant pMHC complexes (Huang et al 2010) or MHC bound to fluorescent peptide (Axmann et al, 2015). However, there is a lack of methods for measurement of interaction endogenously expressed TCR-pMHC on fixed tissues.

In the methods, kits and uses of the invention, the first molecule can be endogenously expressed TCR or other members of the TCR complex including CD3$\gamma$, CD3$\varepsilon$, and CD3$\delta$ or CD8 or CD4 and combinations thereof and the second molecule can be an endogenously expressed antigen loaded MHC Class I, MHC Class II or MHC like molecules such as CD1d or MR1.

For the TCR-pMHC interaction studies, FFPE sections are covered and heated with Tris-EDTA buffer and are subsequently treated according to methods described in Example 1.

The tissue sections were then split into two conditions: donor only (D) and donor and acceptor (D/A). The two primary antibodies used are, for example, mouse anti-TCR and rabbit anti-MHC, diluted 1:100 and 1:500, respectively, in 1% BSA/PBS buffer. Donor only conditions are incubated with mouse anti-TCR antibody, while donor and acceptor conditions were incubated with both mouse Anti-TCR and rabbit anti-MHC.

In the present specification "comprises" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention will now be defined by reference to the following clauses:

1. An in vitro coincidence assay method for detecting the interaction between a first molecule expressed on a first cell and a second molecule expressed on a second cell, the method comprising:
   at least two primary antibodies, wherein the first primary antibody binds to the first molecule on the first cell and the second primary antibody binds to the second molecule on the second cell, and wherein the first and secondary primary antibodies are immunologically distinct;
   at least two secondary antibodies, wherein a first secondary antibody binds to the first primary antibody; and a second secondary antibody binds the second primary antibody, wherein the first secondary antibody does not bind the second primary antibody and the second secondary antibody does not bind the first primary antibody; and wherein:
   (i) the first secondary antibody is labelled with a FRET donor and the second secondary antibody is labelled with a FRET acceptor;
   (ii) the first and second secondary antibodies are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
   (iii) the first secondary antibody is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
(a) contacting an isolated sample containing cells with the at least two primary antibodies;
(b) contacting the sample with the at least two secondary antibodies;
(c) performing a wash step;
(d) detecting the interaction between the secondary antibodies.

2. The method of clause 1, wherein detecting the interaction between the secondary antibodies is by detecting the emitted fluorescence.

3. The method of clause 1, wherein detecting the interaction between the secondary antibodies is by detecting the altered fluorescence behaviour.

4. The method of clause 3, wherein detecting the altered fluorescence behaviour is time-resolved.

5. The method according to clause 1, wherein the first cell and the second cell are the same type of cell.

6. The method according to clause 1, wherein the first cell and the second cell are not the same type of cell.

7. The method according to clause 1, wherein the isolated sample is a fixed cell sample.

8. The method according to clause 7, wherein the isolated sample is a fixed tumour cell sample.

9. The method according to any preceding clause wherein the first and second molecules are proteins, preferably endogenous proteins.

10. The method according to clause 9, wherein the proteins are immune checkpoint proteins.

11. The method according to clause 9 or 10, wherein the first molecule is PD-1 and the second molecule is PD-L1 or PD-L2.

12. The method according to clause 9 or 10, wherein the first molecule is CTLA-4 or CD28 and the second molecule is CD80 or CD86.

13. The method according to clause 9 or 10, wherein the first molecule is selected from an MHC Class I or II peptide and the second molecule is selected from TCR, CD8, CD3 and combinations thereof.

14. The method according to any preceding clause, wherein the at least two primary antibodies are selected from the group consisting of whole immunoglobulins, antibody or antigen-binding fragments thereof or combinations thereof.

15. The method according to any preceding clause, wherein at least one of the secondary antibodies is an antibody or antigen-binding fragment.

16. The method according to any preceding clause, wherein the at least two secondary antibodies are antibody or antigen-binding fragments.

17. The method according to any preceding clause, wherein the antibody or antigen-binding fragments are Fab fragments, scFv fragments or combinations thereof.

18. The method according to any preceding clause, wherein the primary antibodies are unlabelled.

19. The method according to any preceding clause, wherein the first primary antibody is a murine antibody and the at least one other primary antibody is a rabbit antibody.

20. The method according to clause 11, wherein the first primary antibody binds to PD-1 and the at least one other primary antibody binds to PD-L1 or PD-L2.

21. The method according to clause 12, wherein the first primary antibody binds to CTLA-4 or CD28 and the second primary antibody binds to either CD80 or CD86.

22. The method according to clause 13, wherein the first primary antibody binds to MHC Class I or II peptide and the at least one other primary antibody binds to TCR, CD8, CD3 or a combination thereof.

23. The method according to clause 19, wherein the first secondary antibody is an anti-murine antibody and the at least one other secondary antibody is an anti-rabbit antibody.

24. The method according to any of the preceding clauses, wherein the FRET donor is selected from the group consisting of ORG 488, GFP, fluorescein, IAEDANS, EDANS, BODIPY FL, ATTO488 and combinations thereof.

25. The method according to any of the preceding clauses, wherein the FRET acceptor is selected from the group consisting of: ALX 594, mRFP, tetramethylrhodamine, fluorescein, dabcyl, BODIPY FL, QSY 7, QSY 9 and combinations thereof.

26. The method according any of the preceding clauses, wherein the enzyme is selected from the group consisting of oxidoreductases, hydrolases, lyases, transferases, isomerases, and ligases.

27. The method according to clause 26, wherein the enzyme is selected from the group consisting of peroxidases, oxidases, phosphatases, esterases and glycosidases.

28. The method according to clause 27, wherein the enzyme is selected from the group consisting of horseradish peroxidase, glucose oxidase, alkaline phosphatase and beta-galactosidase.

29. The method according to any of the preceding clauses, wherein the substrate is tyramide.

30. The method according to any of the preceding clauses, wherein the first cell is a T-cell and the second cell is a tumour cell.

31. The method according to any preceding clause, wherein the at least two primary antibodies are contacted simultaneously or sequentially to one another.

32. The method according to any preceding clause, wherein the at least two secondary antibodies are contacted simultaneously or sequentially to one another.

33. The method according to clauses 1 to 31, wherein the at least two primary antibodies are contacted with the sample simultaneously to the at least two secondary antibodies.

34. The method according to clauses 1 to 31, wherein the at least two primary antibodies are contacted with the sample before the at least two secondary antibodies.

35. The method according to clause 34, wherein a wash step is performed after the at least two primary antibodies are contacted with the sample and before the at least two secondary antibodies are contacted with the sample.

36. The method according to any preceding clause, the method further comprising the step of quantifying the interaction between the first site on the first cell and the second site on the second cell.

37. The method according to any preceding clause, wherein the first cell is a lymphocyte and the second cell is a non-lymphocyte cell type.

38. The method of clause 37, wherein the method detects the interaction between PD-1 on the first lymphocyte cell and PD-L1 or PD-L2 on the second non-lymphocyte cell.

39. The method of any preceding clause, wherein the first molecule is located on the cell surface of the first cell and the second molecule is located on the cell surface of the second cell.

40. The method of any preceding clause, wherein the at least two primary antibodies bind to the first molecule or second molecule in such a manner that the checkpoint inhibitor or activator can bind to the first molecule or second molecule at the same time or subsequently.

41. The method of any preceding clause, wherein the at least two primary antibodies do not inhibit the binding of a checkpoint inhibitor or activator to the first molecule or the second molecule.

42. Use of the in vitro coincidence assay method according to any preceding clause for detecting the interaction between a first molecule expressed on a first cell and a second molecule expressed on a second cell.

43. A kit for use in an in vitro coincidence assay method for detecting the interaction between a first molecule expressed on a first cell and a second molecule expressed on a second cell, the kit comprising:
   a) at least two primary antibodies, wherein the first primary antibody binds to the first molecule on the first cell and the second primary antibody binds to the second molecule on the second cell, and wherein the first and secondary primary antibodies are immunologically distinct;
   b) at least two secondary antibodies, wherein a first secondary antibody binds to the first primary antibody; and a second secondary antibody binds the second primary antibody, wherein the first secondary antibody does not bind the second primary antibody and the second secondary antibody does not bind the first primary antibody; and wherein:
      (i) the first secondary antibody is labelled with a FRET donor and the second secondary antibody is labelled with a FRET acceptor;
      (ii) the first and second secondary antibodies are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
      (iii) the first secondary antibody is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme;
   c) instructions for performing a method comprising:
      i. contacting an isolated sample containing cells with the at least two primary antibodies;
      ii. contacting the sample with the at least two secondary antibodies;
      iii. performing a wash step;
      iv. detecting the interaction between the secondary antibodies.

44. The kit for the use according to clause 43, wherein the instructions for detecting the interaction between the secondary antibodies are for detection by detecting the emitted fluorescence.

45. The kit for the use according to clause 43, wherein the instructions for detecting the interaction between the secondary antibodies are for detection by detecting the altered fluorescence behaviour.

46. The kit for the use according to clause 45, wherein detecting the altered fluorescence behaviour is time-resolved.

47. The kit for the use according to clause 43, wherein the first cell and the second cell are the same type of cell.

48. The kit for the use according to clause 43, wherein the first cell and the second cell are not the same type of cell.

49. The kit for the use according to clause 43, wherein the isolated sample is a fixed cell sample.

50. The kit for the use according to clause 49, wherein the isolated sample is a fixed tumour cell sample.

51. The kit for the use according to any preceding clause, wherein the first and second molecules are proteins, preferably endogenous proteins.

52. The kit for the use according to clause 51, wherein the proteins are immune checkpoint proteins.

53. The kit for the use according to clause 51 or 52, wherein the first molecule is PD-1 and the second molecule is PD-L1 or PD-L2.

54. The kit for the use according to clause 51 or 52, wherein the first molecule is CTLA-4 or CD28 and the second molecule is CD80 or CD86.

55. The kit for the use according to clause 51 or 52, wherein the first molecule is an MHC Class I or II peptide and the second molecule is selected from TCR, CD8, CD3 and combinations thereof.

56. The kit for the use according to any preceding clause, wherein the at least two primary antibodies are selected from the group consisting of whole immunoglobulins, antibody or antigen-binding fragments thereof or combinations thereof.

57. The kit for the use according to any preceding clause, wherein at least one of the secondary antibodies is an antibody or antigen-binding fragment.

58. The kit for the use according to any preceding clause, wherein the at least two secondary antibodies are antibody or antigen-binding fragments.

59. The kit for the use according to any preceding clause, wherein the antibody or antigen-binding fragments are Fab fragments, scFv fragments or combinations thereof.

60. The kit for the use according to any preceding clause, wherein the primary antibodies are unlabelled.

61. The kit for the use according to any preceding clause, wherein the first primary antibody is a murine antibody and the at least one other primary antibody is a rabbit antibody.

62. The kit for the use according to clause 53, wherein the first primary antibody binds to PD-1 and the at least one other primary antibody binds to PD-L1 or PD-L2.

63. The kit for the use according to clause 54, wherein the first primary antibody binds to CTLA-4 or CD28 and the second primary antibody binds to either CD80 or CD86.

64. The kit for the use according to clause 55, wherein the first primary antibody binds to an MHC Class I or II peptide and the second primary antibody binds to TCR, CD8, CD3 and combinations thereof.

65. The kit for the use according to clause 61, wherein the first secondary antibody is an anti-murine antibody and the at least one other secondary antibody is an anti-rabbit antibody.

66. The kit for the use according to any of the preceding clauses, wherein the FRET donor is selected from the group consisting of ORG 488, GFP, fluorescein, IAE-DANS, EDANS, BODIPY FL, ATTO488 and combinations thereof.
67. The kit for the use according to any of the preceding clauses, wherein the FRET acceptor is selected from the group consisting of: ALX 594, mRFP, tetramethylrhodamine, fluorescein, dabcyl, BODIPY FL, QSY 7, QSY 9 and combinations thereof.
68. The kit for the use according any of the preceding clauses, wherein the enzyme is selected from the group consisting of oxidoreductases, hydrolases, lyases, transferases, isomerases, and ligases.
69. The kit for the use according to clause 68, wherein the enzyme is selected from the group consisting of peroxidases, oxidases, phosphatases, esterases and glycosidases.
70. The kit for the use according to clause 69, wherein the enzyme is selected from the group consisting of horseradish peroxidase, glucose oxidase, alkaline phosphatase and beta-galactosidase.
71. The kit for the use according to any of the preceding clauses, wherein the substrate is tyramide.
72. The kit for the use according to any of the preceding clauses, wherein the first cell is a T-cell and the second cell is a tumour cell.
73. The kit for the use according to any preceding clause, wherein the instructions provide for contacting the at least two primary antibodies simultaneously or sequentially to one another.
74. The kit for the use according to any preceding clause, wherein the instructions provide for contacting the at least two secondary antibodies simultaneously or sequentially to one another.
75. The kit for the use according to clauses 43 to 73, wherein the instructions provide for contacting the at least two primary antibodies with the sample simultaneously to the at least two secondary antibodies.
76. The kit for the use according to clauses 43 to 73, wherein the instructions provide for contacting the at least two primary antibodies with the sample before the at least two secondary antibodies.
77. The kit for the use according to clause 76, wherein the instructions provide for performing a wash step after the at least two primary antibodies are contacted with the sample and before the at least two secondary antibodies are contacted with the sample.
78. The kit for the use according to any preceding clause, the instructions provide a method further comprising the step of quantifying the interaction between the first site on the first cell and the second site on the second cell.
79. The kit for the use according to any preceding clause, wherein the first cell is a lymphocyte and the second cell is a non-lymphocyte cell type.
80. The kit for the use of clause 79, wherein the instructions provide for a method that detects the interaction between PD-1 on the first lymphocyte cell and PD-L1 or PD-L2 on the second non-lymphocyte cell.
81. The kit for the use of any preceding clause, wherein the first molecule is located on the cell surface of the first cell and the second molecule is located on the cell surface of the second cell.
82. The kit for the use of any preceding clause, wherein the at least two primary antibodies bind to the first molecule or second molecule in such a manner that the checkpoint inhibitor or activator can bind to the first molecule or second molecule at the same time or subsequently.
83. The kit for the use of any preceding clause, wherein the at least two primary antibodies do not inhibit the binding of an inhibitor or activator to the first molecule or the second molecule.
84. Use of the kit of any of clauses 43 to 83 in an in vitro coincidence assay method for detecting the interaction between a first molecule expressed on a first cell and a second molecule expressed on a second cell.
85. A method of selecting a patient with cancer for treatment, the method comprising:
  at least two primary antibodies, wherein the first primary antibody binds to a first checkpoint target molecule on the first cell and the second primary antibody binds to a second checkpoint target molecule on the second cell, and wherein the first and secondary primary antibodies are immunologically distinct;
  at least two secondary antibodies, wherein a first secondary antibody binds to the first primary antibody; and a second secondary antibody binds the second primary antibody, wherein the first secondary antibody does not bind the second primary antibody and the second secondary antibody does not bind the first primary antibody; and wherein:
    (i) the first secondary antibody is labelled with a FRET donor and the second secondary antibody is labelled with a FRET acceptor;
    (ii) the first and second secondary antibodies are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
    (iii) the first secondary antibody is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme;
  wherein the method comprises:
    (a) contacting an isolated tumour cell sample from the patient with the at least two primary antibodies;
    (b) contacting the sample with the at least two secondary antibodies;
    (c) performing a wash step;
    (d) detecting the interaction between the secondary antibodies by determining the overall fluorescence score;
  wherein:
    a. where the intended therapy comprises a checkpoint activator targeting at least one of the first and second checkpoint target molecules:
      i. if the overall score is less than or equal to a threshold score, the overall score indicates or predicts that the patient will respond to the intended therapy; or
      ii. if the overall score is greater than a threshold score, the overall score indicates or predicts that the patient will not respond to the intended therapy; or
    b. where the intended therapy comprises a checkpoint inhibitor targeting at least one of the first and second checkpoint target molecules:

(i) if the overall score is less than or equal to a threshold score, the overall score indicates or predicts that the patient will not respond to the intended therapy; or
(ii) if the overall score is greater than a threshold score, the overall score indicates or predicts that the patient will respond to the intended therapy.

86. The method according to clause 75, wherein the first checkpoint target molecule is PD-1 and the second checkpoint target molecule is PD-L1 or PD-L2, and wherein in determining the fluorescence signal score:
    (i) if the overall score is less than or equal to a threshold score, the overall score indicates or predicts that the patient will not respond to treatment with an anti-PD-1, anti-PD-L1 or anti-PD-L2 antibody; or
    (ii) if the overall score is greater than a threshold score, the overall score indicates or predicts that the patient will respond to treatment with an anti-PD-1, anti-PD-L1 or PD-L2 antibody.

87. The method according to clause 86 or 87, wherein the patient has not previously received cancer therapy or wherein the patient has not previously received a therapy targeting at least one of the checkpoint target molecules.

88. The method according to clauses 86 to 88, wherein if the overall score is 0.5% to 5%, this indicates the patient will not respond to a therapy targeting at least one of the checkpoint target molecules.

89. The method according to clauses 86 to 88, wherein if the overall score is 5% to 10%, this indicates the patient may respond to a therapy targeting at least one of the checkpoint target molecules.

90. The method according to clauses 86 to 88, wherein if the overall score is greater than 10%, this indicates the patient will respond to a therapy targeting at least one of the checkpoint target molecules.

91. The method according to clauses 86 to 90, wherein the overall score is the percentage FRET efficiency.

92. The method according to clauses 86 to 91, wherein the at least two primary antibodies bind to the first molecule or second molecule in such a manner that the checkpoint inhibitor or activator can bind to the first molecule or second molecule at the same time or subsequently.

93. The method according to clauses 86 to 92, wherein the at least two primary antibodies do not inhibit the binding of the checkpoint inhibitor or activator to the first molecule or the second molecule.

94. Use of the method according to clauses 86 to 93 in selecting a patient with cancer for treatment, wherein:
    a. where the intended therapy comprises a checkpoint activator targeting at least one of the first and second checkpoint target molecules:
        i. if the overall score is less than or equal to a threshold score, the overall score indicates or predicts that the patient will respond to the intended therapy; or
        ii. if the overall score is greater than a threshold score, the overall score indicates or predicts that the patient will not respond to the intended therapy; or
    b. where the intended therapy comprises a checkpoint inhibitor targeting at least one of the first and second checkpoint target molecules:
        i. if the overall score is less than or equal to a threshold score, the overall score indicates or predicts that the patient will not respond to the intended therapy; or
        ii. if the overall score is greater than a threshold score, the overall score indicates or predicts that the patient will respond to the intended therapy.

95. An in vitro coincidence assay method for detecting whether a checkpoint activator or inhibitor is effective in inhibiting or modulating a tumour response, the method comprising:
    at least two primary antibodies, wherein the first primary antibody binds to a first checkpoint target molecule on the first cell and the second primary antibody binds to a second checkpoint target molecule on the second cell, and wherein the first and secondary primary antibodies are immunologically distinct;
    at least two secondary antibodies, wherein a first secondary antibody binds to the first primary antibody; and a second secondary antibody binds the second primary antibody, wherein the first secondary antibody does not bind the second primary antibody and the second secondary antibody does not bind the first primary antibody; and wherein:
        (i) the first secondary antibody is labelled with a FRET donor and the second secondary antibody is labelled with a FRET acceptor;
        (ii) the first and second secondary antibodies are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
        (iii) the first secondary antibody is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme;
    wherein the method comprises:
        (a) contacting an isolated tumour cell sample with the at least two primary antibodies;
        (b) contacting the sample with the at least two secondary antibodies;
        (c) performing a wash step;
        (d) detecting the interaction between the secondary antibodies by determining the overall fluorescence score;
        (e) contacting the sample with the checkpoint activator or inhibitor;
        (f) detecting any change in the interaction between the secondary antibodies, wherein:
            a. where the checkpoint molecule is an inhibitor:
                i. if the overall score decreases between steps (d) and (f) it is indicated or predicted that the checkpoint inhibitor is effective; or
                ii. if the overall score is unchanged between steps (d) and (f) it is indicated or predicted that the checkpoint inhibitor is not effective; or
            b. where the checkpoint molecule is an activator:
                i. if the overall score increases between steps (d) and (f) it is indicated or predicted that the checkpoint activator is effective; or ii. if the overall score is unchanged between steps (d) and (f) it is indicated or predicted that the checkpoint activator is not effective.
96. The method according to clause 95, wherein the checkpoint inhibitor is an anti-PD-1 antibody, and the first primary antibody binds to PD-1 and the second primary antibody binds to PD-L1 or PD-L2.
97. The method according to clauses 95 or 96, wherein the checkpoint inhibitor is selected from the group consisting of ipilimumab, nivolumab (BMS-936558, DX 1106 or ONO-4538), pembrolizumab (iambrolizumab or MK-3475), pidilizumab (CT-Q1 1), ED-0680 (AMP-514), AMP-224, BMS-936559 (MDX-1 105), ED 4736, MPDL3280A (RG7448), MSB0010718C, and fragments and salts thereof.
98. The method according to clauses 95 to 97 wherein an overall score increase between steps (d) and (f) of 0.5% to 5%, preferably 5% to 10%, more preferably greater than 10%, indicates that the checkpoint activator will be effective.
99. The method according to clauses 95 to 97 wherein an overall score decrease between steps (d) and (f) of 0.5% to 5%, preferably 5% to 10%, more preferably greater than 10%, indicates that the checkpoint inhibitor will be effective.
100. The method according to clauses 95 to 99, wherein the at least two primary antibodies bind to the first molecule or second molecule in such a manner that the checkpoint inhibitor or activator can bind to the first molecule or second molecule at the same time or subsequently.
101. The method according to clauses 95 to 100, wherein the at least two primary antibodies do not inhibit the binding of the checkpoint inhibitor or activator to the first molecule or the second molecule.
102. Use of the in vitro coincidence assay method of any of clauses 95 to 101 for detecting whether a checkpoint inhibitor or activator will be effective in inhibiting or modulating a tumour response,
wherein:
  a. where the checkpoint molecule is an inhibitor:
    i. if the overall score decreases between steps (d) and (f) it is indicated or predicted that the checkpoint inhibitor is effective; or
    ii. if the overall score is unchanged between steps (d) and (f) it is indicated or predicted that the checkpoint inhibitor is not effective; or
  b. where the checkpoint molecule is an activator:
    iii. if the overall score increases between steps (d) and (f) it is indicated or predicted that the checkpoint activator is effective; or
    iv. if the overall score is unchanged between steps (d) and (f) it is indicated or predicted that the checkpoint activator is not effective.
103. A kit for use in an in vitro coincidence assay method for detecting whether a checkpoint inhibitor or activator is effective in inhibiting or modulating a tumour response, the kit comprising:
  (a) at least two primary antibodies, wherein the first primary antibody binds to a first checkpoint target molecule on the first cell and the second primary antibody binds to a second checkpoint target molecule on the second cell, and wherein the first and secondary primary antibodies are immunologically distinct;
  (b) at least two secondary antibodies, wherein a first secondary antibody binds to the first primary antibody; and a second secondary antibody binds the second primary antibody, wherein the first secondary antibody does not bind the second primary antibody and the second secondary antibody does not bind the first primary antibody; and wherein:
    (i) the first secondary antibody is labelled with a FRET donor and the second secondary antibody is labelled with a FRET acceptor;
    (ii) the first and second secondary antibodies are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
    (iii) the first secondary antibody is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme;
  (c) instructions for performing a method comprising:
    a. contacting an isolated tumour cell sample with the at least two primary antibodies;
    b. contacting the sample with the at least two secondary antibodies;
    c. performing a wash step;
    d. detecting the interaction between the secondary antibodies by determining the overall fluorescence score;
    e. contacting the sample with the checkpoint activator or inhibitor;
    f. detecting any change in the interaction between the secondary antibodies, wherein:
    where the checkpoint molecule is an inhibitor:
      i. if the overall score decreases between steps (d) and (f) it is indicated or predicted that the checkpoint inhibitor is effective; or
      ii. if the overall score is unchanged between steps (d) and (f) it is indicated or predicted that the checkpoint inhibitor is not effective; or where the checkpoint molecule is an activator:
      iii. if the overall score increases between steps (d) and (f) it is indicated or predicted that the checkpoint activator is effective; or
      iv. if the overall score is unchanged between steps (d) and (f) it is indicated or predicted that the checkpoint activator is not effective.
104. Use of the kit of clause 83 in an in vitro coincidence assay method for detecting whether a checkpoint inhibitor or activator is effective in inhibiting or modulating a tumour response, wherein:
  where the checkpoint molecule is an inhibitor:
    i. if the overall score decreases between steps (d) and (f) it is indicated or predicted that the checkpoint inhibitor is effective; or
    ii. if the overall score is unchanged between steps (d) and (f) it is indicated or predicted that the checkpoint inhibitor is not effective; or
  where the checkpoint molecule is an activator:
    iii. if the overall score increases between steps (d) and (f) it is indicated or predicted that the checkpoint activator is effective; or
    iv. if the overall score is unchanged between steps (d) and (f) it is indicated or predicted that the checkpoint activator is not effective.

105. An in vitro method of determining whether a therapy comprising a checkpoint activator or inhibitor is effective in a patient, the method comprising:
- at least two primary antibodies, wherein the first primary antibody binds to a first checkpoint target molecule on the first cell and the second primary antibody binds to a second checkpoint target molecule on the second cell, and wherein the first and secondary primary antibodies are immunologically distinct;
- at least two secondary antibodies, wherein a first secondary antibody binds to the first primary antibody; and a second secondary antibody binds the second primary antibody, wherein the first secondary antibody does not bind the second primary antibody and the second secondary antibody does not bind the first primary antibody; and wherein:
  - (i) the first secondary antibody is labelled with a FRET donor and the second secondary antibody is labelled with a FRET acceptor;
  - (ii) the first and second secondary antibodies are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
  - (iii) the first secondary antibody is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme;

wherein the method comprises:
- (a) contacting an isolated tumour cell sample obtained from the patient prior to the treatment comprising the checkpoint activator or inhibitor with at least two primary antibodies;
- (b) contacting the sample with the at least two secondary antibodies;
- (c) performing a wash step;
- (d) detecting the interaction between the secondary antibodies by determining the overall fluorescence score;
- (e) repeating steps (a) to (d) using an isolated tumour cell sample obtained from the patient during treatment comprising the checkpoint activator or inhibitor in step (a);
- (f) comparing the overall fluorescence scores between the samples, wherein:
  - a. where the therapy comprises a checkpoint inhibitor:
    - i. if the overall score decreases, it is indicated or predicted that the therapy is effective; or
    - ii. if the overall score is unchanged, it is indicated or predicted that the therapy is not effective; or
  - b. where the therapy comprises a checkpoint activator:
    - i. if the overall score increases, it is indicated or predicted that the therapy is effective; or
    - ii. if the overall score is unchanged, it is indicated or predicted that the therapy is not effective.

106. The method according to clause 105, wherein the checkpoint inhibitor is an anti-PD-1 antibody, and the first primary antibody binds to PD-1 and the second primary antibody binds to PD-L1 or PD-L2.

107. The method according to clauses 105 or 106, wherein the checkpoint inhibitor is selected from the group consisting of nivoiumab (BMS-936558, DX 1106 or ONO-4538), pembroiizumab (iambroiizumab or MK-3475), pidilizumab (CT-Q1 1), ED-0680 (AMP-514), AMP-224, BMS-936559 (MDX-1 105), ED 4736, MPDL3280A (RG7448), MSB0010718C, and fragments and salts thereof.

108. The method according to clauses 105 to 107 wherein an overall score increase of 0.5% to 5%, preferably 5% to 10%, more preferably greater than 10%, indicates that the therapy comprising a checkpoint activator will be effective.

109. The method according to clauses 105 to 107 wherein an overall score decrease of 0.5% to 5%, preferably 5% to 10%, more preferably greater than 10%, indicates that the therapy comprising a checkpoint inhibitor will be effective.

110. The method according to clauses 105 to 109, wherein the at least two primary antibodies bind to the first molecule or second molecule in such a manner that the checkpoint inhibitor or activator can bind to the first molecule or second molecule at the same time or subsequently.

111. The method according to clauses 105 to 110, wherein the at least two primary antibodies do not inhibit the binding of the checkpoint inhibitor or activator to the first molecule or the second molecule.

112. Use of the method according to clauses 105 to 111 for determining whether a therapy comprising a checkpoint activator or inhibitor is effective in a patient, wherein:
- c. where the therapy comprises a checkpoint inhibitor:
  - i. if the overall score decreases, it is indicated or predicted that the therapy is effective; or
  - ii. if the overall score is unchanged, it is indicated or predicted that the therapy is not effective; or
- d. where the therapy comprises a checkpoint activator:
  - i. if the overall score increases, it is indicated or predicted that the therapy is effective; or
  - ii. if the overall score is unchanged, it is indicated or predicted that the therapy is not effective.

113. A kit for use in an in vitro method of determining whether a therapy comprising a checkpoint activator or inhibitor is effective in a patient, the kit comprising:
- at least two primary antibodies, wherein the first primary antibody binds to a first checkpoint target molecule on the first cell and the second primary antibody binds to a second checkpoint target molecule on the second cell, and wherein the first and secondary primary antibodies are immunologically distinct;
- at least two secondary antibodies, wherein a first secondary antibody binds to the first primary antibody; and a second secondary antibody binds the second primary antibody, wherein the first secondary antibody does not bind the second primary antibody and the second secondary antibody does not bind the first primary antibody; and wherein:
  - (i) the first secondary antibody is labelled with a FRET donor and the second secondary antibody is labelled with a FRET acceptor;
  - (ii) the first and second secondary antibodies are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or (iii) the first secondary antibody is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme;

instructions for performing a method comprising:
(a) contacting an isolated tumour cell sample obtained from the patient prior to the treatment comprising the checkpoint activator or inhibitor with the at least two primary antibodies;
(b) contacting the sample with the at least two secondary antibodies;
(c) performing a wash step;
(d) detecting the interaction between the secondary antibodies by determining the overall fluorescence score;
(e) repeating steps (a) to (d) using an isolated tumour cell sample obtained from the patient during treatment comprising the checkpoint activator or inhibitor in step (a);
(f) comparing the overall fluorescence scores between the samples, wherein:
  a. where the therapy comprises a checkpoint inhibitor:
    i. if the overall score decreases, it is indicated or predicted that the therapy is effective; or
    ii. if the overall score is unchanged, it is indicated or predicted that the therapy is not effective; or
  b. where the therapy comprises a checkpoint activator:
    i. if the overall score increases, it is indicated or predicted that the therapy is effective; or
    ii. if the overall score is unchanged, it is indicated or predicted that the therapy is not effective.

114. Use of the kit of clause 113 in an in vitro method of determining whether a therapy comprising a checkpoint activator or inhibitor has is effective in a patient, wherein:
  a. where the therapy comprises a checkpoint inhibitor:
    i. if the overall score decreases, it is indicated or predicted that the therapy is effective; or
    ii. if the overall score is unchanged, it is indicated or predicted that the therapy is not effective; or
  b. where the therapy comprises a checkpoint activator:
    i. if the overall score increases, it is indicated or predicted that the therapy is effective; or
    ii. if the overall score is unchanged, it is indicated or predicted that the therapy is not effective.

115. An in vitro coincidence assay method for identifying whether a molecule of interest is a checkpoint activator or a checkpoint inhibitor, the method comprising:
at least two primary antibodies, wherein the first primary antibody binds to a first checkpoint target molecule on the first cell and the second primary antibody binds to a second checkpoint target molecule on the second cell, and wherein the first and secondary primary antibodies are immunologically distinct;
at least two secondary antibodies, wherein a first secondary antibody binds to the first primary antibody; and a second secondary antibody binds the second primary antibody, wherein the first secondary antibody does not bind the second primary antibody and the second secondary antibody does not bind the first primary antibody; and wherein:
(i) the first secondary antibody is labelled with a FRET donor and the second secondary antibody is labelled with a FRET acceptor;
(ii) the first and second secondary antibodies are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
(iii) the first secondary antibody is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme;
wherein the method comprises:
(a) contacting an isolated tumour cell sample with the at least two primary antibodies;
(b) contacting the sample with the at least two secondary antibodies;
(c) performing a wash step;
(d) detecting the interaction between the secondary antibodies by determining the overall fluorescence score;
(e) contacting the sample with the molecule of interest;
(f) detecting any change in the interaction between the secondary antibodies, wherein:
  a. the molecule is a checkpoint activator for at least one of the first and second checkpoint target molecules if the overall score increases between steps (d) and (f); or
  b. the molecule is a checkpoint inhibitor for at least one of the first and second checkpoint target molecules if the overall score is decreases between steps (d) and (f); or
  c. the molecule is neither a checkpoint activator nor inhibitor for at least one of the first and second checkpoint target molecules if the overall score is unchanged between steps (d) and (f).

116. The method according to clause 115 wherein an overall score increase between steps (d) and (f) of 0.5% to 5%, preferably 5% to 10%, more preferably greater than 10%, indicates that the molecule of interest is a checkpoint activator for at least one of the first and second checkpoint target molecules.

117. The method according to clause 115 wherein an overall score decrease between steps (d) and (f) of 5% to 0.5%, preferably 10% to 5%, more preferably greater than 10%, indicates that the molecule of interest is a checkpoint inhibitor for at least one of the first and second checkpoint target molecules.

118. The method according to clauses 115 to 117, wherein the at least two primary antibodies bind to the first molecule or second molecule in such a manner that the molecule of interest can bind to the first molecule or second molecule at the same time or subsequently.

119. The method according to clauses 115 to 117, wherein the at least two primary antibodies do not inhibit the binding of the molecule of interest to the first molecule or the second molecule.

120. An in vitro method of determining whether a patient with cancer will be responsive to an agent that blocks the PD-1:PD-L1/PD-L2 pathway, the method comprising:
at least two primary antibodies, wherein a first primary antibody binds to PD-1 on the first cell and a second primary antibody binds to PD-L1 or PD-L2 on the second cell, and wherein the first and secondary primary antibodies are immunologically distinct; and at least two secondary antibodies, wherein a first secondary antibody binds to the first primary antibody; and a second secondary antibody binds the second primary antibody, wherein the first secondary antibody does not bind the second primary antibody and the second secondary antibody does not bind the first primary antibody; and wherein:
  (i) the first secondary antibody is labelled with a FRET donor and the second secondary antibody is labelled with a FRET acceptor;
  (ii) the first and second secondary antibodies are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
  (iii) the first secondary antibody is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme;

the method comprising:
  (a) contacting an isolated tumour cell sample obtained from the patient with the at least two primary antibodies;
  (b) contacting the sample with the at least two secondary antibodies;
  (c) performing a wash step;
  (d) detecting the interaction between the secondary antibodies by determining the overall fluorescence signal score, wherein:
    (i) if the overall score is less than or equal to a threshold score, the overall score indicates or predicts that the patient will not respond to treatment with an agent that blocks the PD-1:PD-L1/PD-L2 pathway; or
    (ii) if the overall score is greater than a threshold score, the overall score indicates or predicts that the patient will respond to treatment with an agent that blocks the PD-1:PD-L1/PD-L2 pathway.

121. The method of clause 120, wherein the sample is a fixed tumour cell sample.

122. The method of clauses 120 to 121, wherein the method is performed:
  (i) on a biological sample obtained from the patient prior to treatment to guide the decision on selection of treatment with a single agent that blocks the PD-1:PD-L1/PD-L2 pathway, or with an agent that blocks the PD-1:PD-L1/PD-L2 pathway and at least one other anti-tumour agent in a combination therapy; and
  (ii) on at least one biological sample obtained from the patient during treatment to monitor response of the subject to the current treatment regimen and to guide decision on selection of treatment with a single-agent PD-1:PD-L1/PD-L2 blockade therapy or with a combination therapy.

123. Use of the in vitro method of any of clauses 120 to 122 for determining whether a patient with cancer will be responsive to an agent that blocks the PD-1:PD-L1/PD-L2 pathway, wherein:
  (i) if the overall score is less than or equal to a threshold score, the overall score indicates or predicts that the patient will not respond to treatment with an agent that blocks the PD-1:PD-L1/PD-L2 pathway; or
  (ii) if the overall score is greater than a threshold score, the overall score indicates or predicts that the patient will respond to treatment with an agent that blocks the PD-1:PD-L1/PD-L2 pathway.

124. A kit for use in an in vitro method of determining whether a patient with cancer will be responsive to an agent that blocks the PD-1:PD-L1/PD-L2 pathway, the kit comprising:
  at least two primary antibodies, wherein the first primary antibody binds to PD-1 on the first cell and the second primary antibody binds to PD-L1 or PD-L2 on the second cell, and wherein the first and secondary primary antibodies are immunologically distinct; and
  at least two secondary antibodies, wherein the first secondary antibody binds to the first primary antibody; and the second secondary antibody binds the second primary antibody, wherein the first secondary antibody does not bind the second primary antibody and the second secondary antibody does not bind the first primary antibody; and wherein:
    (i) the first secondary antibody is labelled with a FRET donor and the second secondary antibody is labelled with a FRET acceptor;
    (ii) the first and second secondary antibodies are conjugated or fused to a DNA sequence, wherein the DNA sequences are different and ligate to form a circle and are amplified by rolling circle DNA amplification, and are bound by externally applied fluorescently labelled DNA probes complimentary to that of the amplified DNA sequences; or
    (iii) the first secondary antibody is labelled with a FRET donor and the second secondary antibody is fused to an enzyme which reacts with a conjugate comprising a FRET acceptor and a substrate specific enzyme to form an activated conjugate that binds to electron rich moieties on a molecular surface adjacent to the enzyme; and
  instructions for performing a method comprising:
    a. contacting an isolated tumour cell sample obtained from the patient with the at least two primary antibodies;
    b. contacting the sample with the at least two secondary antibodies;
    c. performing a wash step;
    d. detecting the interaction between the secondary antibodies by determining the overall fluorescence signal score, wherein:
      (i) if the overall score is less than or equal to a threshold score, the overall score indicates or predicts that the patient will not respond to treatment with an agent that blocks the PD-1:PD-L1/PD-L2 pathway; or
      (ii) if the overall score is greater than a threshold score, the overall score indicates or predicts that the patient will respond to treatment with an agent that blocks the PD-1:PD-L1/PD-L2 pathway.

125. The kit of clause 124, wherein the sample is a fixed tumour cell sample.

126. The kit of any of clauses 124 to 125, wherein the instructions for performing the method further comprise instructions to perform the method:
  (i) on a biological sample obtained from the patient prior to treatment to guide the decision on selection of treatment with a single agent that blocks the PD-1:PD-L1/PD-L2 pathway, or with an agent that blocks the PD-1:PD-L1/PD-L2 pathway and at least one other anti-tumour agent in a combination therapy; and (ii) on at least one biological sample obtained from the patient during treatment to monitor response of the subject to the current treatment regimen and to guide decision on selection of treatment with a single-agent PD-1:PD-L1/PD-L2 blockade therapy or with a combination therapy.

127. Use of the kit of any of clauses 124 to 126 in an in vitro method of determining whether a patient with cancer will be responsive to an agent that blocks the PD-1:PD-L1/PD-L2 pathway, wherein:

(i) if the overall score is less than or equal to a threshold score, the overall score indicates or predicts that the patient will not respond to treatment with an agent that blocks the PD-1:PD-L1/PD-L2 pathway; or (ii) if the overall score is greater than a threshold score, the overall score indicates or predicts that the patient will respond to treatment with an agent that blocks the PD-1:PD-L1/PD-L2 pathway.

128. An in vitro coincidence assay method for detecting the interaction between a first molecule expressed on a first cell and a second molecule expressed on a second cell, the method comprising:

a first and second fusion protein, wherein each fusion protein comprises a detection domain, a recognition domain and a connector domain;

the detection domain comprises a DNA binding domain and is capable of binding a cognate specific nucleotide sequence in co-operation with a further detection domain;

the recognition domain is capable of binding a target molecule; the connector domain is fused at one end to the detection domain and fused at the other end to the recognition domain;

the detection domain, recognition domain and connector domain are heterologous to one another;

the method comprising the steps of:
(i) contacting the sample with the first and fusion proteins;
(ii) incubating to allow binding;
(iii) removing unbound fusion protein;
(iv) contacting the sample with nucleic acid comprising the cognate specific nucleotide sequence;
(v) incubating to allow heterotrimeric binding of the nucleic acid; and
(vi) detecting nucleic acid bound to the sample;

wherein, if the nucleic acid is detected in step (vi), this indicates that the two target molecules are present coincidentally in the sample.

The invention claimed is:

1. An in vitro method for detecting a lifetime reduction indicative of cell-cell interactions, the method comprising:
i. contacting an isolated sample containing a first cell and a second cell with at least two primary binding agents comprising a first primary binding agent and a second primary binding agent to obtain a first cell sample mixture;
ii. contacting the first cell sample mixture with at least two secondary binding agents comprising a first secondary binding agent and a second secondary binding agent to obtain a second cell sample mixture, wherein the first secondary binding agent is labeled with a fluorescence resonance energy transfer (FRET) donor and an enzyme is fused to the second secondary binding agent;
iii. washing the second cell sample mixture to obtain a third cell sample mixture;
iv. contacting the third cell sample mixture with a conjugate comprising a FRET acceptor and a substrate, said contacting taking place under conditions selected to react the enzyme with the substrate to thereby label a molecular surface or surfaces adjacent to the enzyme with the FRET acceptor; and
v. detecting the lifetime reduction between the FRET donor and the FRET acceptor;
wherein the first primary binding agent binds to a first molecule on the first cell and the second primary binding agent binds to a second molecule on the second cell, wherein the first and second primary binding agents are immunologically distinct, wherein the first secondary binding agent binds to the first primary binding agent, and wherein the second secondary binding agent binds to the second primary binding agent,
wherein the first secondary binding agent does not bind to the second primary binding agent and the second secondary binding agent does not bind to the first primary binding agent; and
wherein said first and second primary binding agents are each independently selected from the group consisting of whole immunoglobulins, antibody scaffolds, antibody, antigen-binding fragments thereof, and combination thereof, and wherein said first and second secondary binding agents are each independently selected from the group consisting of whole immunoglobulins, antibody scaffolds, antibody, antigen-binding fragments thereof, and combination thereof, and
wherein the first cell is different from the second cell.

2. The in vitro method of claim 1, wherein said detecting the lifetime reduction between the FRET donor and the FRET acceptor is by detecting an emitted fluorescence, or wherein said detecting the lifetime reduction between the FRET donor and the FRET acceptor is by detecting an altered fluorescence behavior.

3. The in vitro method of claim 2, wherein said detecting of the altered fluorescence behaviour is time-resolved.

4. The in vitro method according to claim 1, wherein the isolated sample is a fixed cell sample.

5. The in vitro method of claim 4, wherein the isolated sample is a fixed tumor cell sample.

6. The in vitro method according to claim 1, wherein the first and second molecules are proteins.

7. The in vitro method according to claim 6, wherein the first molecule is programmed cell death-1 (PD-1) and the second molecule is programmed cell death-ligand 1 (PD-L1) or programmed cell death-ligand 2 (PD-L2).

8. The in vitro method according to claim 6, wherein the first primary binding agent binds to PD-1 on the first cell and the second primary binding agent binds to PD-L1 or PD-L2 on the second cell, wherein the method detects the lifetime reduction indicative of binding of PD-1 on the first cell to PD-L1 or PD-L2 on the second cell.

9. The in vitro method according to claim 6, wherein the first molecule is cytotoxic T-lymphocyte-associated protein 4 (CTLA-4) or CD28 and the second molecule is CD80 or CD86, wherein the first primary binding agent binds to CTLA-4 or CD28 on the first cell and the second primary binding agent binds to CD80 or CD86 on the second cell, wherein the method detects the lifetime reduction indicative of binding of CTLA-4 or CD28 on the first cell to CD80 or CD86 on the second cell.

10. The in vitro method according to claim 6, wherein the first molecule is a major histocompatibility complex (MHC)

Class I or II peptide and the second molecule is selected from T-cell receptor (TCR), CD8, CD3 and combinations thereof,
wherein the first primary binding agent binds to the MHC class I or MHC class II peptide and the second primary binding agent binds to TCR, CD83, CD3 or combinations thereof on the second cell, wherein the method detects the lifetime reduction indicative of binding of the MHC class I or MHC class II peptide on the first cell to TCR, CD83, CD3 or combinations thereof on the second cell.

11. The in vitro method of claim 1, wherein the first cell is a lymphocyte and/or wherein the second cell is a non-lymphocyte cell.

12. The in vitro method of claim 11, wherein the method detects the lifetime reduction indicative of interaction between PD-1 on a first lymphocyte cell and PD-L1 or PD-L2 on a second non-lymphocyte cell, or
wherein the method detects the lifetime reduction indicative of interaction between CTLA-4 or CD28 on a first lymphocyte cell and CD80 or CD86 on a second non-lymphocyte cell, or
wherein the method detects the lifetime reduction indicative of interaction between an MHC Class I or II peptide on a first lymphocyte cell and TCR, CD8, CD3 or combinations thereof on a second non-lymphocyte cell.

13. The in vitro method of claim 1,
wherein at least one of the secondary binding agents is an antibody scaffold, antibody or antigen-binding fragment, or
wherein the at least two secondary binding agents are antibody scaffolds, antibody binding fragments or antigen-binding fragments.

14. The in vitro method according to claim 13, wherein the antibody or antigen-binding fragments are Fab fragments, scFv fragments or combinations thereof, or
wherein the antibody scaffolds are selected from adnectins, affibodies, affilins, anticalins, atrimers, avimers, bicyclic peptides, centyrins, cys-knots, DARPins, fynomers, Kunitz domains, Obodies, and Tn3s.

15. The in vitro method according to claim 1, wherein the first and second primary binding agents are unlabeled, or wherein the first primary binding agent is a murine binding agent and the second primary binding agent is a rabbit binding agent, wherein the first secondary binding agent is an anti-murine binding agent and the second secondary binding agent is an anti-rabbit binding agent.

16. The in vitro method of claim 1, wherein the FRET donor is selected from the group consisting of Oregon Green 488 (ORG 488), Green Fluorescent Protein (GFP), fluorescein, 5-{[2-(2-Iodoacetamido)ethyl]amino}naphthalene-1-sulfonic acid (IAEDANS), 5-((2-Aminoethyl)amino)naphthalene-1-sulfonic acid (EDANS), 4,4-difluoro-4-bora-3a, 4a-diaza-s-indacene (BODIPY FL), ATTO488 and combinations thereof, or
wherein the FRET acceptor is selected from the group consisting of: ALX 594, monomeric red fluorescent protein (mRFP), tetramethylrhodamine, fluorescein, 4-((4-(dimethylamino)phenyl)azo)benzoic acid (dabcyl), 4,4-difluoro-4-bora-3a,4a-diaza-s-indacene (BODIPY FL), QSY 7, QSY 9 and combinations thereof, or
wherein the at least one enzyme is selected from the group consisting of oxidoreductases, hydrolases, lyases, transferases, isomerases, and ligases, or wherein the substrate is tyramide, or
wherein the at least two primary binding agents are contacted with the isolated sample sequentially to one another, or
wherein the at least two secondary binding agents are contacted with the first cell sample mixture sequentially to one another, or
the method further comprising quantifying the lifetime reduction indicative of interaction between the first molecule on the first cell and the second molecule on the second cell, or
wherein the first molecule is located on the cell surface of the first cell and the second molecule is located on the cell surface of the second cell, or
wherein the method further comprises administering a checkpoint inhibitor or activator targeting a first checkpoint target molecule of the first molecule and a second checkpoint target molecule of the second molecule, the at least two primary binding agents binding to the first molecule or second molecule in such a manner that the checkpoint inhibitor or activator can bind to the first molecule or second molecule at the same time or subsequently, or
wherein the at least two primary binding agents do not inhibit the binding of a checkpoint inhibitor or activator to the first molecule or the second molecule.

17. The in vitro method of claim 1, wherein the substrate is tyramide.

18. The in vitro method according to claim 1, wherein the first and second molecules are immune checkpoint proteins.

19. The in vitro method of claim 1, wherein the first cell is a T-cell and the second cell is an antigen-presenting cell.

20. The in vitro method of claim 1, wherein the enzyme is selected from the group consisting of horseradish peroxidase, glucose oxidase, alkaline phosphatase, and beta-galactosidase.

21. The in vitro method of claim 1, wherein the conditions selected to react the enzyme with the substrate comprise forming an activated conjugate that binds to electron rich moieties on the molecular surface or surfaces adjacent to the enzyme.

22. The in vitro method of claim 1, wherein detecting the lifetime reduction between the FRET donor and the FRET acceptor comprises detecting lifetime reduction of the FRET donor when within 10 nm of the FRET acceptor.

23. The in vitro method of claim 1, wherein the first molecule is located on a cell surface of the first cell, and the second molecule is located on a cell surface of the second cell.

24. A kit for detecting the lifetime reduction indicative of cell-cell interactions determined according to the in vitro method of claim 1, comprising:
said at least two primary binding agents comprising the first primary binding agent and the second primary binding agent to contact to the isolated sample containing the first cell and the second cell for obtaining the first cell sample mixture;
said at least two secondary binding agents comprising the first secondary binding agent and the second secondary binding agent to contact the first cell sample mixture for obtaining the second cell sample mixture;
a liquid to wash the second cell sample mixture for obtaining the third cell sample mixture; and
the conjugate comprising the FRET acceptor and the substrate to contact to the third cell sample mixture for reacting with the substrate to thereby label the molecular surface or surfaces adjacent to the enzyme with the FRET acceptor.

\* \* \* \* \*